United States Patent
Sorensen et al.

(10) Patent No.: US 7,332,508 B2
(45) Date of Patent: Feb. 19, 2008

(54) SUBSTITUTED HOMOPIPERIDINE, PIPERIDINE OR PYRROLIDINE DERIVATIVES

(75) Inventors: Jan Lindy Sorensen, Farum (DK);
Knud Erik Andersen, Brondby (DK);
Ingrid Pettersson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 281 days.

(21) Appl. No.: 10/735,963

(22) Filed: Dec. 15, 2003

(65) Prior Publication Data

US 2005/0107434 A1  May 19, 2005

Related U.S. Application Data

(60) Provisional application No. 60/460,777, filed on Apr. 4, 2003, provisional application No. 60/434,253, filed on Dec. 18, 2002.

(30) Foreign Application Priority Data

Dec. 18, 2002 (DK) .................. 2002 01932
Mar. 31, 2003 (DK) .................. 2003 00484

(51) Int. Cl.
*A61K 31/454* (2006.01)
*C07D 43/02* (2006.01)

(52) U.S. Cl. .............. 514/326; 546/208; 546/210; 546/211

(58) Field of Classification Search ........... 514/326; 546/208, 210, 211
See application file for complete search history.

(56) References Cited

U.S. PATENT DOCUMENTS 4,481,360 A * 11/1984 Gall et al. ............. 546/210
4,837,241 A * 6/1989 Jensen et al. ........... 514/340
5,397,785 A * 3/1995 Ninomiya et al. ....... 514/291
5,854,261 A * 12/1998 Bosmans ............... 514/320
6,645,980 B1 * 11/2003 Cuny et al. ............ 514/312

FOREIGN PATENT DOCUMENTS

| EP | 0239309 A2 | 9/1987 |
|----|------------|--------|
| EP | 0259621 A2 | 3/1988 |
| EP | 0259621 B1 | 3/1988 |
| WO | WO 93/13083 A1 | 7/1993 |
| WO | WO 00/39125 A1 | 7/2000 |

OTHER PUBLICATIONS

Ohki et al. "Cyclohexapeptides having . . . " CA 129:54604 (1998).*
Jensen et al. "Preparation and testing of . . . " CA 109:6526 (1988).*
Ohki et al. "Cyclohexapeptides . . . " CA 129:54604 (1998).*
King "Medicinal chemistry" Cambridge, p. 206-209 (1994).*
Greene "Protective groups in organic synthesis" Wiley int. p. 152-154, 158, 187, 189 (1982).*
Williams et al., Combinatorial Chemistry & High Throughput Screening, vol. 3, pp. 43-50 (2000).

* cited by examiner

*Primary Examiner*—Celia Chang
(74) *Attorney, Agent, or Firm*—Rosemarie R. Wilk-Orescan

(57) ABSTRACT

A novel class of substituted homopiperidine, piperidine and pyrrolidine derivatives, methods for their preparation, pharmaceutical compositions comprising them and use thereof in the treatment of disorders related to the histamine H3 receptor. More particularly, the compounds possess histamine H3 receptor antagonistic activity and are thus useful in the treatment of disorders in which a histamine H3 receptor blockade is beneficial.

45 Claims, No Drawings

SEQUENCE LISTING

```
<160> NUMBER OF SEQ ID NOS: 3

<210> SEQ ID NO 1
<211> LENGTH: 445
<212> TYPE: PRT
<213> ORGANISM: Homo sapiens

<400> SEQUENCE: 1

Met Glu Arg Ala Pro Pro Asp Gly Pro Leu Asn Ala Ser Gly Ala Leu
1               5                   10                  15

Ala Gly Glu Ala Ala Ala Ala Gly Gly Ala Arg Gly Phe Ser Ala Ala
```

-continued

```
                    20                  25                  30
Trp Thr Ala Val Leu Ala Ala Leu Met Ala Leu Leu Ile Val Ala Thr
                35                  40                  45
Val Leu Gly Asn Ala Leu Val Met Leu Ala Phe Val Ala Asp Ser Ser
            50                  55                  60
Leu Arg Thr Gln Asn Asn Phe Phe Leu Leu Asn Leu Ala Ile Ser Asp
65                  70                  75                  80
Phe Leu Val Gly Ala Phe Cys Ile Pro Leu Tyr Val Pro Tyr Val Leu
                        85                  90                  95
Thr Gly Arg Trp Thr Phe Gly Arg Gly Leu Cys Lys Leu Trp Leu Val
                100                 105                 110
Val Asp Tyr Leu Leu Cys Thr Ser Ser Ala Phe Asn Ile Val Leu Ile
            115                 120                 125
Ser Tyr Asp Arg Phe Leu Ser Val Thr Arg Ala Val Ser Tyr Arg Ala
        130                 135                 140
Gln Gln Gly Asp Thr Arg Arg Ala Val Arg Lys Met Leu Leu Val Trp
145                 150                 155                 160
Val Leu Ala Phe Leu Leu Tyr Gly Pro Ala Ile Leu Ser Trp Glu Tyr
                165                 170                 175
Leu Ser Gly Gly Ser Ser Ile Pro Glu Gly His Cys Tyr Ala Glu Phe
                180                 185                 190
Phe Tyr Asn Trp Tyr Phe Leu Ile Thr Ala Ser Thr Leu Glu Phe Phe
            195                 200                 205
Thr Pro Phe Leu Ser Val Thr Phe Phe Asn Leu Ser Ile Tyr Leu Asn
    210                 215                 220
Ile Gln Arg Arg Thr Arg Leu Arg Leu Asp Gly Ala Arg Glu Ala Ala
225                 230                 235                 240
Gly Pro Glu Pro Pro Glu Ala Gln Pro Ser Pro Pro Pro Pro Pro Pro
                245                 250                 255
Gly Cys Trp Gly Cys Trp Gln Lys Gly His Gly Glu Ala Met Pro Leu
                260                 265                 270
His Arg Tyr Gly Val Gly Glu Ala Ala Val Gly Ala Glu Ala Gly Glu
            275                 280                 285
Ala Thr Leu Gly Gly Gly Gly Gly Gly Ser Val Ala Ser Pro Thr
    290                 295                 300
Ser Ser Ser Gly Ser Ser Ser Arg Gly Thr Glu Arg Pro Arg Ser Leu
305                 310                 315                 320
Lys Arg Gly Ser Lys Pro Ser Ala Ser Ser Ala Ser Leu Glu Lys Arg
                325                 330                 335
Met Lys Met Val Ser Gln Ser Phe Thr Gln Arg Phe Arg Leu Ser Arg
            340                 345                 350
Asp Arg Lys Val Ala Lys Ser Leu Ala Val Ile Val Ser Ile Phe Gly
        355                 360                 365
Leu Cys Trp Ala Pro Tyr Thr Leu Leu Met Ile Ile Arg Ala Ala Cys
    370                 375                 380
His Gly His Cys Val Pro Asp Tyr Trp Tyr Glu Thr Ser Phe Trp Leu
385                 390                 395                 400
Leu Trp Ala Asn Ser Ala Val Asn Pro Val Leu Tyr Pro Leu Cys His
                405                 410                 415
His Ser Phe Arg Arg Ala Phe Thr Lys Leu Leu Cys Pro Gln Lys Leu
            420                 425                 430
Lys Ile Gln Pro His Ser Ser Leu Glu His Cys Trp Lys
    435                 440                 445
```

<210> SEQ ID NO 2
<211> LENGTH: 445
<212> TYPE: PRT
<213> ORGANISM: monkey

<400> SEQUENCE: 2

```
Met Glu Arg Ala Pro Pro Asp Gly Pro Leu Asn Ala Ser Gly Ala Leu
1               5                   10                  15

Ala Gly Glu Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
        35                  40                  45

Val Leu Gly Asn Ala Leu Val Met Leu Ala Phe Val Ala Asp Ser Ser
    50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140

Gln Gln Gly Asn Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
        195                 200                 205

Thr Pro Phe Leu Ser Val Thr Phe Phe Asn Leu Ser Ile Tyr Leu Asn
    210                 215                 220

Ile Gln Arg Arg Thr Arg Leu Arg Leu Asp Gly Ala Arg Glu Ala Gly
225                 230                 235                 240

Gly Pro Glu Pro Pro Pro Glu Ala Gln Pro Ser Pro Pro Pro Pro
                245                 250                 255

Gly Cys Trp Gly Cys Trp Gln Lys Gly His Gly Glu Ala Met Pro Leu
            260                 265                 270

His Arg Tyr Gly Val Gly Glu Ala Ala Ala Gly Ala Glu Ala Gly Glu
        275                 280                 285

Thr Ala Leu Gly Gly Gly Gly Gly Gly Ser Ala Ala Ser Pro Thr
    290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                325                 330                 335

Met Lys Met Val Ser Gln Ser Phe Thr Gln Arg Phe Arg Leu Ser Arg
            340                 345                 350

Asp Arg Lys Val Ala Lys Ser Leu Ala Val Ile Val Ser Ile Phe Gly
        355                 360                 365

Leu Cys Trp Ala Pro Tyr Thr Leu Leu Met Ile Ile Arg Ala Ala Cys
```

```
                370             375             380
His Gly His Cys Val Pro Asp Tyr Trp Tyr Glu Thr Ser Phe Trp Leu
385                 390                             400

Leu Trp Ala Asn Ser Ala Val Asn Pro Val Leu Tyr Pro Leu Cys His
                405                 410                 415

His Ser Phe Arg Arg Ala Phe Thr Lys Leu Leu Cys Pro Gln Lys Leu
                420                 425                 430

Lys Ile Gln Pro His Ser Ser Leu Glu Gln Cys Trp Lys
            435                 440                 445

<210> SEQ ID NO 3
<211> LENGTH: 445
<212> TYPE: PRT
<213> ORGANISM: rat

<400> SEQUENCE: 3

Met Glu Arg Ala Pro Pro Asp Gly Leu Met Asn Ala Ser Gly Thr Leu
1               5                   10                  15

Ala Gly Glu Ala Ala Ala Gly Gly Ala Arg Gly Phe Ser Ala Ala
                20                  25                  30

Trp Thr Ala Val Leu Ala Ala Leu Met Ala Leu Leu Ile Val Ala Thr
                35                  40                  45

Val Leu Gly Asn Ala Leu Val Met Leu Ala Phe Val Ala Asp Ser Ser
50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
                100                 105                 110

Val Asp Tyr Leu Leu Cys Ala Ser Ser Val Phe Asn Ile Val Leu Ile
                115                 120                 125

Ser Tyr Asp Arg Phe Leu Ser Val Thr Arg Ala Val Ser Tyr Arg Ala
130                 135                 140

Gln Gln Gly Asp Thr Arg Arg Ala Val Arg Lys Met Ala Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
                180                 185                 190

Phe Tyr Asn Trp Tyr Phe Leu Ile Thr Ala Ser Thr Leu Glu Phe Phe
                195                 200                 205

Thr Pro Phe Leu Ser Val Thr Phe Phe Asn Leu Ser Ile Tyr Leu Asn
210                 215                 220

Ile Gln Arg Arg Thr Arg Leu Arg Leu Asp Gly Gly Arg Glu Ala Gly
225                 230                 235                 240

Pro Glu Pro Pro Asp Ala Gln Pro Ser Pro Pro Ala Pro Pro
                245                 250                 255

Ser Cys Trp Gly Cys Trp Pro Lys Gly His Gly Glu Ala Met Pro Leu
                260                 265                 270

His Arg Tyr Gly Val Gly Glu Ala Gly Pro Gly Val Glu Ala Gly Glu
                275                 280                 285

Ala Ala Leu Gly Gly Gly Ser Gly Gly Gly Ala Ala Ala Ser Pro Thr
                290                 295                 300
```

-continued

| | | | | | | | | | | | |
|---|---|---|---|---|---|---|---|---|---|---|---|
| Ser 305 | Ser | Ser | Gly | Ser 310 | Ser | Ser | Arg | Gly | Thr | Glu 315 | Arg | Pro | Arg | Ser | Leu 320 |

| Lys | Arg | Gly | Ser 325 | Lys | Pro | Ser | Ala | Ser 330 | Ser | Ala | Ser | Leu | Glu | Lys 335 | Arg |

| Met | Lys | Met | Val 340 | Ser | Gln | Ser | Ile | Thr 345 | Gln | Arg | Phe | Arg | Leu 350 | Ser | Arg |

| Asp | Lys | Lys 355 | Val | Ala | Lys | Ser | Leu 360 | Ala | Ile | Ile | Val | Ser 365 | Ile | Phe | Gly |

| Leu | Cys 370 | Trp | Ala | Pro | Tyr | Thr 375 | Leu | Leu | Met | Ile | Ile 380 | Arg | Ala | Ala | Cys |

| His 385 | Gly | Arg | Cys | Ile | Pro 390 | Asp | Tyr | Trp | Tyr | Glu 395 | Thr | Ser | Phe | Trp | Leu 400 |

| Leu | Trp | Ala | Asn | Ser 405 | Ala | Val | Asn | Pro | Val 410 | Leu | Tyr | Pro | Leu | Cys 415 | His |

| Tyr | Ser | Phe | Arg 420 | Arg | Ala | Phe | Thr | Lys 425 | Leu | Leu | Cys | Pro | Gln 430 | Lys | Leu |

| Lys | Val | Gln | Pro | His 435 | Gly | Ser | Leu | Glu 440 | Gln | Cys | Trp | Lys 445 |

SUBSTITUTED HOMOPIPERIDINE, PIPERIDINE OR PYRROLIDINE DERIVATIVES

CROSS-REFERENCE TO RELATED APPLICATIONS

This application claims priority under 35 U.S.C. 119 of Danish applications nos. PA 2002 01932 filed Dec. 18, 2002 and PA 2003 00484 filed Mar. 31, 2003 and U.S. applications Ser. Nos. 60/434,253 filed Dec. 18, 2002 and 60/460,777 filed Apr. 4, 2003, the contents of each of which are fully incorporated herein by reference.

The present invention relates to novel substituted homopiperidine, piperidine or pyrrolidine derivatives, to the use of these compounds as pharmaceutical compositions, to pharmaceutical compositions comprising the compounds, and to a method of treatment employing these compounds and compositions. The present compounds show a high and selective binding affinity to the histamine H3 receptor indicating histamine H3 receptor antagonistic, inverse agonistic or agonistic activity. As a result, the compounds are useful for the treatment of diseases and disorders related to the histamine H3 receptor.

BACKGROUND OF THE INVENTION

The existence of the histamine H3 receptor has been known for several years and the receptor is of current interest for the development of new medicaments. Recently, the human histamine H3 receptor has been cloned. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (i.e. it is active in the absence of an agonist). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Several publications disclose the preparation and use of histamine H3 agonists and antagonists. Most of these are imidazole derivatives. However, recently some imidazole-free ligands of the histamine H3 receptor have been described.

In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of substituted homopiperidines, piperidines or pyrrolidines has a high and specific affinity to and potency at the histamine H3 receptor. Structurally related compounds are known from e.g. WO 93/13083, WO 00/39125, EP 239309, EP 259621 and Comb. Chem. and High Throughput Screen. 2000, 3, 43-50. However, none of the compounds in these references are disclosed as having an effect on the H3 receptor.

Due to their interaction with the histamine H3 receptor, the present compounds are useful in the treatment of a wide range of conditions and disorders in which an interaction with the histamine H3 receptor is beneficial. Thus, the compounds may find use e.g. in the treatment of diseases of the central nervous system, the peripheral nervous system, the cardiovascular system, the pulmonary system, the gastrointestinal system and the endocrinological system.

SUMMARY OF THE INVENTION

The invention provides compounds of the general formula (I):

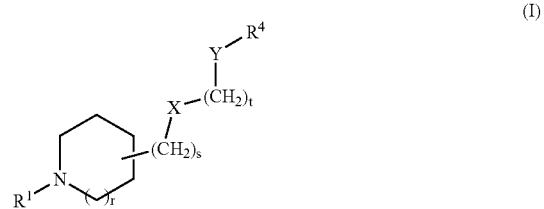

wherein
$R^1$ is
$C_{1-6}$-alkyl, $C_{2-6}$-alkenyl, $C_{2-6}$-alkynyl,
which may optionally be substituted with one or more substituents selected from halogen, $C_{1-6}$-alkoxy and hydroxy,
$C_{3-8}$-cycloalkyl, $C_{5-8}$-cycloalkenyl, $C_{3-8}$-cycloalkyl-$C_{1-6}$-alkyl, di($C_{3-8}$-cycloalkyl)-$C_{1-6}$-alkyl, $C_{3-8}$-cycloalkyl-$C_{2-6}$-alkenyl, $C_{3-8}$-cycloalkyl-$C_{2-6}$-alkynyl, $C_{5-8}$-cycloalkenyl-$C_{1-6}$-alkyl, $C_{5-8}$-cycloalkenyl-$C_{2-4}$-alkenyl, $C_{5-8}$-cycloalkenyl-$C_{2-6}$-alkynyl, 4-pyridyl or tetrahydropyranyl,
wherein the cyclic moieties may optionally be substituted with one or more substituents selected from $C_{1-6}$-alkyl, halogen, trifluoromethyl and 2,2,2-trifluoroethyl,
r is 0, 1 or 2,
s is 0, 1, 2 or 3,
t is 0, 1, 2 or 3,
X is C=O, CHOH or $CR^2R^3$; wherein $R^2$ and $R^3$ independently are hydrogen or $C_{1-6}$-alkyl, or X is a bond,
Y is heteroaryl
$R^4$ is
(a) $C_{3-8}$-cycloalkyl or $C_{3-8}$-cycloalkenyl, which may optionally be substituted with one or more substituents selected from $C_{1-6}$-alkyl, $C_{1-4}$-alkoxy, $C_{1-6}$-alkylthio, cyano, halo-$C_{1-6}$-alkyl, halo-$C_{1-6}$-alkoxy, and halogen, or
(b) aryl, aryl-$C_{1-6}$-alkyl, aryl-$C_{2-6}$-alkenyl, or heteroaryl which may optionally be substituted with one or more substituents selected from
halogen, nitro, cyano, acyl, hydroxy, $C_{1-6}$-alkyl, $C_{1-6}$-alkylthio, $C_{1-6}$-alkylsulfonyl, $C_{1-6}$-alkylsulfonyloxy, $C_{1-6}$-alkoxy, $C_{3-4}$-cycloalkyl, halo-$C_{1-6}$-alkyl, halo-$C_{1-6}$-alkoxy, —$NR^5R^6$, $R^5R^6N$—$C_{1-6}$-alkyl-, $R^5R^6N$—$C_{1-6}$-alkoxy- and —O(C=O)$NR^5R^6$, or wherein two substituents in adjacent positions together form a radical —O—$(CH_2)_{1-3}$—O—, wherein $R^5$ and $R^6$ independently are hydrogen, $C_{1-6}$-alkyl, $C_{3-8}$-cycloalkyl, $C_{1-6}$-alkanoyl or aryl, or $R^5$ and $R^6$ together with the nitrogen atom to which they are attached form a 3 to 7 membered, saturated or unsaturated ring, which may be fused to a benzene ring, a group of the formula
-(W)$_k$-A wherein
W is —C$_{1-6}$-alkyl-, —(O)$_l$—C$_{2-6}$-alkenyl-, —(O)$_l$—C$_{1-6}$-alkyl-O—, —(CH$_2$)$_n$—(C=O)—(CH$_2$)$_m$—, —O—
wherein
l is 0 or 1
k is 0 or 1
n and m are independently 0, 1, 2 or 3,
A is
aryl, aryl-C$_{1-6}$-alkyl, heteroaryl, heteroaryl-C$_{1-6}$-alkyl, C$_{1-6}$-alkyl or C$_{3-8}$-cycloalkyl wherein the ring moieties optionally may be substituted with one or more substituents selected from
halogen, nitro, cyano, hydroxy, C$_{1-6}$-alkylthio, C$_{1-6}$-alkylsulfonyl, C$_{1-6}$-alkylsulfonyloxy, C$_{1-6}$-alkyl, C$_{1-6}$-alkoxy, C$_{3-8}$-cycloalkyl, halo-C$_{1-6}$-alkyl, halo-C$_{1-6}$-alkoxy, —NR$^7$R$^8$, R$^7$R$^8$N—C$_{1-6}$-alkyl-, R$^7$R$^8$N—C$_{1-6}$-alkoxy- and —O(C=O)NR$^7$R$^8$, or wherein two substituents in adjacent positions together form a radical —O—(CH$_2$)$_{1-3}$—O—,
wherein R$^7$ and R$^8$ independently are hydrogen, C$_{1-6}$-alkyl, C$_{3-8}$-cycloalkyl, C$_{1-6}$-alkanoyl or aryl, or R$^7$ and R$^8$ together with the nitrogen atom to which they are attached form a 3 to 7 membered, saturated or unsaturated ring, which may be fused to a benzene ring,
NR$^9$R$^{10}$ wherein R$^9$ and R$^{10}$ independently are hydrogen, C$_{1-6}$-alkyl, C$_{3-8}$-cycloalkyl, C$_{1-6}$-alkanoyl or aryl, or R$^9$ and R$^{10}$ together with the nitrogen atom to which they are attached form a 3 to 7 membered, saturated or unsaturated ring, which may be fused to a benzene ring, and the ring may contain further heteroatoms and it may optionally be substituted with C$_{1-6}$-alkyl, C$_{3-8}$-cycloalkyl, C$_{1-6}$-alkanoyl or aryl,
as well as any diastereomer or enantiomer or tautomeric form thereof including mixtures of these or a pharmaceutically acceptable salt thereof.

Definitions

In the structural formulae given herein and throughout the present specification, the following terms have the indicated meaning:

The term "halogen" means F, Cl, Br or I.

The term "C$_{1-6}$-alkyl" as used herein represents a saturated, branched or straight hydrocarbon group having from 1 to 6 carbon atoms. Typical C$_{1-6}$-alkyl groups include, but are not limited to, methyl, ethyl, n-propyl, isopropyl, butyl, isobutyl, sec-butyl, tert-butyl, pentyl, hexyl and the like.

The term "C$_{2-6}$-alkenyl" as used herein represents a branched or straight hydrocarbon group having from 2 to 6 carbon atoms and at least one double bond. Typical C$_{2-6}$-alkenyl groups include, but are not limited to, ethenyl, 1-propenyl, 2-propenyl, isopropenyl, 1,3-butadienyl, 1-butenyl, 2-butenyl, 1-pentenyl, 2-pentenyl, 1-hexenyl, 2-hexenyl, 1-ethylprop-2-enyl, 1,1-(dimethyl)prop-2-enyl, 1-ethylbut-3-enyl, 1,1-(dimethyl)but-2-enyl, and the like.

The term "C$_{2-6}$-alkynyl" as used herein represents a branched or straight hydrocarbon group having from 2 to 6 carbon atoms and at least one triple bond. Typical C$_{2-6}$-alkynyl groups include, but are not limited to, vinyl, 1-propynyl, 2-propynyl, isopropynyl, 1,3-butadynyl, 1-butynyl, 2-butynyl, 1-pentynyl, 2-pentynyl, 1-hexynyl, 2-hexynyl, 1-ethylprop-2-ynyl, 1,1-(dimethyl)prop-2-ynyl, 1-ethylbut-3-ynyl, 1,1-(dimethyl)but-2-ynyl, and the like.

The term "C$_{1-6}$-alkoxy" as used herein refers to the radical —O—C$_{1-6}$-alkyl, wherein C$_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "C$_{1-6}$-alkylthio as used herein refers to the radical —S—C$_{1-6}$-alkyl, wherein C$_{1-6}$-alkyl represents a saturated, branched or straight hydrocarbon groups having from 1 to 6 carbon atoms as defined above. Representative examples are methylthio, ethylthio, propylthio, butylthio, pentylthio, hexylthio, and the like The term "halo-C$_{1-6}$-alkyl" as used herein refers to C$_{1-6}$-alkyl as above, substituted one or more times with halogen as defined above. Representative examples are trifluoromethyl and 2,2,2-trifluoroethyl.

The term "halo-C$_{1-6}$-alkoxy" as used herein refers to C$_{1-6}$-alkyl as above, substituted one or more times with halogen as defined above. Representative examples are trifluoro-methoxy and 2,2,2-trifluoroethoxy.

The term "C$_{1-6}$-alkylsulfonyl" as used herein refers to the radical —S(=O)$_2$—C$_{1-6}$-alkyl, wherein C$_{1-6}$-alkyl represents a saturated, branched or straight hydrocarbon groups having from 1 to 6 carbon atoms as defined above. Representative examples are methylsulfonyl, ethylsulfonyl, propylsulfonyl, butylsulfonyl, pentylsulfonyl, hexylsulfonyl, and the like.

The term "C$_{1-6}$-alkylsulfinyl" as used herein refers to the radical —S(=O)—C$_{1-6}$-alkyl, wherein C$_{1-6}$-alkyl represents a saturated, branched or straight hydrocarbon groups having from 1 to 6 carbon atoms as defined above. Representative examples are methylsulfinyl, ethylsulfinyl, propylsulfinyl, butylsulfinyl, pentylsulfinyl, hexylsulfinyl, and the like.

The term "C$_{3-8}$-cycloalkyl" as used herein represents a monocyclic, carbocyclic group having from from 3 to 8 carbon atoms. Representative examples are cyclopropyl, cyclobutyl, cyclopentyl, cyclohexyl, cycloheptyl, cyclooctyl, and the like.

The term "C$_{3-8}$-cycloalkenyl" as used herein represents a monocyclic, carbocyclic, non-aromatic group having from 3 to 8 carbon atoms and at least one double bond. Representative examples are cyclopropenyl, cyclobutenyl, cyclopentenyl, cyclohexenyl, cycloheptenyl, cyclooctenyl and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, benzothiophenyl (thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

The term heteroaryl-$C_{1-6}$-alkyl as used herein denotes heteroaryl as defined above and $C_{1-6}$-alkyl as defined above.

The terms "aryl-$C_{1-6}$-alkyl" and "aryl-$C_{2-6}$-alkenyl" as used herein denotes aryl as defined above and $C_{1-6}$-alkyl and $C_{2-6}$-alkenyl, respectively, as defined above.

The term "acyl" as used herein denotes —(C=O)—$C_{1-6}$-alkyl wherein $C_{1-6}$-alkyl is as defined above.

The term "$NR^xR^y$", wherein $R^x$ and $R^y$ together with the nitrogen atom to which they are attached form a 3 to 7 membered, saturated or unsaturated ring, which may optionally be fused to a benzene ring" as used herein denotes for example aziridinyl, azetidinyl, pyrrolidinyl, pyrrolyl, piperidinyl, tetrahydropyridyl, homopiperidinyl, indolyl, indolinyl, 1,2,3,4-tetrahydroquinolinyl, 1,2,3,4-tetrahydroisoquinolinyl, isoindolyl and the like. The term also mentions the possibility of the presence of further heteroatoms, which denotes for example pyrazolyl, piperazinyl, imidazolyl, imidazolidinyl, morpholinyl, benzimidazolyl, indazolyl and the like.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

DESCRIPTION OF THE INVENTION

In one embodiment of the invention $R^1$ is $C_{3-8}$-cycloalkyl or $C_{1-6}$alkyl.

In another embodiment of the invention X is a bond.

In another embodiment of the invention s and t together are 0, 1, 2 or 3.

In another embodiment of the invention Y is a 5- or 6-membered heterocyclic aromatic ring system.

In another embodiment of the invention Y is a 5-membered heterocyclic aromatic ring system.

In another embodiment of the invention Y is a 5-membered heterocyclic aromatic ring system containing 1, 2 or 3 heteroatoms.

In another embodiment of the invention Y is a 5-membered heterocyclic aromatic system containing 3 heteroatoms.

In another embodiment of the invention Y is selected from the group consisting of oxadiazolyl, thiadiazolyl, triazolyl.

In another embodiment of the invention Y is selected from

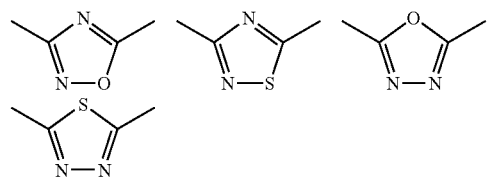

In another embodiment of the invention $R^4$ is aryl.

In another embodiment of the invention $R^4$ is phenyl;

In another embodiment of the invention $R^4$ is substituted with $(W)_k$-A

In another embodiment of the invention K is 0;

In another embodiment of the invention A is aryl;

In another embodiment of the invention A is phenyl;

In another embodiment of the invention W represents C=O, —O— or $C_{1-6}$-alkyl

In a different aspect, the invention provides compounds of Formula II

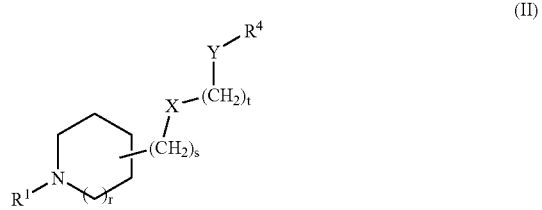

wherein $R^1$ is $C_{1-6}$-alkyl, $C_{2-6}$-alkenyl, $C_{2-6}$-alkynyl,
which may optionally be substituted with one or more substituents independently selected from $R^{11}$, wherein $R^{11}$ is halogen, $C_{1-6}$-alkoxy or hydroxy, $C_{3-8}$-cycloalkyl, $C_{5-8}$-cycloalkenyl, $C_{3-8}$-cycloalkyl-$C_{1-6}$-alkyl, di($C_{3-8}$-cycloalkyl)-$C_{1-6}$-alkyl, $C_{3-8}$-cycloalkyl-$C_{2-6}$-alkenyl, $C_{3-8}$-cycloalkyl-$C_{2-6}$-alkynyl, $C_{5-8}$-cycloalkenyl-$C_{1-6}$-alkyl, $C_{5-8}$-cycloalkenyl-$C_{2-6}$-alkenyl, $C_{5-8}$-cycloalkenyl-$C_{2-6}$-alkynyl, 4-pyridyl or tetrahydropyranyl,
wherein the cyclic moieties may optionally be substituted with one or more substituents independently selected from $R^{12}$, wherein $R^{12}$ is $C_{1-6}$-alkyl, halogen, trifluoromethyl or 2,2,2-trifluoroethyl, r is 0, 1 or 2, s is 0, 1, 2 or 3, t is 0, 1, 2 or 3, X is C=O, CHOH or $CR^2R^3$; wherein $R^2$ and $R^3$ independently are hydrogen or $C_{1-6}$-alkyl, or X is a bond, Y is heteroaryl optionally substituted with one or more substituents independently selected from $R^{18}$, $R^{18}$ is halogen, nitro, cyano, hydroxy, $C_{1-6}$-alkyl, $C_{1-6}$-alkylthio or $C_{1-6}$-alkoxy.

$R^4$ is (a) $C_{1-6}$-alkyl, $C_{3-8}$-cycloalkyl or $C_{3-8}$-cycloalkenyl, which may optionally be substituted with one or more substituents independently selected from $R^{13}$, wherein $R^{13}$ is $C_{3-8}$-cycloalkyl, $C_{1-6}$-alkoxy, $C_{1-6}$-alkylthio, cyano, halo-$C_{1-6}$-alkyl, halo-$C_{1-6}$-alkoxy, and halogen, or (b) aryl, aryl-$C_{1-6}$-alkyl, aryl-$C_{2-6}$-alkenyl, or heteroaryl which may optionally be substituted with one or more substituents independently selected from $R^{14}$ $R^{14}$ is halogen, nitro, cyano, acyl, hydroxy, $C_{1-6}$-alkyl, $C_{1-6}$-alkylthio, $C_{1-6}$-alkylsulfonyl, $C_{1-6}$-alkylsulfonyloxy, $C_{1-6}$-alkoxy, $C_{3-8}$-cycloalkyl, halo-$C_{1-6}$-alkyl, halo-$C_{1-6}$-alkoxy, —$NR^5R^6$, $R^5R^6N$—$C_{1-6}$-alkyl-, $R^5R^6N$—$C_{1-6}$-alkoxy-, or —$O(C=O)NR^5R^6$, or wherein two substituents in adjacent positions together form a radical —O—$(CH_2)_{1-3}$—O—, wherein $R^5$ and $R^6$ independently are hydrogen, $C_{1-6}$-alkyl, $C_{3-8}$-cycloalkyl, $C_{1-6}$-alkanoyl or aryl, or $R^5$ and $R^6$ together with the nitrogen atom to which they are attached form a 3 to 7 membered, saturated or unsaturated ring, which may be fused to a benzene ring, a group of the formula -(W)$_k$-A wherein W is —$C_{1-6}$alkyl-, —(O)$_l$—$C_{2-6}$-alkenyl-, —(O)$_l$—$C_{1-6}$-alkyl-O—, —$(CH_2)_n$—(C=O)—$(CH_2)_m$—, —O— wherein l is 0 or 1 k is 0 or 1 n and m are independently 0, 1, 2 or 3,

A is aryl, aryl-$C_{1-6}$-alkyl, heteroaryl, heteroaryl-$C_{1-6}$-alkyl, $C_{1-6}$-alkyl or $C_{3-8}$-cycloalkyl wherein the ring moieties optionally may be substituted with one or more substituents independently selected from $R^{15}$ $R^{15}$ is halogen, nitro, cyano, hydroxy, $C_{1-6}$-alkylthio, $C_{1-6}$-alkylsulfonyl, $C_{1-6}$-alkylsulfonyloxy, $C_{1-6}$-alkyl, $C_{1-6}$-alkoxy, $C_{3-8}$-cycloalkyl, halo-$C_{1-6}$-alkyl, halo-$C_{1-6}$-alkoxy, —$NR^7R^8$, $R^7R^8N$—$C_{1-6}$-alkyl-, $R^7R^8N$—$C_{1-6}$-alkoxy-, or —$O(C=O)NR^7R^8$, or wherein two substituents in adjacent positions together form a radical —O—$(CH_2)_{1-3}$—O—, wherein $R^7$ and $R^8$ independently are hydrogen, $C_{1-6}$-alkyl, $C_{3-8}$-cycloalkyl, $C_{1-6}$-alkanoyl or aryl, or $R^7$ and $R^8$ together with the nitrogen atom to which they are attached form a 3 to 7 membered, saturated or unsaturated ring, which may be fused to a benzene ring, $NR^9R^{10}$ wherein $R^9$ and $R^{10}$ independently are hydrogen, $C_{1-6}$-alkyl, $C_{3-8}$-cycloalkyl, $C_{1-6}$-alkanoyl or aryl, or $R^9$ and $R^{10}$ together with the nitrogen atom to which they are attached form a 3 to 7 membered, saturated or unsaturated ring, which may be fused to a benzene ring, and the ring may contain further heteroatoms and it may optionally be substituted with one or more substituents independently selected from $R^{16}$, wherein $R^{16}$ is $C_{1-6}$-alkyl, $C_{3-8}$-cycloalkyl, $C_{1-6}$-alkanoyl or aryl optionally substituted with one or more substituents independently selected from $R^{17}$, wherein $R^{17}$ is halogen, nitro, cyano, hydroxy, or $C_{1-6}$-alkyl;

as well as any diastereomer or enantiomer or tautomeric form thereof including mixtures of these or a pharmaceutically acceptable salt thereof.

In one embodiment hereof $R^1$ is $C_{3-8}$-cycloalkyl or $C_{1-6}$alkyl.

In another embodiment hereof $R^1$ is cyclopropyl, cyclobutyl, cyclopentyl, cyclohexyl, methyl, ethyl, propyl, 1-methylpropyl, 1-ethyl-propyl, isopropyl, or tert-butyl.

In another embodiment hereof $R^1$ is cyclopropyl, cyclopentyl, 1-ethyl-propyl, or isopropyl.

In another embodiment hereof $R^1$ is isopropyl.

In another embodiment hereof $R^1$ is cyclopropyl.

In another embodiment hereof X is a bond.

In another embodiment hereof s and t together are 0, 1, 2 or 3.

In another embodiment hereof r is 1.

In another embodiment hereof s is 0 or 1.

In another embodiment hereof s is 0.

In another embodiment hereof t is 0.

In another embodiment hereof Y is a 5- or 6-membered heterocyclic aromatic ring system optionally substituted with one or more substituents independently selected from $R^{18}$.

In another embodiment hereof Y is a 5-membered heterocyclic aromatic ring system optionally substituted with one or more substituents independently selected from $R^{18}$.

In another embodiment hereof Y is a 5-membered heterocyclic aromatic ring system containing 1, 2 or 3 heteroatoms, optionally substituted with one or more substituents independently selected from $R^{18}$.

In another embodiment hereof Y is a 5-membered heterocyclic aromatic system containing 3 heteroatoms, optionally substituted with one or more substituents independently selected from $R^{18}$.

In another embodiment hereof Y is selected from the group consisting of oxadiazolyl, thiadiazolyl, or triazolyl, optionally substituted with one or more substituents independently selected from $R^{18}$.

In another embodiment hereof Y is selected from

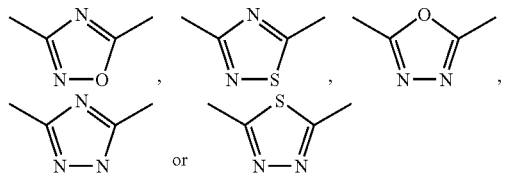

In another embodiment hereof $R^4$ is aryl, aryl-$C_{1-6}$-alkyl, either of which may optionally be substituted with one or more substituents independently selected from $R^{14}$, or $C_{3-8}$-cycloalkyl optionally substituted with one or more substituents independently selected from $R^{13}$.

In another embodiment hereof $R^4$ is aryl optionally substituted with one or more substituents independently selected from $R^{14}$.

In another embodiment hereof $R^4$ is phenyl, biphenylyl, or naphthyl optionally substituted with one or more substituents independently selected from $R^{14}$.

In another embodiment hereof $R^4$ is phenyl optionally substituted with one or more substituents independently selected from $R^{14}$.

In another embodiment hereof $R^{13}$ is $C_{1-6}$-alkyl.

In another embodiment hereof $R^{14}$ is halogen, cyano, hydroxy, $C_{1-6}$-alkyl, $C_{1-6}$-alkylsulfonyl, $C_{1-6}$-alkylsulfonyloxy, $C_{1-6}$-alkoxy, $C_{3-8}$-cycloalkyl, —$CF_3$, —$OCF_3$, —$NR^5R^6$, $R^5R^6N$—$C_{1-6}$-alkyl-, or a group of the formula -(W)$_k$-A.

In another embodiment hereof $R^{14}$ is

F, Cl, cyano, methyl, ethyl, propyl, butyl, tert-butyl, methyl-sulfonyl, methylsulfonyloxy, methoxy, ethoxy, cyclopropyl, cyclobutyl, cyclopentyl, cyclohexyl, —$CF_3$, —$OCF_3$, —$NR^5R^6$, $R^5R^6N$-methyl-, or a group of the formula -(W)$_k$-A.

In another embodiment hereof R$^{14}$ is
F, Cl, cyano, methyl, tert-butyl, methyl-sulfonyl, methoxy, cyclopentyl, cyclohexyl, —CF$_3$, —OCF$_3$, —NR$^5$R$^6$, R$^5$R$^6$N-methyl-, or a group of the formula -(W)$_k$-A.

In another embodiment hereof R$^{14}$ is a group of the formula -(W)$_k$-A.

In another embodiment hereof k is 1;

In another embodiment hereof k is 0.

In another embodiment hereof W is —C$_{1-6}$-alkyl-, —(O)$_l$—C$_{1-6}$-alkyl-O—, —(CH$_2$)$_n$—(C=O)—(CH$_2$)$_m$—, or —O—.

In another embodiment hereof W is —C$_{1-6}$-alkyl- or —(CH$_2$)$_n$—(C=O)—(CH$_2$)$_m$—.

In another embodiment hereof W is methylene, ethylene, propylene or —(CH$_2$)$_n$—(C=O)—(CH$_2$)$_m$—.

In another embodiment hereof n is 0 or 1.

In another embodiment hereof n is 0.

In another embodiment hereof m is 0 or 1.

In another embodiment hereof m is 0.

In another embodiment hereof l is 0.

In another embodiment hereof A is C$_{1-6}$-alkyl, aryl or C$_{3-8}$-cycloalkyl, wherein the ring moieties optionally may be substituted with one or more substituents independently selected from R$^{15}$, or A is NR$^9$R$^{10}$.

In another embodiment hereof A is methyl, ethyl, phenyl, cyclopropyl, cyclobutyl, cyclopentyl, or cyclohexyl, wherein the ring moieties optionally may be substituted with one or more substituents independently selected from R$^{15}$, or A is NR$^9$R$^{10}$.

In another embodiment hereof A is phenyl optionally substituted with one or more substituents independently selected from R$^{15}$.

In another embodiment hereof A is phenyl.

In another embodiment hereof A is NR$^9$R$^{10}$.

In another embodiment hereof R$^{15}$ is
halogen, nitro, cyano, hydroxy, C$_{1-6}$-alkylthio, C$_{1-6}$-alkylsulfonyl, C$_{1-6}$-alkylsulfonyloxy, C$_{1-6}$-alkyl, C$_{1-6}$-alkoxy, C$_{3-8}$-cycloalkyl, halo-C$_{1-6}$-alkyl, or halo-C$_{1-6}$-alkoxy.

In another embodiment hereof R$^{15}$ is halogen, cyano, hydroxy, CH$_3$—S—, CH$_3$CH$_2$—S—, methylsulfonyl, methylsulfonyloxy, methyl, ethyl, propyl, butyl, isopropyl, methoxy, ethoxy, cyclopropyl, cyclobutyl, cyclopentyl, or cyclohexyl, —CF$_3$, or —OCF$_3$.

In another embodiment hereof R$^{15}$ is halogen, methyl, ethyl, methoxy, ethoxy, —CF$_3$, or —OCF$_3$.

In another embodiment hereof R$^9$ and R$^{10}$ together with the nitrogen atom to which they are attached form a 3 to 7 membered, saturated or unsaturated ring, which may be fused to a benzene ring, and the ring may contain further heteroatoms and it may optionally be substituted with one or more substituents independently selected from R$^{16}$.

In another embodiment hereof R$^9$ and R$^{10}$ together with the nitrogen atom to which they are attached form a structure selected from

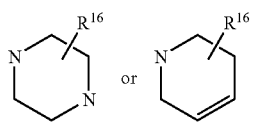

In another embodiment hereof R$^{16}$ is methyl, ethyl, 1-ethyl-propyl or phenyl optionally substituted with one or more substituents independently selected from R$^{17}$.

In another embodiment hereof R$^{17}$ is halogen.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates, which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds of the present invention interact with the histamine H3 receptor and are accordingly useful for the treatment of a wide variety of conditions and disorders in which histamine H3 receptor interactions are beneficial.

Accordingly, in another aspect the present invention relates to a compound of the general formula (I) as well as any diastereomer or enantiomer or tautomeric form thereof including mixtures of these or a pharmaceutically acceptable salt thereof for use as a pharmaceutical composition.

The invention also relates to pharmaceutical compositions comprising, as an active ingredient, at least one compound of the formula (I) or any diastereomer or enantiomer or tautomeric form thereof including mixtures of these or a pharmaceutically acceptable salt thereof together with one or more pharmaceutically acceptable carriers or diluents.

Furthermore, the invention relates to the use of a compound of the general formula (I) as well as any diastereomer or enantiomer or tautomeric form thereof including mixtures of these or a pharmaceutically acceptable salt thereof for the preparation of a pharmaceutical composition for the treatment of disorders and diseases related to the histamine H3 receptor.

In still another aspect, the invention relates to a method for the treatment of diseases and disorders related to the histamine H3 receptor the method comprising administering to a subject in need thereof an effective amount of a compound of the formula (I) or any diastereomer or enantiomer or tautomeric form thereof including mixtures of these or a pharmaceutically acceptable salt thereof or a pharmaceutical composition comprising the same.

In one aspect the invention relates to compounds with histamine H3 receptor antagonistic activity or inverse agonistic activity which may accordingly be useful in the treatment of a wide range of conditions and disorders in which histamine H3 receptor blockade is beneficial.

In another aspect the invention relates to compounds with histamine H3 receptor agonistic activity and which may accordingly be useful in the treatment of a wide range of conditions and disorders in which histamine H3 receptor activation is beneficial.

In a preferred embodiment of the invention the present compounds are used for the preparation of a pharmaceutical composition for the reduction of weight.

In a preferred embodiment of the invention the present compounds are used for the preparation of a pharmaceutical composition for the treatment of overweight or obesity.

In another preferred embodiment of the invention the present compounds are used for the preparation of a pharmaceutical composition for the suppression of appetite or satiety induction.

In a further preferred embodiment of the invention the present compounds are used for the preparation of a pharmaceutical composition for the prevention and/or treatment of disorders and diseases related to overweight or obesity such as atherosclerosis, hypertension, IGT (impaired glucose tolerance), diabetes, especially type 2 diabetes (NIDDM (non-insulin dependent diabetes mellitus)), dyslipidaemia, coronary heart disease, gallbladder disease, osteoarthritis and various types of cancer such as endometrial, breast, prostate and colon cancers.

In yet a further preferred embodiment of the invention the present compounds are used for the preparation of a pharmaceutical composition for the prevention and/or treatment of eating disorders such as bulimia and binge eating.

In a further preferred embodiment of the invention the present compounds are used for the preparation of a pharmaceutical composition for the treatment of IGT.

In a further preferred embodiment of the invention the present compounds are used for the preparation of a pharmaceutical composition for the treatment of type 2 diabetes. Such treatment includes inter alia treatment for the purpose of delaying or prevention of the progression from IGT to type 2 diabetes as well as delaying or prevention of the progression from non-insulin requiring type 2 diabetes to insulin requiring type 2 diabetes.

The compounds of the present invention may also be used for the treatment of air-way disorders such as asthma, as anti-diarrhoeals and for the modulation of gastric acid secretion.

Furthermore, the compounds of the present invention may be used for the treatment of diseases associated with the regulation of sleep and wakefulness and for the treatment of narcolepsy and attention deficit disorder.

Moreover, the compounds of the invention may be used as CNS stimulants or as sedatives.

The present compounds may also be used for the treatment of conditions associated with epilepsy. Additionally, the present compounds may be used for the treatment of motion sickness and vertigo. Furthermore, they may be useful as regulators of hypothalamo-hypophyseal secretion, antidepressants, modulators of cerebral circulation, and in the treatment of irritable bowel syndrome.

Further, the compounds of the present invention may be used for the treatment of dementia and Alzheimer's disease.

The compounds of the present invention may also be useful for the treatment of allergic rhinitis, ulcer or anorexia.

The compounds of the present invention may furthermore be useful for the treatment of migraine, see McLeod et al., *The Journal of Pharmacology and Experimental Therapeutics* 287 (1998), 43-50, and for the treatment of myocardial infarction, see Mackins et al., *Expert Opinion on Investigational Drugs* 9 (2000), 2537-2542.

In a further aspect of the invention treatment of a patient with the present compounds is combined with diet and/or exercise.

In a further aspect of the invention the present compounds are administered in combination with one or more further active substances in any suitable ratio(s). Such further active agents may be selected from antiobesity agents, antidiabetics, antidyslipidemic agents, antihypertensive agents, agents for the treatment of complications resulting from or associated with diabetes and agents for the treatment of complications and disorders resulting from or associated with obesity.

Thus, in a further aspect of the invention the present compounds are administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

In yet another embodiment the antiobesity agent is growth hormone, a growth factor such as prolactin or placental lactogen, or a growth hormone releasing compound.

In yet a further aspect the present compounds are administered in combination with one or more antidiabetic agents.

Relevant antidiabetic agents include insulin, insulin analogues and derivatives such as those disclosed in EP 0 792 290 (Novo Nordisk A/S), eg $N^{\epsilon B29}$-tetradecanoyl des (B30) human insulin, EP 0 214 826 and EP 0 705 275 (Novo Nordisk A/S), eg $Asp^{B28}$ human insulin, U.S. Pat. No. 5,504,188 (Eli Lilly), eg $Lys^{B28}$ $Pro^{B29}$ human insulin, EP 0 368 187 (Aventis), eg Lantus®, which are all incorporated herein by reference, GLP-1 derivatives such as those disclosed in WO 98/08871 (Novo Nordisk A/S), which is incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulfonylurea eg tolbutamide, chlorpropamide, tolazamide, glibenclamide, glipizide, glimepiride, gliclazide or glyburide.

In another embodiment of the invention the present compounds are administered in combination with a biguanide eg metformin.

In yet another embodiment of the invention the present compounds are administered in combination with a meglitinide eg repaglinide or nateglinide.

In still another embodiment of the invention the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg voglibose, emiglitate, miglitol or acarbose.

In another embodiment of the invention the present compounds are administered in combination with an agent acting on the ATP-dependent potassium channel of the β-cells eg tolbutamide, glibenclamide, glipizide, gliclazide, BTS-67582 or repaglinide.

In yet another embodiment of the invention the present compounds may be administered in combination with nateglinide.

In still another embodiment, the present compounds are administered in combination with an antihyperlipidemic agent or antilipidemic agent, eg cholestyramine, colestipol, clofibrate, gemfibrozil, lovastatin, pravastatin, simvastatin, probucol or dextrothyroxine.

In still another embodiment of the invention the present compounds are administered in combination with an antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulfonylurea such as glyburide; a sulfonylurea and acarbose; nateglinide and metformin; acarbose and metformin; a sufonylurea, metformin and troglitazone; insulin and a sulfonylurea; insulin and metformin; insulin, metformin and a sulfonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

A typical tablet, which may be prepared by conventional tabletting techniques, may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

In the examples the following terms are intended to have the following, general meanings:

NMR spectra were recorded on Bruker 300 MHz and 400 MHz instruments. HPLC-MS was performed on a Perkin Elmer instrument (API 100), and HPLC-systems from Merck-Hitachi or Waters. HPLC system: Hibar™ RT 250-4, Lichrosorb™ RP-18, 5.0 µm, 4.0×250 mm; gradient elution, 20% to 80% solvent B (0.1% TFA in acetonitrile) in solvent A (0.1% TFA in water) within 30 min, 1.0 mL/min, detection at 214 nm, temperature 30° C.

The preparation of the compounds of this invention can be realised in many different ways. The starting derivatives are either known compounds or compounds that may be prepared by a person skilled in the art in analogy with the preparation of similar known compounds or by the General procedures A through F described herein.

General Procedure (A)

Compounds of the formula (Ia) according to the invention wherein X is a bond or $CR^2R^3$ and r, s, t, $R^1$, $R^2$, $R^3$ and $R^4$ are as defined for formula (I) can be prepared as outlined below:

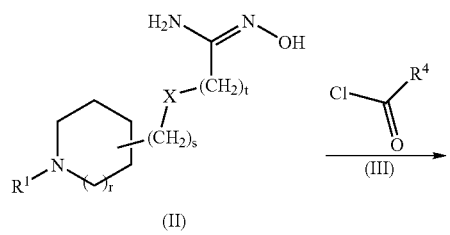

(II)

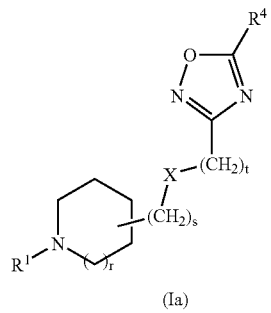

(Ia)

A N-hydroxyamidine of formula (II) wherein X is a bond or $CR^2R^3$ and r, s, t, $R^1$, $R^2$ and $R^3$ are as defined above may be reacted with an activated carboxylic acid of the formula (III) wherein $R^4$ is as defined above. This reaction may be carried out in a suitable solvent like eg acetic acid at a temperature of up to reflux.

General Procedure (B)

Compounds of the formula (Ib) according to the invention wherein $R^4$ is aryl, aryl-$C_{1-6}$-alkyl or heteroaryl substituted with W-A wherein W is —$C_{1-6}$-alkyl- or —O—$C_{1-6}$-alkyl-, and A is $NR^9R^{10}$, X is a bond or $CR^2R^3$ and r, s, t, $R^1$, $R^2$, $R^3$, $R^9$ and $R^{10}$ are as defined for formula (I) can be prepared as outlined below:

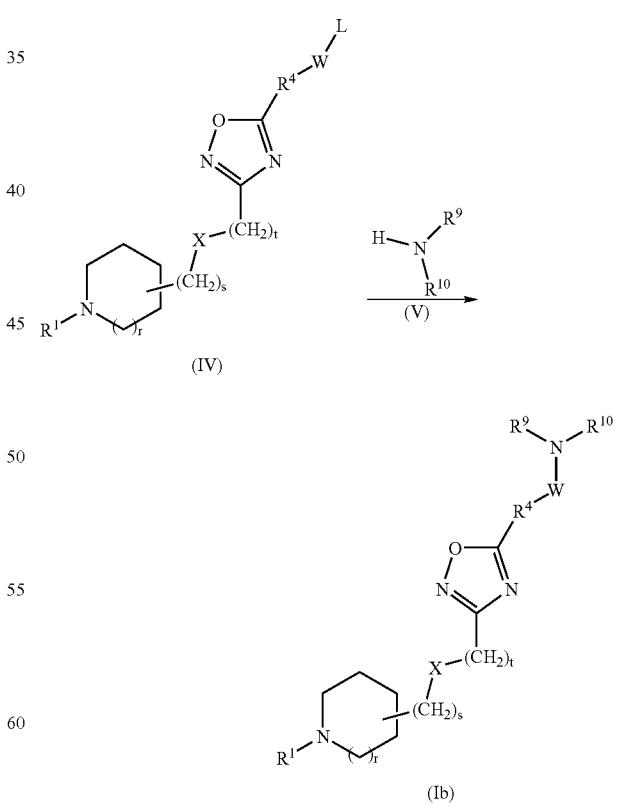

A compound of formula (IV) wherein X is a bond or $CR^2R^3$ and r, s, t, $R^1$, $R^2$, $R^3$ and $R^4$ are as defined above and wherein L represents a suitable leaving group such as eg. halogen or mesylate may be reacted with an amine of the formula (V) wherein $R^9$ and $R^{10}$ are as defined above. This reaction may be carried out in a suitable solvent like eg ethanol or neat at a temperature of up to reflux. This substitution reaction may be carried out in the presence of a base like eg. potassium carbonate or excess of the amine of formula (V).

General Procedure (C)

Compounds of the formula (Ic) according to the invention wherein $R^4$ is aryl, aryl-$C_{1-6}$-alkyl or heteroaryl, W' is —O—($C_{1-3}$-alkyl)- or —$C_{1-6}$-alkyl-, X is a bond or $CR^2R^3$, A is aryl or heteroaryl and r, s, t, $R^1$, $R^2$ and $R^3$ are as defined for formula (I) can be prepared as outlined below:

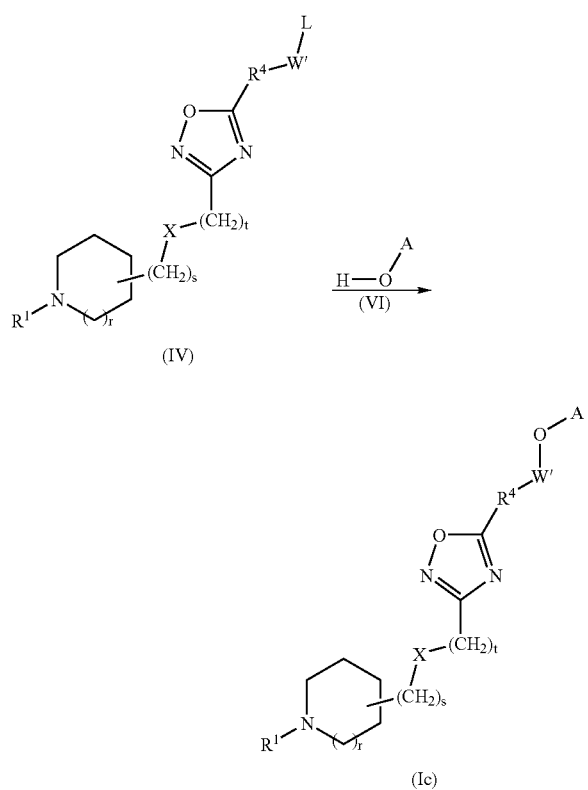

A compound of formula (IV) wherein X is a bond or $CR^2R^3$ and r, s, t, W', $R^1$, $R^2$ and $R^3$ are as defined above, and wherein L represents a suitable leaving group such as eg. halogen or mesylate may be reacted with an alcohol of the formula (VI) wherein A is aryl or alkyl. This reaction may be carried out in a suitable solvent like eg. THF at a temperature of up to reflux. This substitution reaction may be carried out in the presence of a base like eg. potassium tert-butoxide.

General Procedure (D)

Compounds of the formula (Id) according to the invention wherein X is a bond or $CR^2R^3$ and r, s, t, $R^1$, $R^2$, $R^3$ and $R^4$ are as defined for formula (I) can be prepared as outlined below:

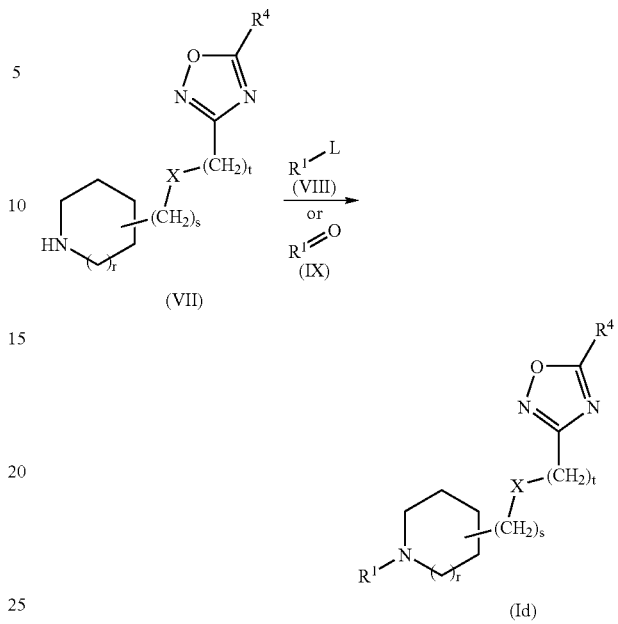

A compound of formula (VII) wherein X is a bond or $CR^2R^3$ and r, s, t, $R^2$, $R^3$ and $R^4$ are as defined above may be alkylated with a compound of formula (VIII) wherein L represents a suitable leaving group such as eg. halogen or mesylate and $R^1$ is as defined above. This reaction may be carried out in a suitable solvent like eg dichloromethane at a temperature of up to reflux. This substitution reaction may be carried out in the presence of a base like eg. potassium carbonate.

Alternatively, a compound of formula (VII) may be alkylated with a carbonyl compound of formula (IX), wherein $R^1$ is as defined above, under reducing conditions. This reaction may be carried out in a suitable solvent like eg an alcohol at a temperature of up to reflux. This reductive alkylation reaction may be carried out in the presence of a reducing agent like eg sodium cyanoborohydride and an acid like eg acetic acid.

General Procedure (E)

Compounds of the formula (Ie) according to the invention wherein $R^4$ is aryl, aryl-$C_{1-6}$-alkyl or heteroaryl substituted with W-A wherein W is >C=O, X is a bond or $CR^2R^3$ and A, r, s, t, $R^1$, $R^2$, $R^3$, $R^9$ and $R^{10}$ are as defined for formula (I) can be prepared as outlined below:

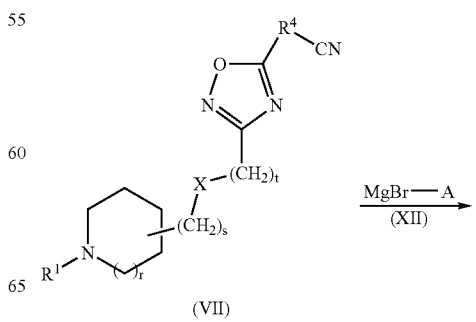

-continued

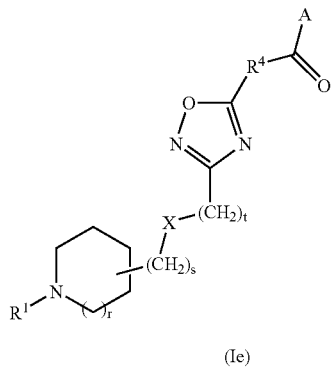

(Ie)

A compound of formula (XI) wherein X is a bond or $CR^2R^3$ and r, s, t, $R^1$, $R^2$ and $R^3$ are as defined above and wherein $R^4$ is substituted with a cyano group may be reacted with an organometallic compound such as a Grignard reagent of the formula (XII) wherein A is as defined above. This reaction may be carried out in a suitable solvent like eg tetrahydrofuran at a temperature of up to reflux.

General Procedure (F)

Compounds of the formula (If) according to the invention wherein X is a bond or $CR^2R^3$ and r, s, t, $R^1$, $R^2$, $R^3$ and $R^4$ are as defined for formula (I) can be prepared as outlined below:

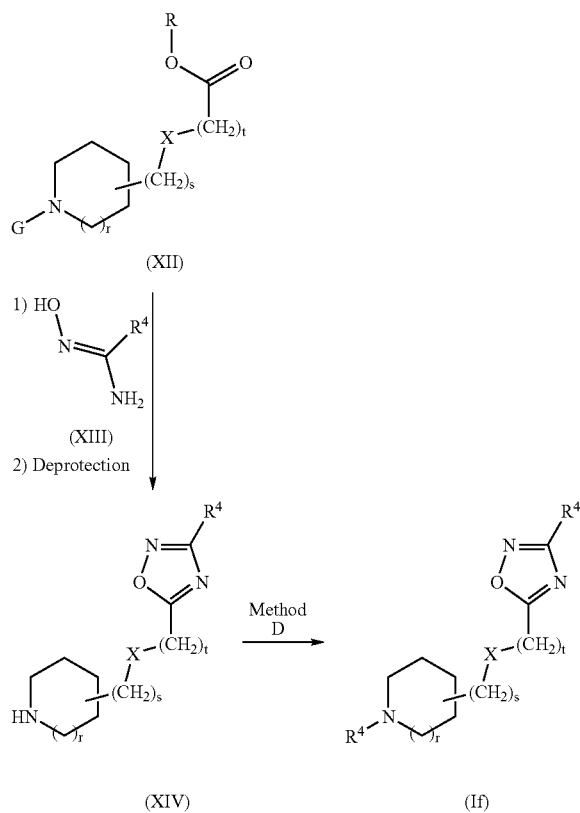

A compound of formula (XII) wherein X is a bond or $CR^2R^3$ and r, s, t, $R^2$ and $R^3$ are as defined above and wherein R represents a lower alkyl residue and G represents an appropriate protection group such as eg tert-butoxycarbonyl may be reacted with a N-hydroxycarboxamidine of formula (XIII) wherein $R^4$ is as defined above. This reaction may be carried out in the presence of a base like e.g. potassium tert-butoxide or sodium ethoxide in a suitable solvent, e.g. ethanol at a temperature of up to reflux.

Following the above condensation to form the heterocycle, deprotection may be carried out by standard conditions depending on the protection group used, to give the amine derivative of formula (XIV). This amine of formula (XIV) may then be reacted further by the Method D described above to give compounds of formula (If).

Example 1 (General Procedure (A))

1-Cyclopentyl-4-{2-[5-(4-methanesulfonylphenyl)[1,2,4]oxadiazol-3-yl]ethyl}piperidine, hydrochloride

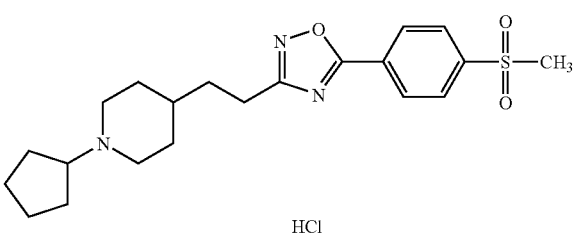

HCl

Step A:

4-(2-Hydroxyethyl)piperidine-1-carboxylic acid tert-butyl ester

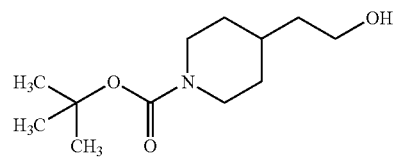

To a solution of 2-(piperidin-4-yl)ethanol (5.0 g, 39 mmol) in THF (60 mL) was added 1 N NaOH (60 mL). Di-tert-butyl dicarbonate (9.5 g, 44 mmol) was added and the mixture was stirred vigorously overnight. Ethyl acetate (100 mL) was added and the mixture was stirred vigorously. The phases were separated and the organic phase was washed with water and then dried ($MgSO_4$). The mixture was filtered and the solvent was evaporated to give 9.5 g of 4-(2-hydroxyethyl)piperidine-1-carboxylic acid tert-butyl ester.

$^1$H NMR (400 MHz, $CDCl_3$) δ 1.05-1.18 (m, 2H), 1.45 (s, 9H), 1.53 (q, 2H), 1.57-1.63 (m, 1H), 1.65-1.72 (m, 2H), 1.74 (t, 1H), 2.63-2.76 (m, 2H), 3.70 (q, 2H), 4.02-4.12 (m, 2H). HPLC: Rt=15.31 min.

Step B:

4-(2-Cyanoethyl)piperidine-1-carboxylic acid tert-butyl ester

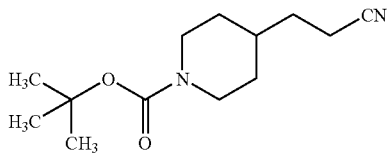

To the above boc-protected piperidine (9.0 g, 39 mmol) dissolved in ethyl acetate (150 mL) was added triethylamine (6.0 g, 59 mmol) followed by dropwise addition of a solution of methanesulfonyl chloride (4.7 g, 41 mmol) in ethyl acetate (20 mL). When addition was complete the mixture was stirred overnight. The mixture was filtered and the solvent was evaporated to give 13 g of crude 4-(2-methanesulfonyloxyethyl)piperidine-1-carboxylic acid tert-butyl ester which was dissolved in absolute ethanol (200 mL). Potassium cyanide (5.1 g, 78.5 mmol) and potassium iodide (0.5 g) was added and the mixture was heated at reflux with vigorous stirring for 5 h. The reaction mixture was allowed to cool to ambient temperature, filtered and the solvent was evaporated. The oily residue was dissolved in ethyl acetate (100 mL) and the organic solution was washed with water (2×10 mL) and brine. The organic solution was dried (MgSO$_4$) and the solvent was evaporated to give 9.5 g of 4-(2-cyanoethyl)piperidine-1-carboxylic acid tert-butyl ester.

$^1$H NMR (400 MHz, CDCl$_3$) δ 1.05-1.17 (m, 2H), 1.45 (s, 9H), 1.55-1.72 (m, 5H), 2.38 (t, 2H), 2.64-2.75 (m, 2H), 4.04-4.17 (m, 2H).

Step C:

3-(1-Cyclopentylpiperidin-4-yl)-N-hydroxypropionamidine

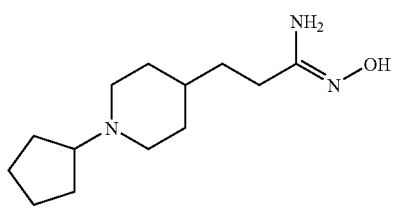

The above nitril (5.0 g, 21 mmol) was dissolved in dichloromethane (50 mL) and trifluoroacetic acid (25 mL) was added. The mixture was stirred for 45 min at ambient temperature and then the solvent was evaporated. The oily residue was dissolved in acetonitrile (100 mL) and with stirring, potassium carbonate (25 g, 180 mmol) was cautiously added. Cyclopentylbromide (15.6 g, 105 mmol) was added and the reaction mixture was stirred at reflux temperature overnight. The mixture was allowed to cool, then filtered and the solvent evaporated. The residue was dissolved in ethyl acetate (150 mL) and the organic phase was washed with water (20 mL). The aqueous washing was extracted with ethyl acetate (50 mL) and the combined organic phases were dried (MgSO$_4$). The solvent was evaporated and the residue was re-evaporated with ethanol, finally at around 50° C. This afforded 6.0 g of 3-(1-cyclopentylpiperidin-4-yl)propionitrile.

The above nitrile (4.3 g, 21 mmol) was dissolved in absolute ethanol (60 mL) and to the stirred mixture was added hydroxylamine hydrochloride (4.2 g, 60.5 mmol), water (10 mL) and potassium carbonate (8.5 g, 61.5 mmol). The reaction mixture was heated overnight at reflux. The mixture was allowed to cool and then concentrated in vacuo. The residue was stirred with a mixture of water (30 mL) and ethyl acetate (200 mL), heated and then allowed to cool again. The phases were separated and the aqueous phase was extracted with ethyl acetate (50 mL). The combined organic extracts were dried (MgSO$_4$) and the solvent was evaporated. The solid residue was stirred with diethyl ether (100 mL), isolated and dried in vacuo. This afforded 2.55 g of 3-(1-cyclopentylpiperidin-4-yl)-N-hydroxypropionamidine.

$^1$H NMR (400 MHz, DMSO-d$_6$) δ 1.0-1.65 (m, 13H), 1.7-1.85 (m, 4H), 1.95 (t, 2H), 2.40 (pent., 1H), 2.87 (m, 2H), 5.26 (brs, 2H), 8.66 (brs, 1H).

Step D:

The above N-hydroxyamidine (0.24 g, 1.0 mmol) was dissolved in glacial acetic acid (12 mL) and 4-methanesulfonylbenzoyl chloride (0.24 g, 1.1 mmol, prepared from heating 4-methanesulfonylbenzoic acid and thionylchloride in 1,2-dichloroethane at reflux overnight) was added. The reaction mixture was stirred overnight at ambient temperature and then heated at reflux for 1 h. The mixture was concentrated in vacuo and the residue was dissolved in a mixture of 1 N hydrochloric acid (10 mL) and water (50 mL). The aqueous solution was extracted with diethyl ether (3×15 mL). The organic extracts were discarded and the aqueous phase was made alkaline with 4 N sodium hydroxide and then extracted with ethyl acetate (2×30 mL). The combined organic extracts were evaporated and the residue was dissolved in 1 N hydrochloric acid (10 mL). The mixture was evaporated and re-evaporated twice with acetonitrile to give a solid residue that was crystallised from ethyl acetate. This afforded 0.25 g of the title compound as a solid.

$^1$H NMR (400 MHz, CDCl$_3$) δ 1.5-1.7 (m, 5H), 1.85-2.0 (m, 5H), 2.0-2.25 (m, 5H), 2.52-2.64 (m, 2H), 2.87 (t, 2H), 3.12 (s, 3H), 3.15-3.22 (m, 1H), 3.62-3.70 (m, 2H), 8.12 (d, 2H), 8.33 (d, 2H), 12.15 (brs). HPLC: Rt=8.88 min.

Example 2 (General Procedure (A))

1-Cyclopentyl-4-{2-[5-(4-cyanophenyl)[1,2,4]oxadiazol-3-yl]ethyl}piperidine, hydrochloride

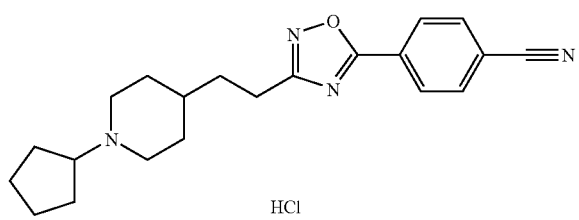

The title compound was prepared by a similar procedure to that described in Example 1, starting from 3-(1-cyclopentylpiperidin-4-yl)-N-hydroxypropionamidine and 4-cyanobenzoyl chloride.

$^1$H NMR (400 MHz, CDCl$_3$) δ 1.4-2.3 (m, 15H), 1.2.50-2.17 (m, 2H), 2.87 (t, 2H), 3.10-3.25 (m, 1H), 3.59-3.73 (m, 2H), 7.85 (d, 2H), 8.24 (d, 2H), 12.1 (brs, 1H).

HPLC: Rt=11.26 min.

Example 3 (General Procedure (A))

1-Cyclopentyl-4-{3-[5-(4-furan-2-ylphenyl)[1,2,4]oxadiazol-3-yl]propyl}piperidine, hydrochloride

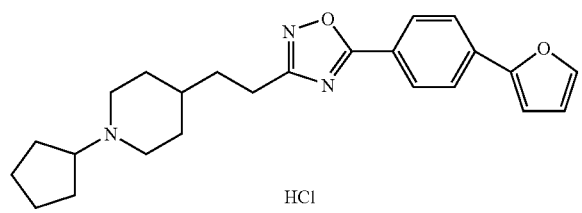

HCl

Step A:

3-(1-Cyclopentylpiperidin-4-yl)-1-propanol

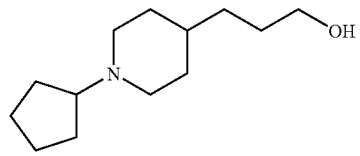

To a solution of 3-(piperidin-4-yl)-1-propanol (4.7 g, 33 mmol) in acetonitril (100 mL) was added potassium carbonate (25 g, 180 mmol) and cyclopentylbromide (24.5 g, 164 mmol) and the reaction mixture was stirred at reflux temperature overnight. The mixture was allowed to cool, then filtered and the solvent evaporated. The residue was dissolved in ethyl acetate (150 mL) and the organic mixture was dried (MgSO$_4$). The mixture was filtered and the solvent was evaporated. The residue was treated with diethyl ether (100 mL) and the organic phase was decanted and evaporated. This afforded 5.8 g of 3-(1-cyclopentylpiperidin-4-yl)-1-propanol contaminated with probably cyclopentylbromide. $^1$H NMR (400 MHz, CDCl$_3$) δ 1.2-2.0 (m, 17H), 2.05-2.15 (m, 1H), 2.45 (pent., 1H), 2.95-3.05 (m, 2H), 3.55-3.65 (m, 2H), 4.28-4.36 (m, 2H).

Step B:

4-(1-Cyclopentylpiperidin-4-yl)-N-hydroxybutyramidine

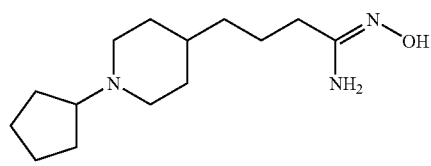

To a stirred solution of the above alcohol (5.8 g, 27 mmol) in diethyl ether (100 mL) was added triethylamine (3.2 g, 32 mmol) followed by dropwise addition of methanesulfonyl chloride (3.5 g, 30 mmol). When addition was complete the mixture was stirred overnight at ambient temperature. The mixture was filtered and the solvent was evaporated to give an oily residue that was dissolved in absolute ethanol (50 mL). Potassium cyanide (3.6 g, 55 mmol) was added and the mixture was heated to reflux and another portion of absolute ethanol (25 mL) was added. Then the reaction mixture was heated at reflux for 5 h. The reaction mixture was allowed to cool to ambient temperature, filtered and the solvent was evaporated. The oily residue was dissolved in ethyl acetate (100 mL) and the organic solution was washed with water (2×10 mL) and dried (MgSO$_4$) in the presence of a small amount of activated carbon. The mixture was filtered and the solvent was evaporated to give 2.1 g of crude 4-(1-cyclopentylpiperidin-4-yl)butyronitril.

A mixture of the above nitril (2.0 g, 9.1 mmol), absolute ethanol (15 mL), hydroxylamine hydrochloride (1.3 g, 18 mmol), water (4 mL) and potassium carbonate (2.8 g, 21 mmol) was stirred at ambient temperature for 1 h. Then the reaction mixture was heated overnight at reflux. The mixture was allowed to cool and then concentrated in vacuo. The residue was stirred with a mixture of water (20 mL) and ethyl acetate (20 mL) and the solid was isolated by filtration. The solid was washed with ethyl acetate and dried in vacuo. This afforded 1.0 g of 4-(1-cyclopentylpiperidin-4-yl)-N-hydroxybutyramidine. $^1$H NMR (400 MHz, DMSO-d$_6$) δ 1.0-1.35 (m, 7H), 1.35-1.66 (m, 8H), 1.66-1.86 (m, 4H), 1.92 (t, 2H), 2.39 (pent., 1H), 2.82-2.91 (m, 2H), 5.27 (brs, 2H), 8.64 (brs, 1H).

Step C:

The above N-hydroxyamidine (0.25 g, 1.0 mmol) was dissolved in glacial acetic acid (10 mL) and 2-furoylchloride (0.16 g, 1.2 mmol) was added. The reaction mixture was stirred overnight at ambient temperature and then heated at reflux for 1 h. The mixture was concentrated in vacuo and the residue was dissolved in a mixture of 1 N hydrochloric acid (10 mL) and water (50 mL). The acidic mixture was made alkaline with 4 N sodium hydroxide and then extracted with ethyl acetate (2×50 mL). The combined organic extracts were evaporated and the residue was stirred with 1 N hydrochloric acid (10 mL). The mixture was evaporated and re-evaporated twice with acetonitrile to give a solid residue that was crystallised from ethyl acetate. This afforded 0.21 g of the title compound as a solid. $^1$H NMR (400 MHz, CDCl$_3$) δ 1.35-2.25 (m, 17H), 2.50-2.63 (m, 2H), 2.78 (t, 2H), 3.10-3.20 (m, 1H), 3.6-3.7 (m, 2H), 6.62-6.65 (m, 1H), 7.32 (d, 1H), 7.69 (d, 1H), 12.05 (brs). HPLC: Rt=10.87 min.

Example 4 (General Procedure (A))

1-Cyclopentyl-4-{3-[5-(4-chlorophenyl)[1,2,4]oxadiazol-3-yl]propyl}piperidine, hydrochloride

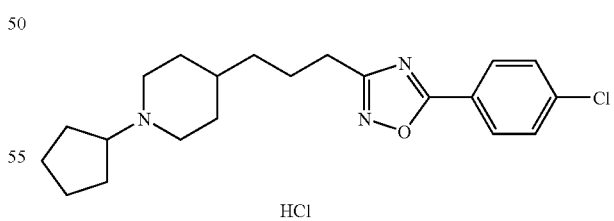

HCl

The title compound was prepared by a similar procedure to that described in Example 3, starting from 4-(1-cyclopentylpiperidin-4-yl)-N-hydroxybutyramidine and 4-chlorobenzoyl chloride.

$^1$H NMR (400 MHz, DMSO-d$_6$) δ 1.27-1.35 (m, 2H), 1.45-1.63 (m, 5H), 1.64-1.86 (m, 8H), 1.92-2.03 (m, 2H), 2.75-2.88 (m, 4H), 3.33-3.47 (m, 3H), 7.70 (d, 2H), 8.10 (d, 2H), 10.35 (brs, 1H). HPLC: Rt=15.93 min.

Example 5 (General Procedure (A))

1-Cyclopentyl-4-{3-[5-(4-methoxyphenyl)[1,2,4]oxadiazol-3-yl]propyl}piperidine, hydrochloride

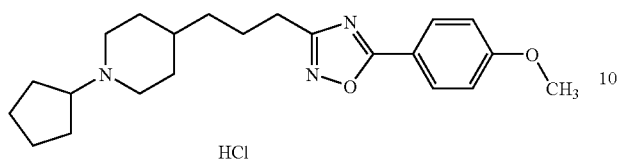

The title compound was prepared by a similar procedure to that described in Example 3, starting from 4-(1-cyclopentylpiperidin-4-yl)-N-hydroxybutyramidine and 4-methoxybenzoyl chloride.

$^1$H NMR (400 MHz, DMSO-$d_6$) δ 1.25-1.35 (m, 2H), 1.43-1.60 (m, 5H), 1.64-1.88 (m, 8H), 1.92-2.03 (m, 2H), 2.72-2.88 (m, 4H), 3.35-3.47 (m, 3H), 7.16 (d, 2H), 8.03 (d, 2H), 10.4 (brs, 1H). HPLC: Rt=14.13 min.

Example 6 (General Procedure (A))

1-Cyclopentyl-4-{3-[5-3,4-dichlorophenyl)[1,2,4]oxadiazol-3-yl]propyl}piperidine, hydrochloride

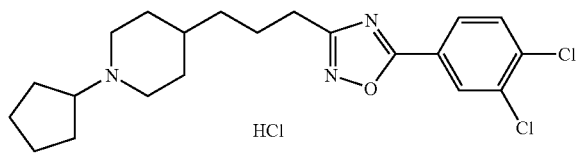

The title compound was prepared by a similar procedure to that described in Example 3, starting from 4-(1-cyclopentylpiperidin-4-yl)-N-hydroxybutyramidine and 3,4-dichlorobenzoyl chloride.

$^1$H NMR (400 MHz, DMSO-$d_6$) δ 1.25-1.36 (m, 2H), 1.46-1.60 (m, 5H), 1.62-1.90 (m, 8H), 1.92-2.04 (m, 2H), 2.75-2.88 (m, 4H), 3.37-3.46 (m, 3H), 7.91 (d, 1H), 8.05 (dd, 1H), 8.27 (d, 1H), 10.55 (brs, 1H). HPLC: Rt=18.21 min.

Example 7 (General Procedure (A))

1-Cyclopentyl-4-{3-[5-(4-methanesulfonylphenyl)[1,2,4]oxadiazol-3-yl]propyl}piperidine, hydrochloride

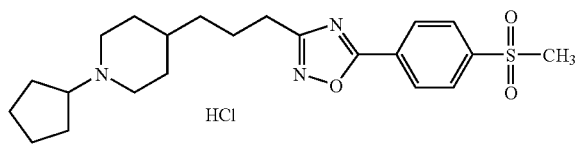

The title compound was prepared by a similar procedure to that described in Example 3, starting from 4-(1-cyclopentylpiperidin-4-yl)-N-hydroxybutyramidine and 4-methylsulfonylbenzoyl chloride.

$^1$H NMR (400 MHz, DMSO-$d_6$) δ 1.27-1.36 (m, 2H), 1.43-1.63 (m, 5H), 1.64-1.90 (m, 8H), 1.92-2.04 (m, 2H), 2.77-2.92 (m, 4H), 3.35-3.50 (m, 6H), 8.18 (d, 2H), 8.35 (d, 2H), 10.35 (brs, 1H). HPLC: Rt=10.63 min.

Example 8 (General Procedure (A))

1-Cyclopentyl-4-{3-[5-cyclopropyl[1,2,4]oxadiazol-3-yl]propyl}piperidine, hydrochloride

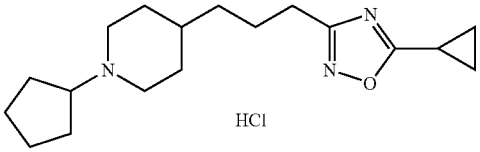

The title compound was prepared by a similar procedure to that described in Example 3, starting from 4-(1-cyclopentylpiperidin-4-yl)-N-hydroxybutyramidine and cyclopropylcarbonyl chloride.

HPLC: Rt=9.40 min.

Example 9 (General Procedure (A))

1-(1-Ethylpropyl)-4-{3-[5-(4-methanesulfonylphenyl)[1,2,4]oxadiazol-3-yl]propyl}piperidine, hydrochloride

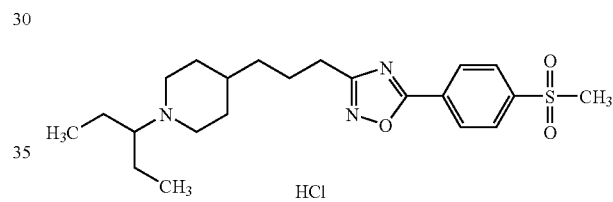

The title compound was prepared by a similar procedure to that described in Example 3, starting from 4-(1-(1-ethylpropyl)piperidin-4-yl)-N-hydroxybutyramidine and 4-methylsulfonylbenzoyl chloride.

$^1$H NMR (400 MHz, CDCl$_3$) δ 1.10 (t, 6H), 1.43-1.57 (m, 3H), 1.60-1.72 (m, 2H), 1.80-1.92 (m, 4H), 2.00-2.13 (m, 2H), 2.15-2.28 (m, 2H), 2.70-2.92 (m, 5H), 3.12 (s, 3H), 3.38-3.46 (m, 2H), 8.13 (d, 2H), 8.34 (m, 2H), 11.65 (brs, 1H). HPLC: Rt=11.89 min.

Example 10 (General Procedure (A))

1-(1-Ethylpropyl)-4-{3-[5-(4-trifluoromethylphenyl)[1,2,4]oxadiazol-3-yl]propyl}piperidine, hydrochloride

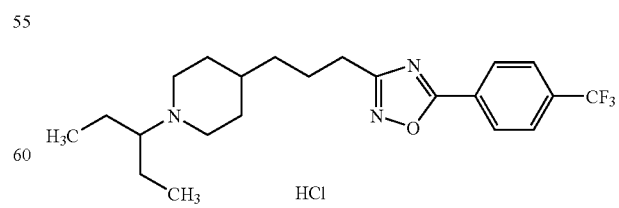

The title compound was prepared by a similar procedure to that described in Example 3, starting from 4-(1-(1-ethylpropyl)piperidin-4-yl)-N-hydroxybutyramidine and 4-trifluoromethylbenzoyl chloride.

¹H NMR (400 MHz, CDCl₃) δ 1.10 (t, 6H), 1.43-1.57 (m, 3H), 1.60-1.72 (m, 2H), 1.80-1.92 (m, 4H), 2.02-2.12 (m, 2H), 2.15-2.29 (m, 2H), 2.70-2.92 (m, 5H), 3.37-3.45 (m, 2H), 7.30 (d, 2H), 8.25 (d, 2H), 11.7 (brs, 1H). HPLC: Rt=18.55 min.

Example 11 (General Procedure (A))

1-(1-Ethylpropyl)-4-{3-[5-(4-cyclohexylphenyl)[1,2,4]oxadiazol-3-yl]propyl}piperidine, hydrochloride

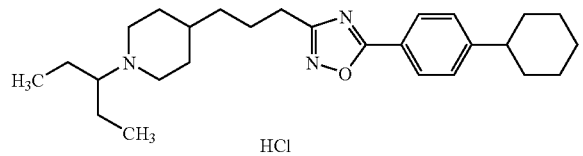

The title compound was prepared by a similar procedure to that described in Example 3, starting from 4-(1-(1-ethylpropyl)piperidin-4-yl)-N-hydroxybutyramidine and 4-cyclohexylbenzoyl chloride.

¹H NMR (400 MHz, CDCl₃) δ 1.08 (t, 6H), 1.20-1.53 (m, 8H), 1.59-1.71 (m, 2H), 1.75-1.94 (m, 9H), 2.00-2.10 (m, 2H), 2.13-2.27 (m, 2H), 2.54-2.63 (m, 1H), 2.68-2.81 (m, 4H), 2.86-2.93 (m, 1H), 3.37-3.44 (m, 2H), 7.36 (d, 2H), 8.03 (d, 2H), 11.7 (brs, 1H). HPLC: Rt=25.02 min.

Example 12 (General Procedure (A))

1-(1-Ethylpropyl)-4-{[5-(4-trifluoromethylphenyl)[1,2,4]oxadiazol-3-yl]methyl}piperidine, hydrochloride

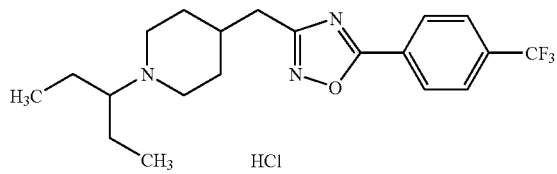

Step A:

4-(Cyanomethyl)piperidine-1-carboxylic acid tert-butyl ester

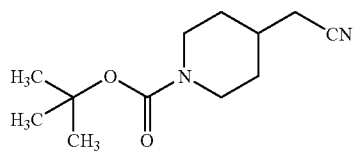

To a solution of 4-(hydroxymethyl)piperidine-1-carboxylic acid tert-butyl ester (9.0 g, 42 mmol) in acetonitril (125 mL) was added triethylamine (5.5 g, 54 mmol) followed by dropwise addition of methanesulfonyl chloride (5.7 g, 50 mmol). When addition was complete the mixture was stirred overnight. The mixture was filtered and the solvent was evaporated. The residue was dissolved in ethyl acetate (100 mL) and the organic solution was washed with water (2×10 mL) and brine. The organic phase was dried (MgSO₄) and the solvent was evaporated to give a residue that was dissolved in absolute ethanol (250 mL). Potassium cyanide (8.2 g, 125 mmol) was added and the mixture was heated at reflux overnight. The reaction mixture was allowed to cool to ambient temperature, filtered and the solvent was evaporated. The residue was dissolved in diethyl ether (200 mL) and the organic solution was washed with water (2×20 mL) and then dried (MgSO₄) in the presence of activated carbon. The mixture was filtered and the solvent was evaporated to give 9.2 g of 4-(cyanomethyl)piperidine-1-carboxylic acid tert-butyl ester. ¹H NMR (400 MHz, CDCl₃) δ 1.20-1.33 (m, 2H), 1.46 (s, 9H), 1.77-1.88 (m, 3H), 2.32 (d, 2H), 2.66-2.78 (m, 2H), 4.10-4.23 (m, 2H).

Step B:

2-((1-Ethylpropyl)piperidin-4-yl)-N-hydroxyacetamidine

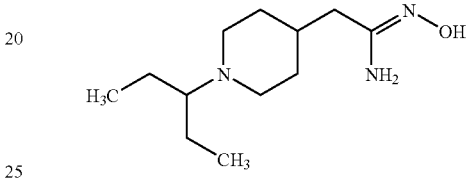

The above nitrile (9.2 g, 41 mmol) was dissolved in dichloromethane (50 mL) and trifluoroacetic acid (15 mL) was added. The mixture was stirred for 45 min at ambient temperature and then the solvent was evaporated. The residue was dissolved in acetonitrile (200 mL) and with stirring, excess potassium carbonate was added. The mixture was filtered and the solvent was evaporated. The oily residue was dissolved in acetonitrile (150 mL) and 3-pentylbromide (15.6 g, 105 mmol) and potassium carbonate (25.5 g, 185 mmol) were added and the reaction mixture was stirred at reflux temperature overnight. The mixture was allowed to cool, then filtered and the solvent evaporated. The residue was dissolved in ethyl acetate (200 mL) and the organic phase was washed with water (20 mL). The organic phase was dried (MgSO₄) in the presence of activated carbon, filtered and the solvent was evaporated. This afforded 7.8 g of crude 2-(1-(1-ethylpropyl)piperidin-4-yl)acetonitrile. This nitrile (7.8 g, 40 mmol) was dissolved in absolute ethanol (70 mL) and hydroxylamine hydrochloride (4.2 g, 60 mmol), water (10 mL) and potassium carbonate (8.9 g, 64 mmol) were added. The reaction mixture was stirred 1 h at ambient temperature and then heated overnight at reflux. The mixture was allowed to cool and then concentrated in vacuo. The residue was stirred with a mixture of water (100 mL) and ethyl acetate (200 mL). The phases were separated and the aqueous phase was extracted with ethyl acetate (100 mL). The combined organic extracts were dried (MgSO₄) and the solvent was evaporated. The residue was stirred with petrol ether, isolated by filtration and dried. This afforded 3.2 g of 2-((1-ethylpropyl)piperidin-4-yl)-N-hydroxyacetamidine. ¹H NMR (400 MHz, CDCl₃) δ 0.87 (t, 6H), 1.17-1.35 (m, 4H), 1.40-1.58 (m, 3H), 1.65-1.73 (m, 2H), 2.03 (d, 2H), 2.13 (pent., 1H), 2.18-2.28 (m, 2H), 2.67-2.76 (m, 2H), 4.52 (brs, 2H), 7.9 (brs, 1H).

Step C:

The above N-hydroxyamidine (0.25 g, 1.1 mmol) was dissolved in glacial acetic acid (5 mL) and with stirring 4-trifluoromethylbenzoyl chloride (0.25 g, 1.2 mmol) was added dropwise at ambient temperature. The reaction mixture was stirred overnight at ambient temperature and then heated at reflux for 45 minutes. The mixture was concentrated in vacuo and the residue was dissolved in a mixture of 1 N hydrochloric acid (10 mL), water (100 mL) and diethyl ether (20 mL). The phases were separated and the aqueous phase was washed with diethyl ether (20 mL). The combined diethyl ether phases containing solid material were extracted with water (3×20 mL). The organic extracts were discarded and all the combined aqueous phases were made alkaline (pH 10-11) with 4 N sodium hydroxide and then extracted with ethyl acetate (150 mL). The organic extract was evaporated and the residue was dissolved in 1 N hydrochloric acid (10 mL). The mixture was evaporated and re-evaporated with acetone to give a solid residue that was stirred with diethyl ether. The solid was isolated by filtration and dried to give 0.32 g of the title compound as a solid.

$^1$H NMR (400 MHz, CDCl$_3$) δ 1.10 (t, 6H), 1.62-1.76 (m, 2H), 1.95-2.16 (m, 5H), 2.37-2.50 (m, 2H), 2.76-2.96 (m, 5H), 3.42-3.48 (m, 2H), 7.80 (d, 2H), 8.24 (d, 2H), 11.85 (brs, 1H). HPLC: Rt=18.61 min.

Example 13 (General Procedure (A))

1-Cyclopentyl-4-{[5-(4-methoxybenzyl)[1,2,4]oxadiazol-3-yl]methyl}piperidine, hydrochloride

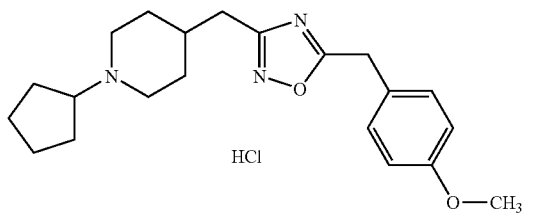

The title compound was prepared by a similar procedure to that described in Example 12, starting from 4-(1-cyclopentylpiperidin-4-yl)-N-hydroxyacetamidine and 4-methoxyphenylacetyl chloride.

$^1$H NMR (400 MHz, DMSO-d$_6$) δ 1.45-2.05 (m, 13H), 2.60-2.65 (m, 2H), 2.80-2.92 (m, 2H), 3.32-3.48 (m, 3H), 3.74 (s, 3H), 4.24 (s, 2H), 6.90 (d, 2H), 7.25 (d, 2H), 10.45 (brs, 1H). HPLC: Rt=11.11 min.

Example 14 (General Procedure (A))

1-Cyclopentyl-4-{[5-biphenyl-4-yl[1,2,4]oxadiazol-3-yl]methyl}piperidine, hydrochloride

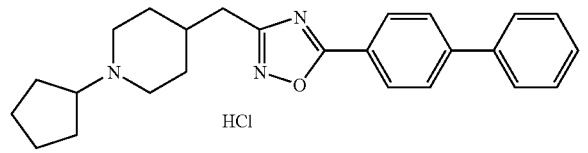

The title compound was prepared by a similar procedure to that described in Example 12, starting from 4-(1-cyclopentylpiperidin-4-yl)-N-hydroxyacetamidine and 4-phenylbenzoyl chloride.

$^1$H NMR (400 MHz, DMSO-d$_6$) δ 1.45-2.15 (m, 13H), 2.78 (d, 2H), 2.85-2.97 (m, 2H), 3.34-3.43 (m, 1H), 3.44-3.50 (m, 2H), 7.45 (t, 1H), 7.52 (t, 2H), 7.77 (d, 2H), 7.95 (d, 2H), 8.17 (d, 2H), 10.3 (brs, 1H). HPLC: Rt=17.08 min.

Example 15 (General Procedure (A))

1-Cyclopentyl-4-{[5-(2-(3-trifluoromethylphenyl)vinyl[1,2,4]oxadiazol-3-yl]-methyl}piperidine, hydrochloride

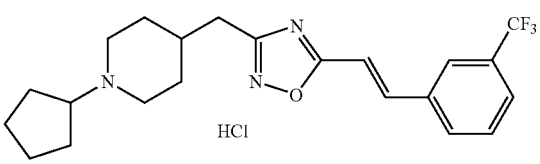

The title compound was prepared by a similar procedure to that described in Example 12, starting from 4-(1-cyclopentylpiperidin-4-yl)-N-hydroxyacetamidine and 3-(trifluoromethyl)cinnamoyl chloride.

$^1$H NMR (400 MHz, CDCl$_3$) δ 1.55-2.45 (m, 13H), 2.55-2.70 (m, 2H), 2.82 (d, 2H), 3.15-3.25 (m, 1H), 3.60-3.72 (m, 2H), 7.01-7.08 (m, 1H), 7.57 (t, 1H), 7.68 (d, 1H), 7.73-7.85 (m, 3H), 12.2 (brs, 1H). HPLC: Rt=19.33 min.

Example 16 (General Procedure (A))

1-Cyclopentyl-4-{[5-(4-methoxyphenyl)[1,2,4]oxadiazol-3-yl]methyl}piperidine, Hydrochloride

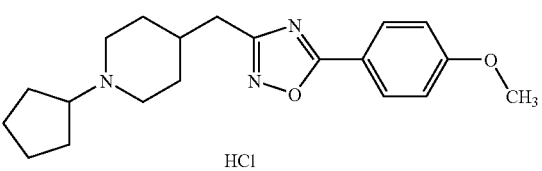

The title compound was prepared by a similar procedure to that described in Example 12, starting from 4-(1-cyclopentylpiperidin-4-yl)-N-hydroxyacetamidine and 4-methoxybenzoyl chloride.

$^1$H NMR (400 MHz, DMSO-d$_6$) δ 1.45-2.15 (m, 13H), 2.73 (d, 2H), 2.84-2.95 (m, 2H), 3.36-3.00 (m, 3H), 3.87 (s, 3H), 7.17 (d, 2H), 8.05 (d, 2H), 11.4 (brs, 1H). HPLC: Rt=11.96 min.

Example 17 (General Procedure (A))

1-(1-Ethylpropyl)-4-{[5-(biphenyl-4-yl)[1,2,4]oxadiazol-3-yl]methyl}piperidine, Hydrochloride

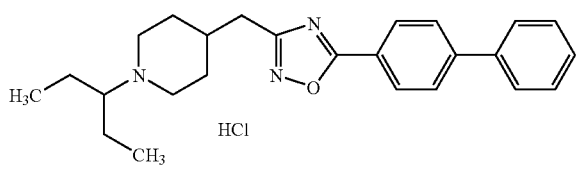

The title compound was prepared by a similar procedure to that described in Example 12, starting from 2-((1-ethylpropyl)piperidin-4-yl)-N-hydroxyacetamidine and 4-phenylbenzoyl chloride.

¹HNMR (400 MHz, CDCl₃) δ 1.10 (t, 6H), 1.60-1.76 (m, 2H), 1.96-2.20 (m, 5H), 2.36-2.48 (m, 2H), 2.76-2.97 (m, 5H), 3.41-3.48 (m, 2H), 7.40-7.52 (m, 3H), 7.65 (d, 2H), 7.75 (d, 2H), 8.17 (d, 2H), 11.85 (brs, 1H). HPLC: Rt=21.54 min.

Example 18 (General Procedure (A))

1-(1-Ethylpropyl)-4-{[5-(naphthalen-2-yl)[1,2,4]oxadiazol-3-yl]methyl}piperidine, Hydrochloride

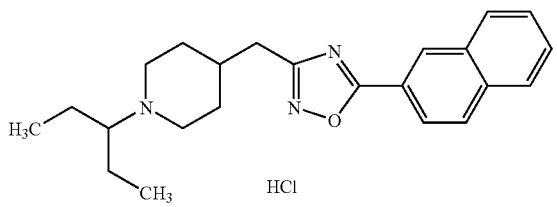

The title compound was prepared by a similar procedure to that described in Example 12, starting from 2-((1-ethylpropyl)piperidin-4-yl)-N-hydroxyacetamidine and 2-naphthoyl chloride.

¹H NMR (400 MHz, CDCl₃) δ 1.10 (t, 6H), 1.60-1.76 (m, 2H), 1.97-2.20 (m, 5H), 2.37-2.50 (m, 2H), 2.77-2.97 (m, 5H), 3.42-3.50 (m, 2H), 7.57-7.65 (m, 2H), 7.90 (d, 1H), 7.95-7.99 (m, 2H), 8.12 (d, 1H), 8.66 (s, 1H), 11.85 (brs, 1H). HPLC: Rt=19.66 min.

Example 19 (General Procedure (A))

1-(1-Ethylpropyl)-4-{[5-(4-tert-butylphenyl)[1,2,4]oxadiazol-3-yl]methyl}Piperidine, Hydrochloride

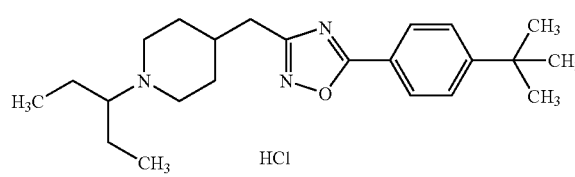

The title compound was prepared by a similar procedure to that described in Example 12, starting from 2-((1-ethylpropyl)piperidin-4-yl)-N-hydroxyacetamidine and 4-tert-butylbenzoyl chloride.

¹H NMR (400 MHz, CDCl₃) δ 1.09 (t, 6H), 1.36 (s, 9H), 1.62-1.72 (m, 2H), 1.94-2.17 (m, 5H), 2.35-2.47 (m, 2H), 2.76-2.94 (m, 5H), 3.40-3.48 (m, 2H), 7.53 (d, 2H), 8.02 (d, 2H), 11.8 (brs, 1H). HPLC: Rt=19.07 min.

Example 20 (General Procedure (A))

1-(1-Ethylpropyl)-4-{[5-(2-fluoro-4-trifluoromethylphenyl)[1,2,4]oxadiazol-3-yl]methyl}piperidine, Hydrochloride

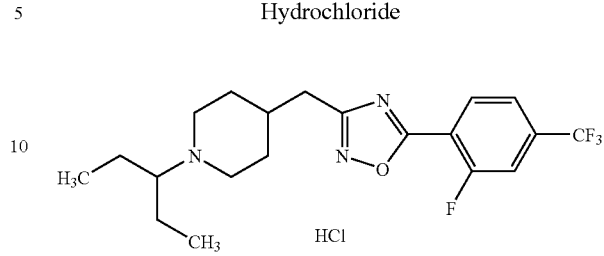

The title compound was prepared by a similar procedure to that described in Example 12, starting from 2-((1-ethylpropyl)piperidin-4-yl)-N-hydroxyacetamidine and 2-fluoro-4-trifluoromethylbenzoyl chloride.

¹H NMR (400 MHz, CDCl₃) δ 1.10 (t, 6H), 1.60-1.74 (m, 2H), 1.93-2.18 (m, 5H), 2.37-2.50 (m, 2H), 2.76-2.96 (m, 5H), 3.41-3.48 (m, 2H), 7.55 (d, 1H), 7.60 (d, 1H), 8.25 (t, 1H), 11.85 (brs, 1H). HPLC: Rt=16.33 min.

Example 21 (General Procedure (A))

1-(1-Ethylpropyl)-4-{[5-(3-trifluoromethylphenyl)[1,2,4]oxadiazol-3-yl]methyl}piperidine, Hydrochloride

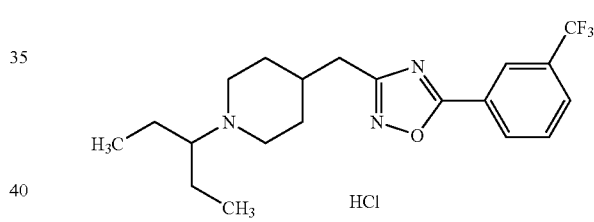

The title compound was prepared by a similar procedure to that described in Example 12, starting from 2-((1-ethylpropyl)piperidin-4-yl)-N-hydroxyacetamidine and 3-trifluoromethylbenzoyl chloride.

¹H NMR (400 MHz, CDCl₃) δ 1.10 (t, 6H), 1.60-1.75 (m, 2H), 1.93-2.19 (m, 5H), 2.37-2.50 (m, 2H), 2.78-2.96 (m, 5H), 3.41-3.48 (m, 2H), 7.68 (t, 1H), 7.86 (d, 1H), 8.30 (d, 1H), 8.38 (s, 1H), 11.9 (brs, 1H). HPLC: Rt=15.99 min.

Example 22 (General Procedure (A))

1-(1-Ethylpropyl)-4-{[5-(4-trifluoromethoxyphenyl)[1,2,4]oxadiazol-3-yl]-methyl}piperidine, Hydrochloride

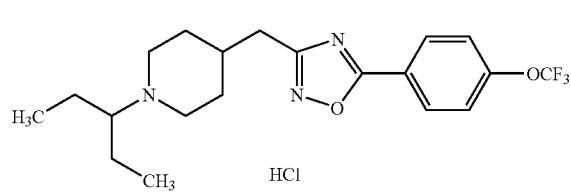

The title compound was prepared by a similar procedure to that described in Example 12, starting from 2-((1-ethylpropyl)piperidin-4-yl)-N-hydroxyacetamidine and 4-trifluoromethoxybenzoyl chloride.

$^1$H NMR (400 MHz, CDCl$_3$) δ 1.10 (t, 6H), 1.62-1.76 (m, 2H), 1.94-2.16 (m, 5H), 2.36-2.48 (m, 2H), 2.76-2.84 (m, 2H), 2.85 (d, 2H), 2.88-2.96 (m, 1H), 3.40-3.48 (m, 2H), 7.37 (d, 2H), 8.14-8.18 (m, 2H), 11.85 (brs, 1H). HPLC: Rt=15.31 min.

Example 23 (General Procedure (B))

4-[5-(4-(Piperidin-1-ylmethyl)phenyl)[1,2,4]oxadiazol-3-ylmethyl]-1-(1-ethylpropyl)piperidine, Dihydrochloride

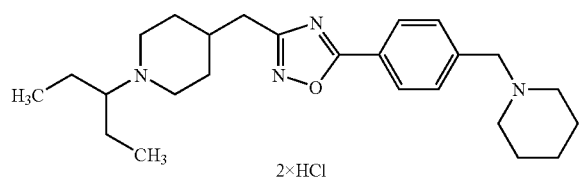

Step A:

4-[5-(4-(chloromethyl)phenyl)[1,2,4]oxadiazol-3-ylmethyl]-1-(1-ethylpropyl)piperidine

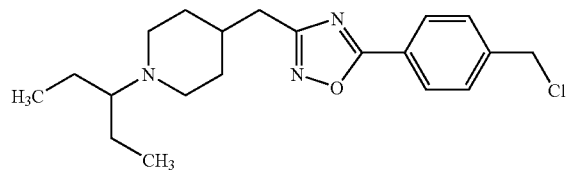

A mixture of 2-((1-ethylpropyl)piperidin-4-yl)-N-hydroxyacetamidine (0.50 g, 2.2 mmol, prepared as described in Example 12), glacial acetic acid (15 mL) and 4-(chloromethyl)benzoyl chloride (0.46 g, 2.4 mmol) was stirred overnight at ambient temperature and then heated at reflux for 30 minutes. The mixture was concentrated in vacuo and the residue was dissolved in a mixture of 1 N hydrochloric acid (10 mL), water (50 mL) and diethyl ether (20 mL). The phases were separated and the aqueous phase was washed with diethyl ether (2×10 mL). The organic extracts were discarded and the aqueous phase was made alkaline (pH 10) with 4 N sodium hydroxide and then extracted with ethyl acetate (2×50 mL). The combined organic extracts were dried (MgSO$_4$) and the solvent was evaporated. This afforded 0.70 g of 4-[5-(4-(chloromethyl)phenyl)-[1,2,4]oxadiazol-3-ylmethyl]-1-(1-ethylpropyl)piperidine as an oil.
$^1$H NMR (400 MHz, CDCl$_3$) δ 0.87 (t, 6H), 1.22-1.49 (m, 4H), 1.40-1.52 (m, 2H), 1.67-1.74 (m, 2H), 1.78-1.88 (m, 1H), 2.13 (pent., 1H), 2.23-2.31 (m, 2H), 2.68-2.75 (m, 4H), 4.63 (s, 2H), 7.55 (d, 2H), 8.14 (d, 2H). HPLC: Rt=14.22 min.

Step B:

The above chloromethyl derivative (0.30 g, 0.83 mmol) was dissolved in absolute ethanol (10 mL) and piperidine (0.5 mL) was added. The reaction mixture was heated at reflux for 2 h and then the volatiles were evaporated. The residue was stirred with a mixture of water (10 mL) and ethyl acetate (50 mL) and 4 N sodium hydroxide was added until pH 10. The phases were separated and the organic phase was evaporated. The residue was dissolved in 1 N hydrochloric acid (10 mL) and the volatiles were evaporated to give a residue that was re-evaporated with acetonitrile. The solid was stirred with acetonitrile, isolated by filtration and dried to give 0.21 g of the title compound as a solid.

$^1$H NMR (400 MHz, CDCl$_3$) δ 1.10 (t, 6H), 1.36-1.49 (m, 1H), 1.62-1.75 (m, 2H), 1.77-2.19 (m, 8H), 2.24-2.47 (m, 4H), 2.66-2.77 (m, 2H), 2.80-2.97 (m, 5H), 3.40-3.51 (m, 4H), 4.26 (d, 2H), 7.94 (d, 2H), 8.15 (d, 2H), 11.7 (brs, 1H), 12.4 (brs, 1H). HPLC: Rt=7.71 min.

Example 24 (General Procedure (B))

2-(4-{3-[1-(1-Ethylpropyl)piperidin-4-ylmethyl][1,2,4]oxadiazol-5-yl}benzyl)-1, 2,3,4-tetrahydroisoquinoline, Dihydrochloride

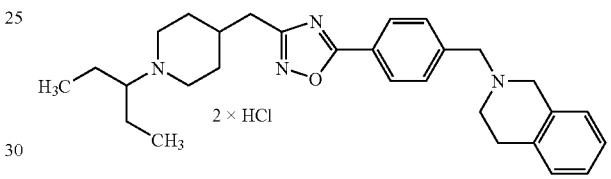

The title compound was prepared by a similar procedure to that described in Example 23, starting from 4-[5-(4-(chloromethyl)phenyl)[1,2,4]oxadiazol-3-ylmethyl]-1-(1-ethylpropyl)piperidine and 1,2,3,4-tetrahydroisoquinoline.

$^1$H NMR (400 MHz, CDCl$_3$) δ 1.10 (t, 6H), 1.60-1.73 (m, 2H), 1.77-1.83 (m, 2H), 1.90-2.20 (m, 4H), 2.32-2.47 (m, 2H), 2.78-2.96 (m, 5H), 3.00-3.11 (m, 1H), 3.25-3.58 (m, 4H), 3.66-3.77 (m, 1H), 4.05-4.16 (m, 1H), 4.32-4.50 (m, 3H), 7.03 (d, 1H), 7.20-7.33 (m, 3H), 7.98 (d, 2H), 8.17 (d, 2H), 11.75 (brs, 1H), 13.3 (brs, 1H). HPLC: Rt=7.87 min.

Example 25 (General Procedure (B))

1-(1-Ethylpropyl)-4-(4-{3-[1-(1-ethylpropyl)piperidin-4-ylmethyl][1,2,4]oxadiazol-5-yl}-benzyl)piperazine, Trihydrochloride

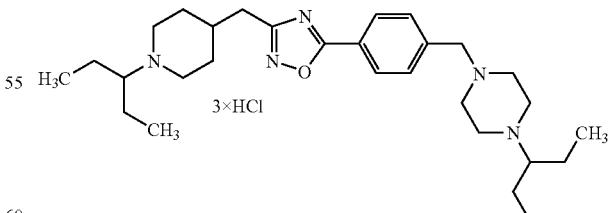

The title compound was prepared by a similar procedure to that described in Example 23, starting from 4-[5-(4-(chloromethyl)phenyl)-[1,2,4]oxadiazol-3-ylmethyl]-1-(1-ethylpropyl)piperidine and 1-(1-ethylpropyl)piperazine. HPLC: Rt=6.50 min.

Example 26 (General Procedure (B))

1-(4-{3-[1-(1-Ethylpropyl)piperidin-4-ylmethyl][1,2,4]oxadiazol-5-yl}benzyl)-4-phenyl-1,2,3,6-tetrahydropyridine, Dihydrochloride

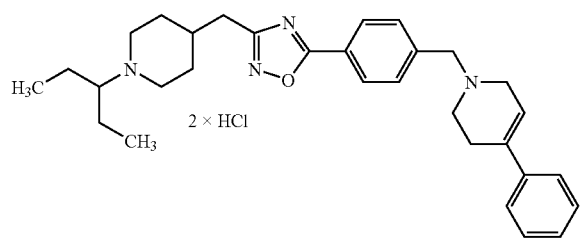

The title compound was prepared by a similar procedure to that described in Example 23, starting from 4-[5-(4-(chloromethyl)phenyl)[1,2,4]oxadiazol-3-ylmethyl]-1-(1-ethylpropyl)piperidine and 4-phenyl-1,2,3,6-tetrahydropyridine. HPLC: Rt=10.24 min.

Example 27 (General Procedure (B))

4-[5-(4-(Piperidin-1-ylmethyl)phenyl)[1,2,4]oxadiazol-3-ylmethyl]-1-(cyclopentyl)piperidine, Dihydrochloride

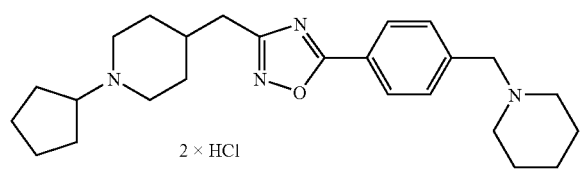

The title compound was prepared by a similar procedure to that described in Example 23, starting from 4-[5-(4-chloromethylphenyl)[1,2,4]oxadiazol-3-ylmethyl]-1-cyclopentylpiperidine and piperidine. HPLC: Rt=6.74 min.

Example 28 (General Procedure (B))

1-{4-[3-((1-Cyclopentylpiperidin-4-yl)methyl)[1,2,4]oxadiazol-5-yl]benzyl}-4-phenylpiperazine

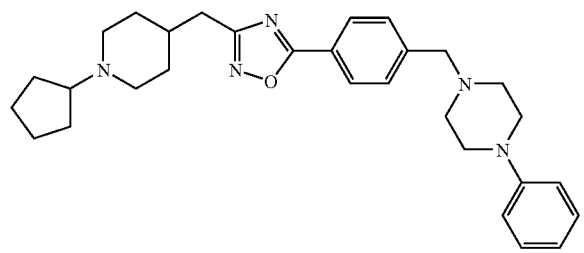

The title compound was prepared by a similar procedure to that described in Example 23, starting from 4-[5-(4-chloromethylphenyl) [1,2,4]oxadiazol-3-ylmethyl]-1-cyclopentyl-piperidine and 1-phenylpiperazine.
$^1$H NMR (400 MHz, CDCl$_3$) δ 1.33-2.00 (m, 15H), 2.45 (pent., 1H), 2.60-2.65 (m, 4H), 2.73 (d, 2H), 2.98-3.07 (m, 2H), 3.18-3.26 (m, 4H), 3.64 (s, 2H), 6.85 (t, 1H), 6.93 (d, 2H), 7.25 (t, 2H), 7.53 (d, 2H), 8.07 (d, 2H). HPLC: Rt=10.45 min.

Example 29 (General Procedure (B))

1-{4-[3-((1-Cyclopentylpiperidin-4-yl)methyl)[1,2,4]oxadiazol-5-yl]benzyl}-4-(4-fluoro-phenyl)-1,2,3,6-tetrahydropyridine, Dihydrochloride

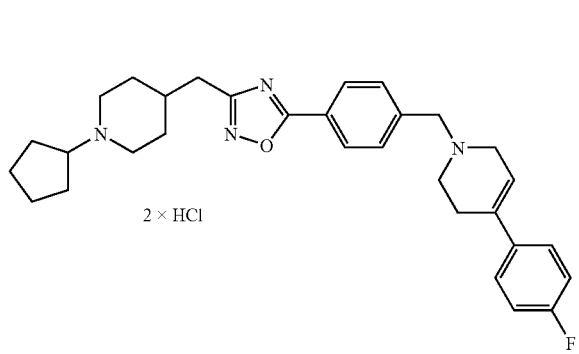

The title compound was prepared by a similar procedure to that described in Example 23, starting from 4-[5-(4-chloromethylphenyl)[1,2,4]oxadiazol-3-ylmethyl]-1-cyclopentylpiperidine and 4-(4-fluorophenyl)-1,2,3,6-tetrahydropyridine. HPLC: Rt=11.63 min.

Example 30 (General Procedure (B))

{4-[3-((1-Cyclopentylpiperidin-4-yl)methyl)[1,2,4]oxadiazol-5-yl]benzyl}methylamine, Dihydrochloride

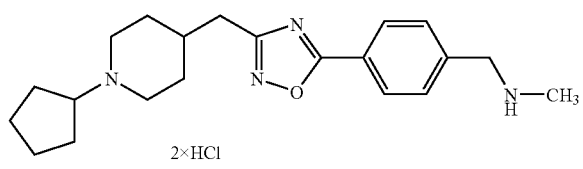

The title compound was prepared by a similar procedure to that described in Example 23, starting from 4-[5-(4-chloromethylphenyl)[1,2,4]oxadiazol-3-ylmethyl]-1-cyclopentylpiperidine and methylamine. HPLC: Rt=4.89 min.

Example 31 (General Procedure (B))

N-{4-[3-((1-Cyclopentylpiperidin-4-yl)methyl)[1,2,4]oxadiazol-5-yl]benzyl}-N,N-dimethylamine, Dihydrochloride

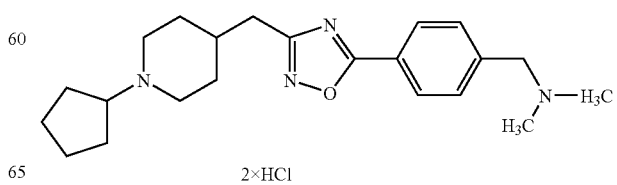

The title compound was prepared by a similar procedure to that described in Example 23, starting from 4-[5-(4-chloromethylphenyl)[1,2,4]oxadiazol-3-ylmethyl]-1-cyclopentylpiperidine and dimethylamine. HPLC: Rt=4.43 min.

Example 32 (General Procedure (C))

1-Cyclopentyl-4-[5-((4-phenoxymethyl)phenyl)[1,2,4]oxadiazol-3-ylmethyl]piperidine

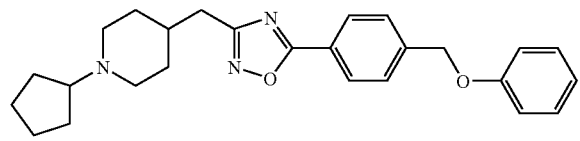

To a solution of phenol (0.10 g, 1.1 mmol) in THF (10 mL) was added a potassium tert-butoxide (1 mL, 1 M in THF) and the mixture was stirred at ambient temperature for 10 min. Then 4-[5-(4-chloromethylphenyl)[1,2,4]oxadiazol-3-ylmethyl]-1-cyclopentylpiperidine (0.27 g, 0.75 mmol, prepared similarly as described in Example 23) was added and the mixture was heated at reflux for 5-6 h. The solvent was evaporated and the residue was stirred 15 min with a mixture of 1 N sodium hydroxide (5 mL), water (5 mL) and ethyl acetate (20 mL). The phases were separated and the organic phase was washed with water (2×10 mL) and brine. The organic phase was dried (MgSO$_4$), filtered and evaporated. The residue was stirred with acetonitril and the solid was isolated by filtration and dried to give 0.14 g of the title compound.

$^1$H NMR (400 MHz, CDCl$_3$) δ 1.35-2.00 (m, 15H), 2.45 (pent., 1H), 2.73 (d, 2H), 2.98-3.07 (m, 2H), 5.15 (s, 2H), 6.95-7.01 (m, 3H), 7.27-7.33 (m, 2H), 7.59 (d, 2H), 8.13 (d, 2H). HPLC: Rt=19.23 min.

Example 33 (General Procedure (A))

1-Cyclopentyl-4-[5-(4-phenoxyphenyl)[1,2,4]oxadiazol-3-ylmethyl]piperidine, Hydrochloride

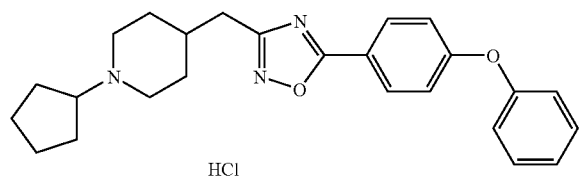

The title compound was prepared by a similar procedure to that described in Example 12, starting from 4-(1-cyclopentylpiperidin-4-yl)-N-hydroxyacetamidine and 4-phenoxybenzoyl chloride.

$^1$H NMR (400 MHz, CDCl$_3$) δ 1.55-2.35 (m, 13H), 2.56-2.68 (m, 2H), 2.82 (d, 2H), 3.10-3.23 (m, 1H), 3.62-3.70 (m, 2H), 7.05-7.12 (m, 4H), 7.23 (t, 1H), 7.38-7.44 (m, 2H), 8.06 (d, 2H), 12.3 (brs, 1H). HPLC: Rt=20.53 min.

Example 34 (General Procedure (A))

4-(5-(Biphenyl-4-ylmethyl)[1,2,4]oxadiazol-3-ylmethyl)-1-cyclopentylpiperidine

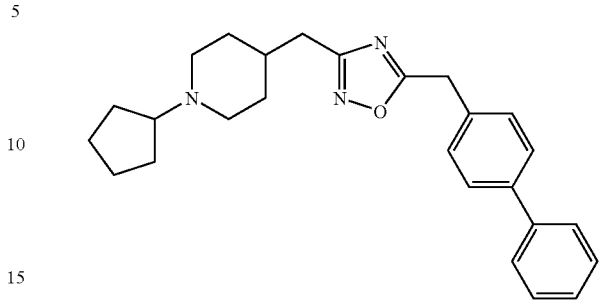

The title compound was prepared by a similar procedure to that described in Example 12, starting from 4-(1-cyclopentylpiperidin-4-yl)-N-hydroxyacetamidine and biphenyl-4-ylacetyl chloride.

$^1$H NMR (400 MHz, CDCl$_3$) δ 1.33-1.98 (m, 15H), 2.42-2.51 (m, 1H), 2.66 (d, 2H), 2.98-3.08 (m, 2H), 4.25 (s, 2H), 7.33-7.45 (m, 5H), 7.56-7.59 (m, 4H). HPLC: Rt=17.93 min.

Example 35 (General Procedure (A))

4-[5-(4-tert-Butylphenyl)[1,2,4]oxadiazol-3-yl]-1-cyclopropylpiperidine, hydrochloride

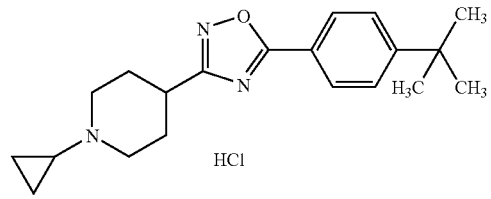

Step A:

1-Cyclopropyl-4-cyanopiperidine.

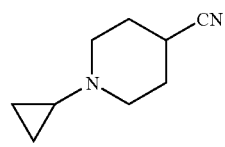

To a solution of 4-cyanopiperidine (2.5 g, 23 mmol, J. Org. Chem. 21, 984-986, 1957) in methanol (16 mL) and THF (65 mL) was added with stirring (1-ethoxycyclopropoxy)-trimethylsilane (7.0 g, 40 mmol), glacial acetic acid (2.3 mL) and sodium cyanoborohydride (3.3 g, 53 mmol). When addition was complete the mixture was stirred 1 h at ambient temperature and then heated overnight at 65° C. under an atmosphere of nitrogen. The solvent was evaporated and to the residue was added water (30 mL) and 1N HCl until pH 1. The mixture was washed with diethyl ether (50 mL) and the acidic aqueous phase was saturated with potassium carbonate. The alkaline mixture was extracted with ethyl acetate (2×100 mL). The combined organic extracts were dried (MgSO$_4$) and the solvent was evaporated. This afforded 3.2 g of 1-cyclopropyl-4-cyanopiperidine. $^1$H NMR (400 MHz, CDCl$_3$) δ 0.37-0.50 (m, 4H), 1.59-1.66 (m, 1H), 1.77-1.94 (m, 4H), 2.4-2.9 (m, 5H).

Step B:

1-Cyclopropyl-N-hydroxypiperidine-4-carboxamidine.

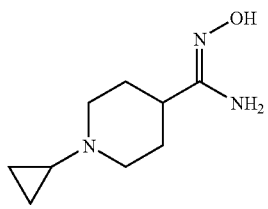

The above nitrile (3.1 g, 21 mmol) was dissolved in ethanol (50 mL) and hydroxylamine hydrochloride (5.7 g, 83 mmol), water (10 mL) and potassium carbonate (6.0 g, 43 mmol) were added. The reaction mixture was stirred 1 h at ambient temperature and then heated overnight at reflux. The mixture was allowed to cool and then concentrated in vacuo. The residue was stirred with water until it had dissolved. Potassium carbonate was added until pH 9 and the alkaline mixture was extracted with ethyl acetate (4×100 mL). The alkaline phase was saturated with sodium chloride and extracted again with ethyl acetate (2×100 mL). The combined ethyl acetate extracts were dried (MgSO$_4$) and the solvent was evaporated. The residue was stirred with acetonitril, isolated by filtration and dried. This afforded 1.2 g of 1-cyclopropyl-N-hydroxy-piperidine-4-carboxamidine. $^1$H NMR (400 MHz, DMSO-d$_6$) δ 0.23-0.29 (m, 2H), 0.37-0.41 (m, 2H), 1.43-1.67 (m, 5H), 1.91-1.1.99 (m, 1H), 2.05-2.13 (m, 2H), 2.89-2.96 (m, 2H), 5.25 (brs, 2H), 8.75 (s, 1H).

Step C:

The above N-hydroxyamidine (0.21 g, 1.15 mmol) was dissolved in glacial acetic acid (10 mL) and 4-tert-butylbenzoyl chloride (0.46 g, 2.34 mmol) was added. The reaction mixture was stirred 4 h at ambient temperature and then heated at reflux for 45 minutes. The mixture was concentrated in vacuo and the residue was treated with a mixture of 1 N hydrochloric acid (10 mL), water (50 mL) and diethyl ether (40 mL). The ether phase was discarded and the acidic aqueous phase containing a solid material was washed with diethyl ether (2×40 mL). The ether extracts were discarded and the acidic aqueous phase still containing a solid material was made alkaline (pH 11) with 4 N sodium hydroxide and then extracted with ethyl acetate (2×50 mL). The combined organic extracts were dried (MgSO$_4$), evaporated and the residue was dissolved in 1 N hydrochloric acid (4 mL). The solid was isolated by filtration and dried to give 0.15 g of the title compound as a solid. HPLC: Rt=17.96 min.

Example 35a (General Procedure (A))

4-[5-(4-tert-Butylphenyl)[1,2,4]oxadiazol-3-yl]-1-cyclopropylpiperidine, Fumarate

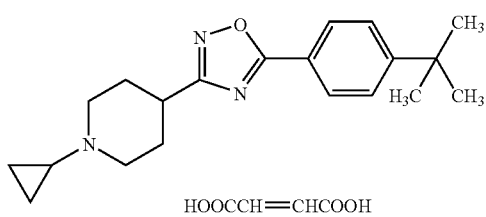

Step A:

1-Cyclopropyl-4-cyanopiperidine.

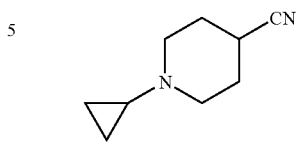

To a solution of 4-cyanopiperidine (2.5 g, 23 mmol, J. Org. Chem. 21, 984-986, 1957) in methanol (16 mL) and THF (65 mL) was added with stirring (1-ethoxycyclopropoxy)-trimethylsilane (7.0 g, 40 mmol), glacial acetic acid (2.3 mL) and sodium cyanoborohydride (3.3 g, 53 mmol). When addition was complete the mixture was stirred 1 h at ambient temperature and then heated overnight at 65° C. under an atmosphere of nitrogen. The solvent was evaporated and to the residue was added water (30 mL) and 1N HCl until pH 1. The mixture was washed with diethyl ether (50 mL) and the acidic aqueous phase was saturated with potassium carbonate. The alkaline mixture was extracted with ethyl acetate (2×100 mL). The combined organic extracts were dried (MgSO$_4$) and the solvent was evaporated. This afforded 3.2 g of 1-cyclopropyl-4-cyanopiperidine. $^1$H NMR (400 MHz, CDCl$_3$) δ 0.37-0.50 (m, 4H), 1.59-1.66 (m, 1H), 1.77-1.94 (m, 4H), 2.4-2.9 (m, 5H).

Step B:

1-Cyclopropyl-N-hydroxypiperidine-4-carboxamidine.

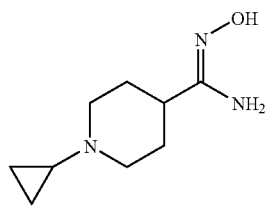

The above nitrile (3.1 g, 21 mmol) was dissolved in ethanol (50 mL) and hydroxylamine hydrochloride (5.7 g, 83 mmol), water (10 mL) and potassium carbonate (6.0 g, 43 mmol) were added. The reaction mixture was stirred 1 h at ambient temperature and then heated overnight at reflux. The mixture was allowed to cool and then concentrated in vacuo. The residue was stirred with water until it had dissolved. Potassium carbonate was added until pH 9 and the alkaline mixture was extracted with ethyl acetate (4×100 mL). The alkaline phase was saturated with sodium chloride and extracted again with ethyl acetate (2×100 mL). The combined ethyl acetate extracts were dried (MgSO$_4$) and the solvent was evaporated. The residue was stirred with acetonitril, isolated by filtration and dried. This afforded 1.2 g of 1-cyclopropyl-N-hydroxy-piperidine-4-carboxamidine. $^1$H NMR (400 MHz, DMSO-d$_6$) δ 0.23-0.29 (m, 2H), 0.37-0.41 (m, 2H), 1.43-1.67 (m, 5H), 1.91-1.1.99 (m, 1H), 2.05-2.13 (m, 2H), 2.89-2.96 (m, 2H), 5.25 (brs, 2H), 8.75 (s, 1H).

Step C:

The above N-hydroxyamidine (0.20 g, 1.1 mmol) was dissolved in glacial acetic acid (10 mL) and 4-tert-butylbenzoyl chloride (0.32 g, 1.6 mmol) was added. The reaction mixture was stirred 3 h at ambient temperature and then heated at reflux for 1 h. The mixture was concentrated in vacuo and the residue was treated with a mixture of water (100 mL) and diethyl ether (50 mL). The ether phase was discarded and the aqueous phase was washed with diethyl ether (2×50 mL). The ether extracts were discarded and the aqueous phase was made alkaline (pH 11) with 4 N sodium hydroxide and then extracted with ethyl acetate (2×100 mL). The combined organic extracts were dried (MgSO$_4$), filtered and with stirring a solution of fumaric acid (0.12 g) in ethanol (10 mL) was added. The volatiles were evaporated and the residue was stirred with diethyl ether to give a solid. The solid was isolated by filtration and dried to give 0.24 g of 4-[5-(4-tert-butylphenyl)[1,2,4]oxadiazol-3-yl]-1-cyclopropylpiperidine as a solid containing two equivalents of fumaric acid. $^1$H NMR (400 MHz, DMSO-d$_6$) δ 0.35-0.48 (m, 4H), 1.33 (s, 9H), 1.66-1.77 (m, 3H), 1.95-2.04 (m, 2H), 2.36-2.45 (m, 2H), 2.85-2.93 (m, 1H), 3.00-3.07 (m, 2H), 6.62 (s, fumarate), 7.65 (d, 2H), 8.02 (d, 2H). HPLC: Rt=17.01 min.

Example 36 (General Procedure (A))

4-(5-Biphenyl-4-yl[1,2,4]oxadiazol-3-yl)-1-cyclopropylpiperidine, Hydrochloride

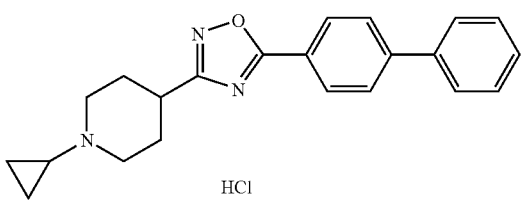

A solid containing the title compound was prepared by a similar procedure to that described in Example 35a, starting from 1-cyclopropyl-N-hydroxypiperidine-4-carboxamidine and 4-phenylbenzoyl chloride.
$^1$H NMR (400 MHz, DMSO-d$_6$, mixture of two isomers) δ 0.75-0.86 (m, 2H), 1.10-1.18 (m, 2H), 2.06-2.39 (m, 4H), 2.76-2.97 (m, 1H), 3.18-3.37 (m, 3H),3.56-3.65 (m, 2H), 7.43-7.47 (m, 1H), 7.54 (t, 2H), 7.78 (d, 2H), 7.92-7.97 (m, 2H), 8.18/8.21 (d, 2H), 10.4/10.6 (brs, 1H). HPLC: Rt=17.62 min.

Example 37 (General Procedure (A))

4-[3-(1-Cyclopropylpiperidin-4-yl)[1,2,4]oxadiazol-5-yl]benzonitrile

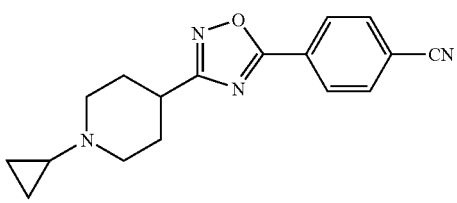

The title compound was prepared by a similar procedure to that described in Example 35a, starting from 1-cyclopropyl-N-hydroxypiperidine-4-carboxamidine and 4-cyanobenzoyl chloride.
$^1$H NMR (400 MHz, CDCl$_3$) δ 0.41-0.50 (m, 4H), 1.62-1.68 (m, 1H), 1.86-1.97 (m, 2H), 2.02-2.12 (m, 2H), 2.33-2.41 (m, 2H), 2.85-2.94 (m, 1H), 3.08-3.18 (m, 2H), 7.83 (d, 2H), 8.23 (d, 2H). HPLC: Rt=9.31 min.

Example 38 (General Procedure (A))

4-(5-Biphenyl-4-yl[1,2,4]oxadiazol-3-yl)-1-(1-ethylpropyl)piperidine

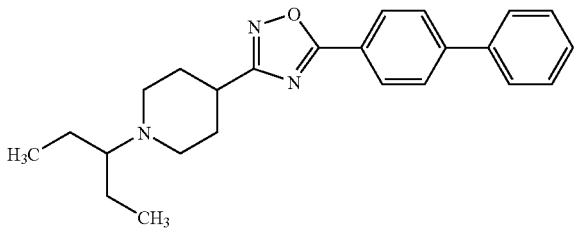

The title compound was prepared by a similar procedure to that described in Example 35a, starting from 1-(1-ethylpropyl)-N-hydroxypiperidine-4-carboxamidine and 4-phenylbenzoyl chloride.
$^1$H NMR (400 MHz, CDCl$_3$) δ 0.93 (t, 6H), 1.26-1.37 (m, 2H), 1.47-1.58 (m, 2H), 1.87-1.96 (m, 2H), 2.03-2.10 (m, 2H), 2.22 (p, 1H), 2.40-2.48 (m, 2H), 2.80-2.89 (m, 3H), 7.41 (t, 1H), 7.48 (t, 2H), 7.64 (d, 2H), 7.73 (d, 2H), 8.18 (d, 2H). HPLC: Rt=20.73 min.

Example 39 (General Procedure (A))

4-(5-Biphenyl-4-ylmethyl[1,2,4]oxadiazol-3-yl)-1-(1-ethylpropyl)piperidine, Hydrochloride

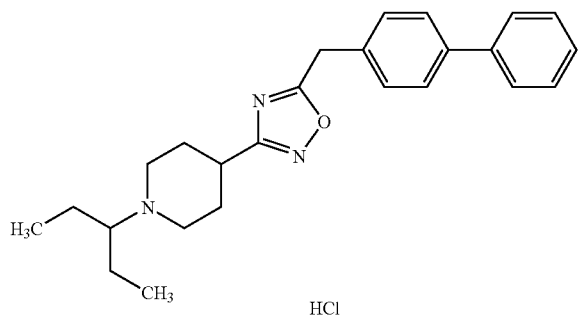

The title compound was prepared by a similar procedure to that described in Example 35a, starting from 1-(1-ethylpropyl)-N-hydroxypiperidine-4-carboxamidine and 4-biphenyl-4-ylacetyl chloride. HPLC: Rt=18.22 min.

Example 40 (General Procedure (D))

4-[5-(4-tert-Butylphenyl)[1,2,4]oxadiazol-3-ylmethyl]-1-cyclopropylpiperidine, Hydrochloride

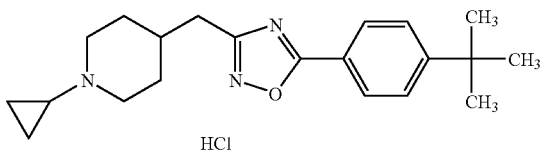

Step A:

4-(N-Hydroxycarbamimidoylmethyl)piperidine-1-carboxylic acid tert-butyl ester.

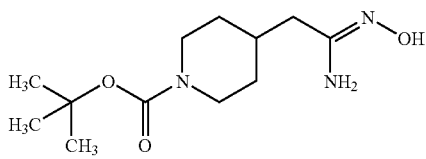

To a solution of 4-(cyanomethyl)piperidine-1-carboxylic acid tert-butyl ester (2.2 g, 10 mmol, prepared as described in Example 12) in absolute ethanol (20 mL) was added hydroxylamine hydrochloride (2.1 g, 30 mmol), water (4 mL) and potassium carbonate (2.2 g, 16 mmol). The reaction mixture was stirred 30 min. at ambient temperature and then heated overnight at reflux for 6 h. Water (10 mL) was added and the mixture was allowed to cool on an ice-bath. The solid inorganic material was removed by filtration and the solvent was evaporated. The residue was treated with dichloromethane, dried and evaporated. The oily residue was submitted to column chromatography (100 g, kiselgel 60) with ethyl acetate as eluent. The fractions eluting at Rf=0.32 were collected to give 0.67 g of 4-(N-hydroxycarbamimidoylmethyl)piperidine-1-carboxylic acid tert-butyl ester. $^1$H NMR (400 MHz, CDCl$_3$) δ 1.07-1.20 (m, 2H), 1.45 (s, 9H), 1.67-1.77 (m, 3H), 2.06 (d, 2H), 2.62-2.77 (m, 2H), 4.1 (brs, 2H), 4.54 (s, 2H), 7.7 (brs, 1H). HPLC: Rt=6.43 min.

Step B:

4-[5-(4-tert-Butylphenyl)[1,2,4]oxadiazol-3-ylmethyl]piperidine.

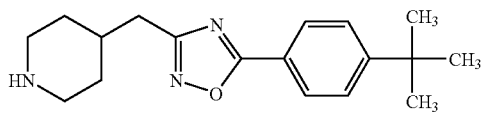

The above N-hydroxyamidine (0.66 g, 2.6 mmol) was dissolved in glacial acetic acid (20 mL) and 4-tert-butylbenzoyl chloride (0.71 g, 3.6 mmol) was added. The reaction mixture was stirred 5 h at ambient temperature and then heated at reflux for 1 h. The mixture was concentrated in vacuo and to the residue was added dichloromethane (10 mL) and trifluoroacetic acid (10 mL). The mixture was stirred at ambient temperature for 1 h. The reaction mixture was evaporated and the residue was dissolved in 1 N hydrochloric acid (15 mL) and water (15 mL) and diethyl ether (30 mL) was added. The diethyl ether phase was discarded and the acidic aqueous phase was washed with diethyl ether (2×10 mL). The ether extracts were discarded and the acidic aqueous phase was made alkaline with 4 N sodium hydroxide and then extracted with ethyl acetate (2×20 mL). The combined organic extracts were dried (MgSO$_4$) and evaporated to give 0.23 g of 4-[5-(4-tert-butylphenyl)[1,2,4]oxadiazol-3-ylmethyl]piperidine. HPLC: Rt=15.81 min.

Step C:

To a solution of the above piperidine (0.23 g, 0.77 mmol) in methanol (1 mL) and THF (3 mL) was added with stirring 1-(ethoxycyclopropoxy)trimethylsilane (0.30 g, 1.7 mmol), glacial acetic acid (0.09 mL) and sodium cyanoborohydride (0.13 g, 2.0 mmol). When addition was complete the mixture was stirred 10 min at ambient temperature and then heated overnight at 65° C. The solvent was evaporated and the residue was dissolved in 0.5 N hydrochloric acid (20 mL) and diethyl ether (15 mL) was added. The mixture was stirred for 30 min and the phases were separated. The acidic aqueous phase was washed with diethyl ether (10 mL) and then 4 N sodium hydroxide was added until pH 10-11. The mixture was extracted with ethyl acetate (2×25 mL). The combined ethyl acetate extracts were dried (MgSO$_4$) and the solvent was evaporated. The oily residue was dissolved in 1 N hydrochloric acid and then evaporated. The residue was re-evaporated with absolute ethanol and then acetonitril. The solid was stirred with diethyl ether, isolated by filtration and dried to give 0.19 g of the title compound. HPLC: Rt=17.88 min Example 41 (General Procedure (E))

Cyclopropyl-{4-[3-(1-cyclopropylpiperidin-4-yl)[1,2,4]oxadiazol-5-yl]phenyl}methanone, Hydrochloride

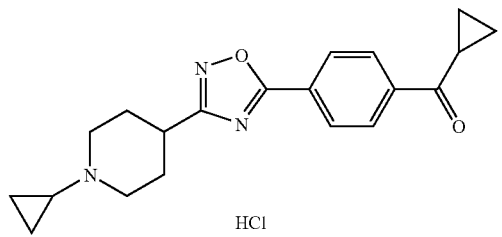

To a Grignard mixture (prepared from magnesium (50 mg, 2.1 mmol) and cyclopropylbromide (211 mg, 1.7 mmol) in dry THF (2 ml)) placed under an atmosphere of nitrogen was added dropwise a solution of 4-[3-(1-cyclopropylpiperidin-4-yl)[1,2,4]oxadiazol-5-yl]benzonitrile (250 mg, 0.85 mmol, prepared as described in Example 37) in dry THF (1.5 ml). When addition was complete the mixture was heated at reflux for 1 h. The mixture was allowed to cool and then saturated ammonium chloride (1 ml) was added. The mixture was extracted with ethyl acetate (15 ml) and the organic phase was dried (MgSO$_4$) and the solvent was evaporated. The residue was dissolved in a mixture of ethanol (10 ml) and 1 N hydrochloric acid (1 ml) and the solvents were evaporated. The residue was re-evaporated with acetonitril and then stirred with ethyl acetate. This afforded 0.23 g containing the title compound. HPLC: Rt=12.45 min.

Example 42 (General Procedure (A))

{4-[3-(1-Cyclopropylpiperidin-4-yl)[1,2,4]oxadiazol-5-yl]phenyl}phenylmethanone

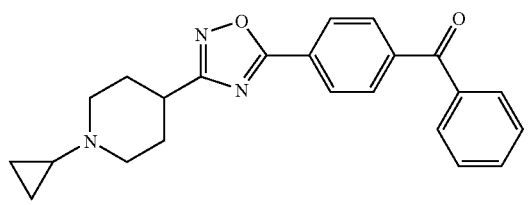

The title compound was prepared by a similar procedure to that described in Example 35a, starting from 1-cyclopropyl-N-hydroxypiperidine-4-carboxamidine and 4-benzoyl-benzoyl chloride.

¹H NMR (400 MHz, CDCl₃) δ 0.42-0.51 (m, 4H), 1.60-1.69 (m, 1H), 1.87-1.98 (m, 2H), 2.06-2.13 (m, 2H), 2.32-2.43 (m, 2H), 2.86-2.94 (m, 1H), 3.11-3.18 (m, 2H), 7.52 (t, 2H), 7.63 (t, 1H), 7.82 (d, 2H), 7.93 (d, 2H), 8.23 (d, 2H). HPLC: Rt=15.62 min.

Example 43 (General Procedure (A))

1-Cyclopropyl-4-[5-(4-trifluoromethoxyphenyl)[1,2,4]oxadiazol-3-yl]piperidine, Hydrochloride

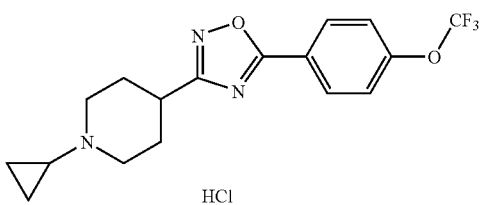

A solid containing the title compound was prepared by a similar procedure to that described in Example 35a, starting from 1-cyclopropyl-N-hydroxypiperidine-4-carboxamidine and 4-trifluoromethoxybenzoyl chloride.

¹H NMR (400 MHz, CDCl₃, mixture of two isomers) δ 0.83-0.93 (m, 2H), 1.62-1.73 (m, 2H), 2.29-2.49 (m, 3H), 2.67-3.86 (m, 7H), 7.35-7.41 (m, 2H), 8.15-8.21 (m, 2H), 12.1/12.35 (brs, 1H). HPLC: Rt=14.59 min.

Example 44 (General Procedure (A))

1-Cyclopropyl-4-[5-(4-trifluoromethylphenyl)[1,2,4]oxadiazol-3-yl]piperidine, Hydrochloride

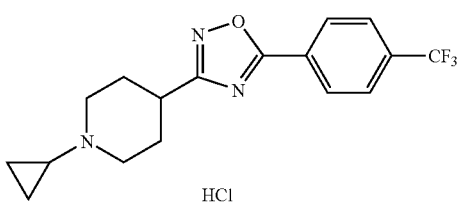

A solid containing the title compound was prepared by a similar procedure to that described in Example 35a, starting from 1-cyclopropyl-N-hydroxypiperidine-4-carboxamidine and 4-trifluoromethylbenzoyl chloride.

¹H NMR (400 MHz, CDCl₃, mixture of two isomers) δ 0.83-0.93 (m, 2H), 1.60-1.75 (m, 2H), 2.31-2.48 (m, 3H), 2.68-3.88 (m, 7H), 7.78-7.84 (m, 2H), 8.23-8.28 (m, 2H), 12.1/12.4 (brs, 1H). HPLC: Rt=13.78 min.

Example 45 (General Procedure (A))

1-Cyclopropyl-4-[5-(4-fluorophenyl)[1,2,4]oxadiazol-3-yl]piperidine, Hydrochloride

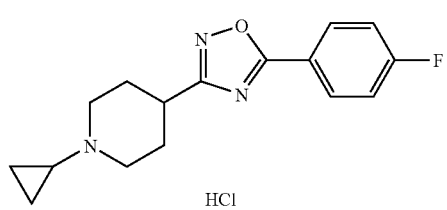

A solid containing the title compound was prepared by a similar procedure to that described in Example 35a, starting from 1-cyclopropyl-N-hydroxypiperidine-4-carboxamidine and 4-fluorobenzoyl chloride.

¹H NMR (400 MHz, CDCl₃, mixture of two isomers) δ 0.83-0.92 (m, 2H), 1.60-1.72 (m, 2H), 2.38-2.48 (m, 3H), 2.66-3.86 (m, 7H), 7.19-7.27 (m, 2H), 8.09-8.17 (m, 2H), 12.0/12.3 (brs, 1H). HPLC: Rt=10.19 min.

Example 46 (General Procedure (A))

1-Cyclopropyl-4-[5-(4-methylphenyl)[1,2,4]oxadiazol-3-yl]piperidine, Hydrochloride

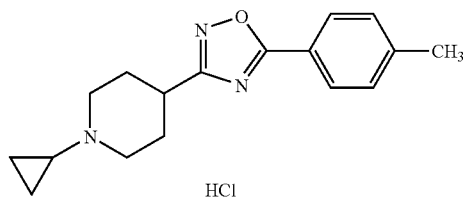

A solid containing the title compound was prepared by a similar procedure to that described in Example 35a, starting from 1-cyclopropyl-N-hydroxypiperidine-4-carboxamidine and 4-methylbenzoyl chloride.

¹H NMR (400 MHz, CDCl₃, mixture of two isomers) δ 0.84-0.91 (m, 2H), 1.60-1.72 (m, 2H), 2.31-2.49 (m, 6H), 2.64-3.85 (m, 7H), 7.30-7.37 (m, 2H), 7.97-8.03 (m, 2H), 12.1/12.3 (brs, 1H). HPLC: Rt=14.09 min.

Example 47 (General Procedure (A))

1-Cyclopropyl-4-[5-(3,4-dichlorophenyl)[1,2,4]oxadiazol-3-yl]piperidine, Hydrochloride

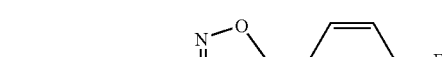

A solid containing the title compound was prepared by a similar procedure to that described in Example 35a, starting from 1-cyclopropyl-N-hydroxypiperidine-4-carboxamidine and 3,4-dichlorobenzoyl chloride.

$^1$H NMR (400 MHz, CDCl$_3$, mixture of two isomers) 0.83-0.93 (m, 2H), 1.60-1.75 (m, 2H), 2.29-2.46 (m, 3H), 2.66-3.78 (m, 7H), 7.60-7.67 (m, 1H), 7.92-7.98 (m, 1H), 8.22 (d, 1H), 12.1/12.4 (brs, 1H). HPLC: Rt=15.22 min.

Example 48 (General Procedure (A))

1-Cyclopropyl-4-[5-(4-chlorophenyl)[1,2,4]oxadiazol-3-yl]piperidine, Hydrochloride

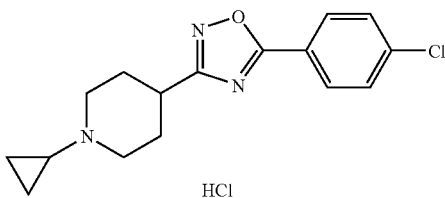

A solid containing the title compound was prepared by a similar procedure to that described in Example 35a, starting from 1-cyclopropyl-N-hydroxypiperidine-4-carboxamidine and 4-chlorobenzoyl chloride.

$^1$H NMR (400 MHz, CDCl$_3$, mixture of two isomers) δ 0.83-0.92 (m, 2H), 1.60-1.73 (m, 2H), 2.29-2.47 (m, 3H), 2.66-3.86 (m, 7H), 7.49-7.56 (m, 2H), 8.04-8.09 (m, 2H), 12.05/12.35 (brs, 1H). HPLC: Rt=12.50 min.

Example 49 (General Procedure (A))

1-Cyclopropyl-4-[5-(4-methoxyphenyl)[1,2,4]oxadiazol-3-yl]piperidine, Hydrochloride

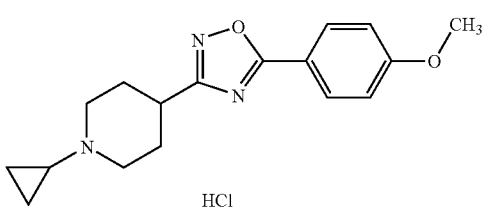

A solid containing the title compound was prepared by a similar procedure to that described in Example 35a, starting from 1-cyclopropyl-N-hydroxypiperidine-4-carboxamidine and 4-methoxybenzoyl chloride.

$^1$H NMR (400 MHz, CDCl$_3$, mixture of two isomers) δ 0.82-0.92 (m, 2H), 1.60-1.73 (m, 2H), 2.29-2.45 (m, 3H), 2.65-3.85 (m, 7H), 3.89/3.90 (s, 3H), 6.98-7.04 (m, 2H), 8.04-8.08 (m, 2H), 12.05/12.35 (brs, 1H). HPLC: Rt=10.85 min.

Example 50 (General Procedure (A))

1-{4-[3-(1-Cyclopropylpiperidin-4-yl)[1,2,4]oxadiazol-5-yl]phenyl}ethanone

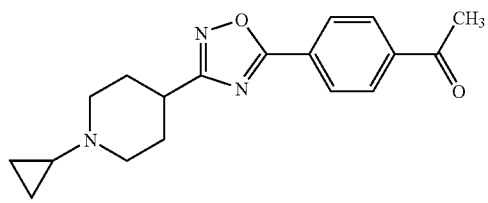

The title compound was prepared by a similar procedure to that described in Example 35a, starting from 1-cyclopropyl-N-hydroxypiperidine-4-carboxamidine and 4-acetylbenzoyl chloride. $^1$H NMR (400 MHz, CDCl$_3$) δ 0.42-0.52 (m, 4H), 1.62-1.68 (m, 1H), 1.86-1.96 (m, 2H), 2.04-2.12 (m, 2H), 2.33-2.39 (m, 2H), 2.67 (s, 3H), 2.85-2.93 (m, 1H), 3.09-3.17 (m, 2H), 8.07 (d, 2H), 8.21 (d, 2H). HPLC: Rt=8.42 min.

Example 51 (General Procedure (A))

1-Cyclopropyl-4-[5-(3-trifluoromethylphenyl)[1,2,4]oxadiazol-3-yl]piperidine, Hydrochloride

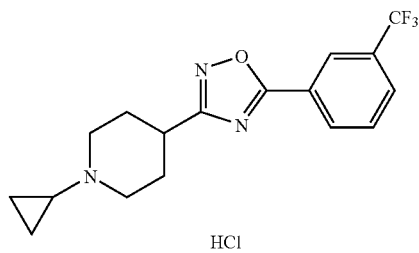

A solid containing the title compound was prepared by a similar procedure to that described in Example 35a, starting from 1-cyclopropyl-N-hydroxypiperidine-4-carboxamidine and 3-trifluoromethylbenzoyl chloride.

$^1$H NMR (400 MHz, CDCl$_3$, mixture of two isomers) δ 0.83-0.95 (m, 2H), 1.60-1.76 (m, 2H), 2.31-2.50 (m, 3H), 2.67-3.88 (m, 7H), 7.66-7.75 (m, 1H), 7.81-7.92 (m, 1H), 8.27-8.42 (m, 2H), 12.1/12.35 (brs, 1H). HPLC: Rt=13.27 min.

Example 52 (General Procedure (A))

1-Cyclopropyl-4-[5-(4-cyclohexylphenyl)[1,2,4]oxadiazol-3-yl]piperidine, Hydrochloride

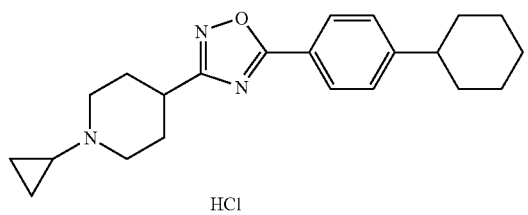

A solid containing the title compound was prepared by a similar procedure to that described in Example 35a, starting from 1-cyclopropyl-N-hydroxypiperidine-4-carboxamidine and 4-cyclohexylbenzoyl chloride.
HPLC: Rt=20.33 min.

Example 53 (General Procedure (A))

1-Cyclopropyl-4-[5-(3,4-difluorophenyl)[1,2,4]oxadiazol-3-yl]piperidine, L-tartrate

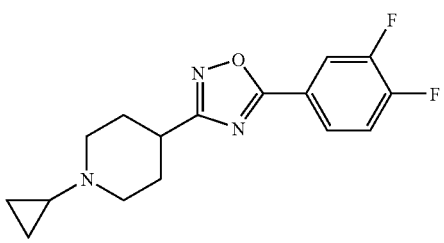

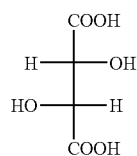

The title compound was prepared as an amorphous solid by a similar procedure to that described in Example 35a, starting from 1-cyclopropyl-N-hydroxypiperidine-4-carboxamidine and 3,4-difluorobenzoyl chloride.
$^1$H NMR (400 MHz, DMSO-$d_6$) δ 0.37-0.49 (m, 4H), 1.65-1.78 (m, 3H), 1.95-2.03 (m, 2H), 2.38-2.47 (m, 2H), 2.86-2.96 (m, 1H), 3.00-3.08 (m, 2H), 4.26 (s, tartrate), 7.66-7.74 (m, 1H), 7.93-8.01 (m, 1H), 8.11-8.16 (m, 1H). HPLC: Rt=10.43 min.

Example 54 (General Procedure (A))

1-Cyclopropyl-4-[5-(3-methoxyphenyl)[1,2,4]oxadiazol-3-yl]piperidine, L-tartrate

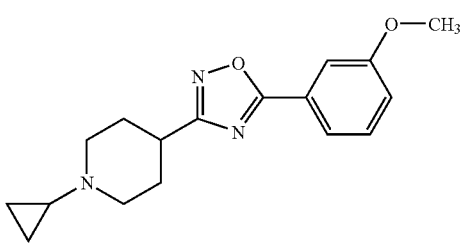

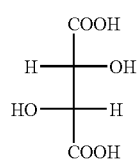

The title compound was prepared as an amorphous solid by a similar procedure to that described in Example 35a, starting from 1-cyclopropyl-N-hydroxypiperidine-4-carboxamidine and 3-methoxybenzoyl chloride.
$^1$H NMR (400 MHz, DMSO-$d_6$) δ 0.35-0.50 (m, 4H), 1.65-1.80 (m, 3H), 1.95-2.03 (m, 2H), 2.38-2.48 (m, 2H), 2.86-2.96 (m, 1H), 3.00-3.09 (m, 2H), 3.86 (s, 3H), 4.27 (s, tartrate), 7.25-7.29 (m, 1H), 7.52-7.57 (m, 2H), 7.66 (d, 1H). HPLC: Rt=10.59 min.

Example 55 (General Procedure (A))

1-Cyclopropyl-4-[5-(3-chloro-4-methoxyphenyl)[1,2,4]oxadiazol-3-yl]piperidine

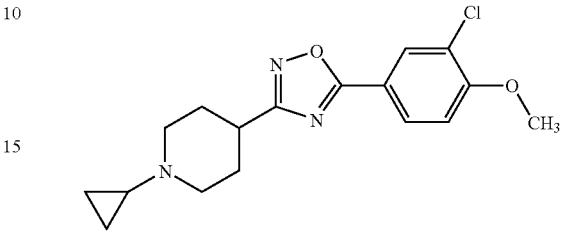

The title compound was prepared by a similar procedure to that described in Example 35a, starting from 1-cyclopropyl-N-hydroxypiperidine-4-carboxamidine and 3-chloro-4-methoxybenzoyl chloride.
$^1$H NMR (400 MHz, CDCl$_3$) δ 0.4-0.5 (m, 4H), 1.6-1.7 (m, 1H), 1.84-1.95 (m, 2H), 2.02-2.09 (m, 2H), 2.30-2.39 (m, 2H), 2.80-2.88 (m, 1H), 3.07-3.15 (m, 2H), 3.98 (s, 3H), 7.03 (d, 1H), 7.98 (d, 1H), 8.13 (s, 1H). HPLC: Rt=12.83 min.

Example 56 (General Procedure (A))

4-(5-Biphenyl-4-yl[1,2,4]oxadiazol-3-yl)-1-isopropylpiperidine, Hydrochloride

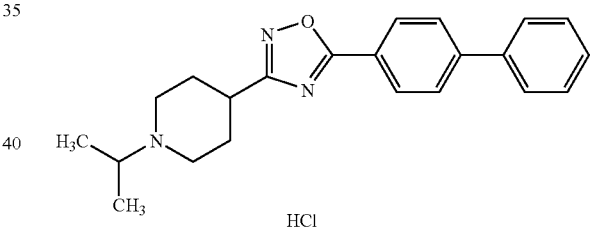

Step A:

1-Isopropyl-4-cyanopiperidine.

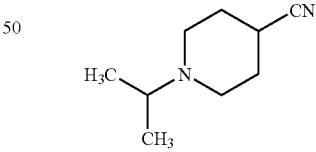

To a solution of 4-cyanopiperidine (5.8 g, 53 mmol, J. Org. Chem. 21, 984-986, 1957) in methanol (30 mL) and THF (130 mL) was added with stirring acetone (7.7 mL) and glacial acetic acid (6.0 mL) followed by portion wise addition of sodium cyanoborohydride (6.6 g, 105 mmol). When addition was complete the mixture was stirred overnight at ambient temperature. The solvent was evaporated and to the residue was added 1N hydrochloric (110 mL) until pH 1. The mixture was washed with diethyl ether (100 mL) and the acidic aqueous phase was saturated with potassium carbonate. The alkaline mixture (pH 10) was extracted with ethyl acetate (2×200 mL). The combined organic extracts were dried (MgSO₄) and the solvent was evaporated. This afforded 8.2 g of 1-isopropyl-4-cyanopiperidine. ¹H NMR 400 MHz, DMSO-d₆) δ 0.96 (d, 6H), 1.63-1.73 (m, 2H), 1.80-1.92 (m, 2H), 2.35-2.44 (m, 2H), 2.58-2.67 (m, 2H), 2.69-2.78 (m, 1H), 2.79-2.87 (m, 1H).

Step B:

1-Isopropyl-N-hydroxypiperidine-4-carboxamidine.

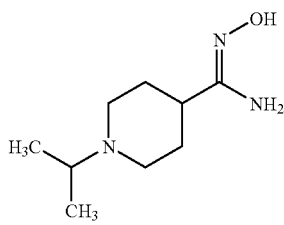

The above nitrile (7.0 g, 46 mmol) was dissolved in ethanol (150 mL) and hydroxylamine hydrochloride (18 g, 259 mmol), water (30 mL) and potassium carbonate (18.2 g, 132 mmol) were added. The reaction mixture was stirred 1 h at ambient temperature and then heated overnight at reflux. The mixture was then concentrated in vacuo and re-evaporated with absolute ethanol. The residue was boiled with absolute ethanol (500 mL) and filtered hot. This was repeated with another portion of absolute ethanol (400 mL). The combined ethanolic filtrates were evaporated in vacuo to give a residue that was dissolved in ethanol (150 mL). Some solid material was removed by filtration and the filtrate was reduced in vacuo. The solid residue was stirred with cold absolute ethanol (20 mL), filtered and dried. This afforded 3.5 g of 1-isopropyl-N-hydroxypiperidine-4-carboxamidine. ¹H NMR (400 MHz, DMSO-d₆) δ 0.93 (d, 6H), 1.46-1.60 (m, 2H), 1.62-1.70 (m, 2H), 1.85-1.93 (m, 1H), 2.00-2.10 (m, 2H), 2.58-2.69 (m, 1H), 2.75-2.82 (m, 2H), 5.23 (s, 2H), 8.73 (s, 1H).

Step C:

The above N-hydroxyamidine (0.20 g, 1.08 mmol) was dissolved in glacial acetic acid (15 mL) and 4-phenylbenzoyl chloride (0.35 g, 1.62 mmol) was added. The reaction mixture was stirred 24 h at ambient temperature and then heated at reflux for 1 h. The mixture was concentrated in vacuo and the residue was treated with a mixture of water (100 mL) and diethyl ether (30 mL). The ether phase was discarded and the aqueous phase was washed with di-ethyl ether (2×20 mL). The ether extracts were discarded and the aqueous phase was made alkaline (pH 10-11) with 4 N sodium hydroxide and then extracted with ethyl acetate (2×50 mL). The combined organic extracts were dried (MgSO₄), evaporated and the residue was dissolved in 1 N hydrochloric acid. The volatiles were removed in vacuo and the residue was re-evaporated with acetonitril and then stirred with a small portion of ethyl acetate. After filtration and drying this afforded 90 mg of the title compound as a solid.

¹H NMR (400 MHz, CDCl₃, mixture of two isomers) δ1.45/1.51 (d, 6H), 2.23-2.45 (m, 2H), 2.77-3.21 and 3.32-3.65 (m, 8H), 7.39-7.52 (m, 3H), 7.63-7.66 (m, 2H), 7.72-7.80 (m, 2H), 8.18 (d, 2H), 12.1/12.4 (brs, 1H). HPLC: Rt=18.09 min.

Example 57 (General Procedure (A))

1-Isopropyl-4-[5-(4-methoxyphenyl)[1,2,4]oxadiazol-3-yl]piperidine, Hydrochloride

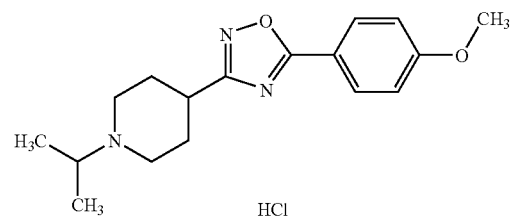

The title compound was prepared by a similar procedure to that described in Example 56, starting from 1-isopropyl-N-hydroxypiperidine-4-carboxamidine and 4-methoxybenzoyl chloride.

¹H NMR (400 MHz, CDCl₃, mixture of two isomers) δ1.44/1.49 (d, 6H), 2.32-2.41 (m, 2H), 2.72-3.20 and 3.29-3.62 (m, 8H), 3.88 (s, 3H), 6.99 (d, 2H), 8.03 (d, 2H), 12.0/12.3 (brs, 1H).

HPLC: Rt=10.79 min.

Example 58 (General Procedure (A))

1-Isopropyl-4-[5-cyclohexyl[1,2,4]oxadiazol-3-yl]piperidine, Hydrochloride

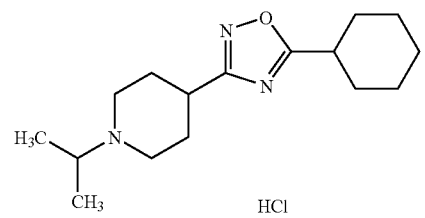

The title compound was prepared by a similar procedure to that described in Example 56, starting from 1-isopropyl-N-hydroxypiperidine-4-carboxamidine and cyclohexanecarbonyl chloride.

¹H NMR (400 MHz, CDCl₃, mixture of two isomers) δ 1.23-1.53 (m, 10H), 1.54-1.66 (m, 2H), 1.67-1.76 (m, 1H), 1.78-1.87 (m, 2H), 2.00-2.10 (m, 2H), 2.22-2.40 (m, 2H), 2.63-3.16 and 3.27-3.59 (m, 8H), 12.0/12.3 (brs, 1H). HPLC: Rt=9.86 min.

Example 59 (General Procedure (A))

1-Isopropyl-4-[5-(4-cyclohexylphenyl)[1,2,4]oxadiazol-3-yl]piperidine

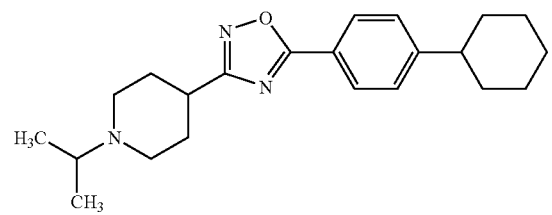

The title compound was prepared by a similar procedure to that described in Example 56, starting from 1-isopropyl-N-hydroxypiperidine-4-carboxamidine and 4-cyclohexylbenzoyl chloride.

$^1$H NMR (400 MHz, CDCl$_3$)ε 1.06 (d, 6H), 1.20-1.33 (m, 1H), 1.35-1.50 (m, 4H), 1.73-2.14 (m, 9H), 2.25-2.34 (m, 2H), 2.53-3.00 (m, 5H), 7.33 (d, 2H), 8.02 (d, 2H). HPLC: Rt=20.85 min.

Example 60 (General Procedure (A))

1-Isopropyl-4-[5-(4-tert-butylcyclohexyl)[1,2,4]oxadiazol-3-yl]piperidine, Hydrochloride

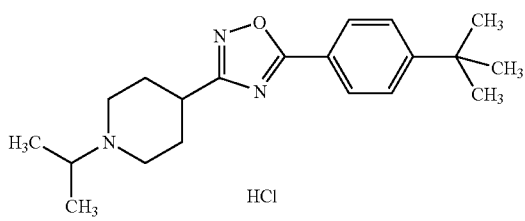

The title compound was prepared by a similar procedure to that described in Example 56, starting from 1-isopropyl-N-hydroxypiperidine-4-carboxamidine and 4-tert-butylcyclohexanecarbonyl chloride.

HPLC: Rt=18.96 min.

Example 61 (General Procedure (A))

1-{4-[3-(1-Isopropylpiperidin-4-yl)[1,2,4]oxadiazol-5-yl]phenyl}ethanone, Hydrochloride

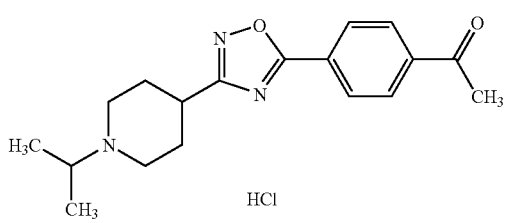

The title compound was prepared by a similar procedure to that described in Example 56, starting from 1-isopropyl-N-hydroxypiperidine-4-carboxamidine and 4-acetylbenzoyl chloride.

$^1$H NMR (400 MHz, CDCl$_3$, mixture of two isomers) δ 1.45/1.51 (d, 6H), 2.34-2.43 (m, 2H), 2.67/2.68 (s, 3H), 2.76-3.18 and 3.33-3.64 (m, 8H), 8.06-8.13 (m, 2H), 8.19-8.25 (m, 2H), 12.1/12.35 (brs, 1H). HPLC: Rt=8.93 min.

Example 62 (General Procedure (A))

1-Isopropyl-4-[5-(4-butylphenyl)[1,2,4]oxadiazol-3-yl]piperidine, Hydrochloride

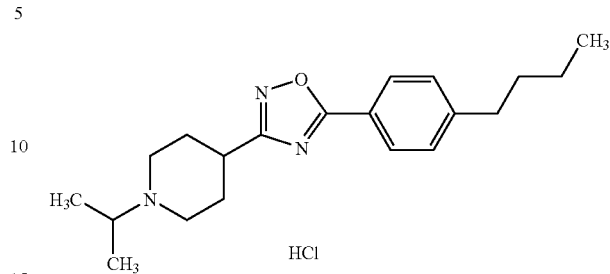

The title compound was prepared by a similar procedure to that described in Example 56, starting from 1-isopropyl-N-hydroxypiperidine-4-carboxamidine and 4-butylbenzoyl chloride.

HPLC: Rt=19.38 min.

Example 63 (General Procedure (A))

1-Isopropyl-4-[5-(4-ethylphenyl)[1,2,4]oxadiazol-3-yl]piperidine, Hydrochloride

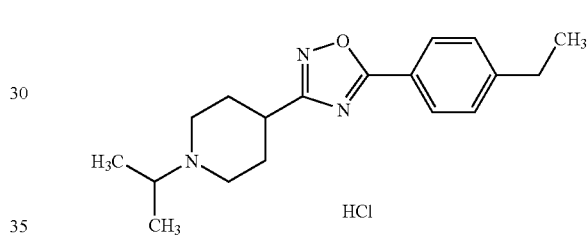

The title compound was prepared by a similar procedure to that described in Example 56, starting from 1-isopropyl-N-hydroxypiperidine-4-carboxamidine and 4-ethylbenzoyl chloride.

HPLC: Rt=14.62 min.

Example 64 (General Procedure (A))

1-Isopropyl-4-[5-methyl[1,2,4]oxadiazol-3-yl]piperidine, Hydrochloride

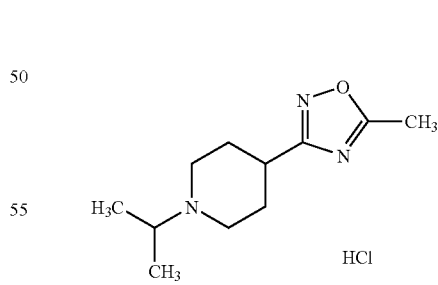

The title compound was prepared by a similar procedure to that described in Example 56, starting from 1-isopropyl-N-hydroxypiperidine-4-carboxamidine and acetic anhydride.

$^1$H NMR (400 MHz, CDCl$_3$, mixture of two isomers) δ 1.43/1.48 (d, 6H), 2.23-2.36 (m, 2H), 2.57/2.60 (s, 3H), 2.66-3.12 and 3.27-3.60 (m, 8H), 12.0/12.3 (brs, 1H). HPLC: Rt=3.47 min.

Example 65 (General Procedure (A))

1-Isopropyl-4-[5-(2-cyclopentylethyl)[1,2,4]oxadiazol-3-yl]piperidine, Hydrochloride

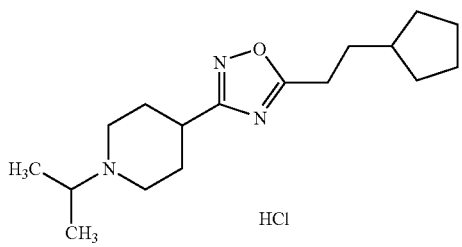

The title compound was prepared by a similar procedure to that described in Example 56, starting from 1-isopropyl-N-hydroxypiperidine-4-carboxamidine and 3-cyclopentyl) propanoyl chloride.

$^1$H NMR (400 MHz, CDCl$_3$, mixture of two isomers) δ 1.05-1.20 (m, 2H), 1.43/1.49 (d, 6H), 1.50-1.68 (m, 4H), 1.74-1.88 (m, 5H), 2.23-2.38 (m, 2H), 2.64-3.13 and 3.27-3.58 (m, 10H), 12.0/12.3 (brs, 1H). HPLC: Rt=13.80 min.

Example 66 (General Procedure (D))

1-Methyl-4-(5-(biphen-4-yl)-[1,2,4]oxadiazol-3-yl) piperidine, Methanesulfonate

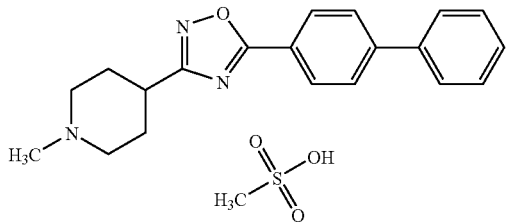

Step A:

4-(N-Hydroxycarbamimidoyl)piperidine-1-carboxylic acid tert-butyl ester.

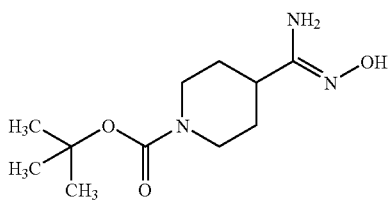

To a solution of 4-cyanopiperidine-1-carboxylic acid tert-butyl ester (10.5 g, 50 mmol) in ethanol (125 mL) was added hydroxylamine hydrochloride (10.4 g, 150 mmol), potassium carbonate (11.1 g, 80 mmol) and water (25 mL). The resulting mixture was stirred at ambient temperature for 1 h and then heated at reflux overnight. The reaction mixture was allowed to cool, filtered and the filter cake was washed thoroughly with ethanol. The filtrate was evaporated to give a solid residue that was boiled with absolute ethanol (400 mL). The mixture was allowed to cool and then filtered. The filtrate was evaporated to dryness and the resulting solid was stirred with ethyl acetate (100 mL). The solid was isolated and dried to give 10.5 g of 4-(hydroxycarbamimidoyl) piperidine-1-carboxylic acid tert-butyl ester.

Step B:

4-(5-(Biphen-4-yl)-[1,2,4]oxadiazol-3-yl)piperidine, Methanesulfonate

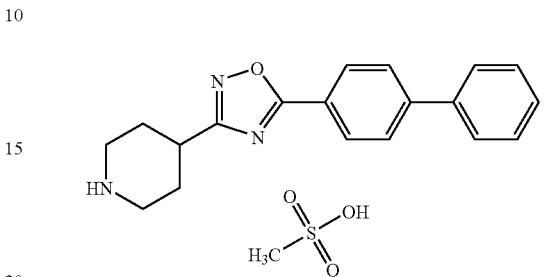

To a stirred solution of the above N-hydroxyamidine (1.2 g, 5 mmol) in glacial acetic acid (40 mL) was added 4-biphenylcarbonyl chloride (1.4 g, 6.5 mmol). The reaction mixture was stirred overnight at ambient temperature and then heated at reflux for 1 h. The mixture was concentrated and the residue was treated with a mixture of 1 N hydrochloric acid (200 mL) and diethyl ether (100 mL). The diethyl ether phase was discarded and the aqueous phase containing some solid material was washed with diethyl ether (100 mL). The diethyl ether extract was discarded and with stirring the aqueous phase was made alkaline (pH 11) with 4 N sodium hydroxide and then extracted with ethyl acetate (2×200 mL). The combined organic extracts were dried (MgSO$_4$) and the volatiles were evaporated to give 0.9 g of a solid that was dissolved in ethyl acetate (90 mL). Methanesulfonic acid (0.065 mL) was added and the resulting mixture was stirred for 2 h. The solid was isolated and dried to give 1.1 g of 4-(5-(biphen-4-yl)-[1,2,4]oxadiazol-3-yl)piperidine, methanesulfonate.

Mp.=229-232° C. $^1$H NMR (300 MHz, CDCl$_3$, mixture of two isomers) δ 2.25-2.47 (m, 4H), 2.85 (s, 3H), 3.12-3.28 (m, 3H), 3.50-3.62 (m, 2H), 7.38-7.52 (m, 3H), 7.63-7.67 (m, 2H), 7.76 (d, 2H), 8.17 (d, 2H), 8.85/8.95 (brs, 1H). Microanalysis for C$_{19}$H$_{19}$N$_3$O, CH$_3$SO$_3$H: Calc: C, 59.83%; H, 5.77%; N, 10.47%; Found: C, 59.66%; H, 5.57%, N, 10.43%.

Step C:

To a solution of 4-(5-(biphen-4-yl)-[1,2,4]oxadiazol-3-yl) piperidine, methanesulfonate (250 mg, 0.82 mmol) in methanol (3 mL) was added with stirring an aqueous solution of formaldehyde (37%, 0.2 mL). A solution, prepared from sodium cyanoborohydride (55 mg) in methanol (2.5 mL) and anhydrous ZnCl$_2$ (60 mg), was added dropwise. When addition was complete the mixture was stirred at ambient temperature for 2 h and 0.1 N hydrochloric acid (6 mL) was added. The resulting mixture was filtered and the filter cake was washed thoroughly with water. The solid was dried overnight and then treated with ethyl acetate (30 mL). The mixture was filtered and to the filtrate was added methanesulfonic acid (0.060 mL). The resulting solid was isolated and dried to give 250 mg of the title compound.

Mp.=222-224° C. $^1$H NMR (300 MHz, CDCl$_3$, mixture of two isomers) δ 2.36-2.73 (m, 3H), 2.83-2.98 (m, 7H), 3.03-3.18 (m, 2H), 3.45-3.60 (m, 2H), 3.75-3.84 (m, 1H), 7.37-7.53 (m, 3H), 7.62-7.67 (m, 2H), 7.72-7.80 (m, 2H), 8.15-8.20 (m, 2H), 10.95/11.15 (brs, 1H). Microanalysis for C$_{20}$H$_{21}$N$_3$O, CH$_3$SO$_3$H, 0.25H$_2$O: Calc: C, 60.05%; H, 6.12%; N, 10.00%; Found: C, 59.82%; H, 5.76%, N, 9.89%.

Example 67 (General Procedure (A))

1-Isopropyl-3-(5-(biphen-4-yl)-[1,2,4]oxadiazol-3-yl)piperidine, Hydrochloride

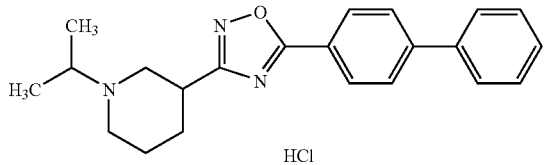

The title compound was prepared by a similar procedure to that described in Example 56, starting from 1-isopropylpiperidine-3-carbonitril and 4-phenylbenzoyl chloride.

$^1$H NMR (300 MHz, CDCl$_3$, mixture of isomers) δ 1.51/1.53 (d, 6H), 1.62-1.77 (m, 1H), 1.98-2.09 (m, 1H), 2.44-2.57 (m, 1H), 2.65-2.86 (m, 2H), 2.92-3.04 (m, 1H), 3.46-3.60 (m, 2H), 3.77-3.85 (m, 1H), 4.11-4.24 (m, 1H), 7.38-7.54 (m, 3H), 7.65 (d, 2H), 7.76 (d, 2H), 8.17 (d, 2H), 12.5 (brs, 1H). HPLC: Rt=15.05 min.

Example 68 (General Procedure (F))

1-Isopropyl-4-(3-(biphen-4-yl)-[1,2,4]oxadiazol-5-yl)piperidine, Hydrochloride

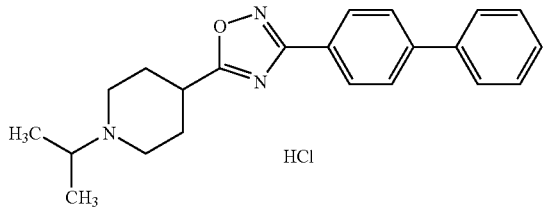

Step A:
4-(3-(Biphen-4-yl)-[1,2,4]oxadiazol-5-yl)piperidine

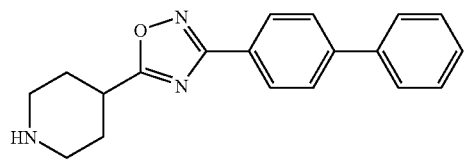

A mixture of N-hydroxy-biphenyl-4-carboxamidine (0.42 g, 2.0 mmol), piperidine-1,4-dicarboxylic acid 1-tert-butyl ester 4-ethyl ester (0.64 g, 2.5 mmol), absolute ethanol (40 mL) and sodium ethoxide (0.16 g, 2.3 mmol) was stirred at ambient temperature for 1 h, heated shortly at 50° C. and then stirred overnight at ambient temperature. Then the mixture was heated at reflux temperature for 1 day and then another portion of piperidine-1,4-dicarboxylic acid 1-tert-butyl ester 4-ethyl ester (0.70 g) was added. Heating at reflux temperature was continued for another 3 days and the mixture was neutralized with acetic acid. The volatiles were removed in vacuo and the residue was treated with a mixture of ethyl acetate (50 mL) and water (20 mL). The phases were separated and the organic phase was washed with water (20 mL), dried (MgSO$_4$) and the volatiles were evaporated to give an oil that was submitted to column chromatography (150 g, kiselgel 60, mesh 0.040-0.063) with a mixture of ethyl acetate and heptane (1:1) as eluent. The fractions eluting at Rf=0.72 were collected to give 0.77 g of a mixture of 4-(3-biphenyl-4-yl-[1,2,4]oxadiazol-5-yl)piperidine-1-carboxylic acid tert-butyl ester and the starting piperidine-1,4-dicarboxylic acid 1-tert-butyl ester 4-ethyl ester according to NMR. This mixture was dissolved in dichloromethane (20 mL) and trifluoroacetic acid was added (20 mL). The reaction mixture was stirred at ambient temperature for 30 minutes and the volatiles were evaporated. The residue was dissolved in dichloromethane (50 mL), 1 N sodium hydroxide (50 mL) was added and the mixture was stirred for 1 h. The phases were separated and the organic phase was washed with water (10 mL), dried and evaporated to give 0.29 g of 4-(3-(biphen-4-yl)-[1,2,4]oxadiazol-5-yl)piperidine.

$^1$H NMR (300 MHz, CDCl$_3$) δ 1.82-1.97 (m, 2H), 2.09-2.19 (m, 2H), 2.75-2.86 (m, 2H), 3.10-3.27 (m, 3H), 7.38 (t, 1H), 7.47 (t, 2H), 7.64 (d, 2H), 7.71 (d, 2H), 8.15 (d, 2H).

Step B:
The above 4-(3-(biphen-4-yl)-[1,2,4]oxadiazol-5-yl)piperidine (0.29 g) was dissolved in a mixture of tetrahydrofuran (2.7 mL) and methanol (0.62 mL). Acetone (0.12 mL), glacial acetic acid (0.083 mL) and sodium cyanoborohydride (92 mg) was added and the mixture was stirred at ambient temperature overnight. The volatiles were evaporated and the residue was stirred with a mixture of 0.5 N sodium hydroxide (10 mL) and ethyl acetate (30 mL). The phases were separated and the organic phase was washed with water and dried (MgSO$_4$). The volatiles were evaporated and the residue was stirred with 1 N hydrochloric acid (5 mL). The mixture was evaporated to give a solid residue that was stirred with a small portion of acetonitril, filtered and dried. This afforded 80 mg of the title compound.

$^1$H NMR (300 MHz, CDCl$_3$, mixture of two isomers) δ 1.46/1.50 (d, 6H), 2.35-2.60 (m, 2H), 2.72-3.28 and 3.36-3.69 (m, 8H), 7.35-7.53 (m, 3H), 7.60-7.77 (m, 4H), 8.13 (d, 2H), 12.25/12.50 (brs, 1H). HPLC: Rt=14.66 min.

Example 69 (General Procedure (A))

1-Isopropyl-3-(5-(4'-chlorobiphen-4-yl)-[1,2,4]oxadiazol-3-yl)piperidine, Hydrochloride

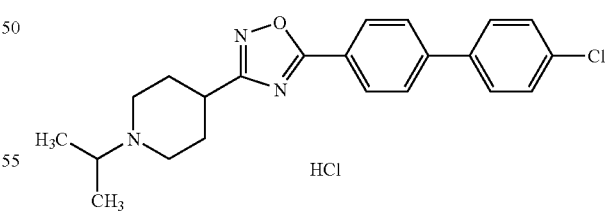

The title compound was prepared by a similar procedure to that described in Example 56, starting from 1-isopropyl-N-hydroxypiperidine-4-carboxamidine and 4-(4-chlorophenyl)benzoyl chloride.

$^1$H NMR (300 MHz, CDCl$_3$, mixture of two isomers) δ 1.45/1.50 (d, 6H), 2.33-2.45 (m, 2H), 2.77-3.23 and 3.30-3.66 (m, 8H), 7.43-7.50 (m, 2H), 7.55-7.61 (m, 2H), 7.69-7.77 (m, 2H), 8.18 (d, 2H), 12.1/12.4 (brs, 1H). HPLC: Rt=19.95 min.

The following compounds of the invention are prepared in accordance with the general procedures described.

Example 70

1-Isopropyl-4-(5-(4'-fluorobiphen-4-yl)-[1,2,4]oxadiazol-3-yl)piperidine

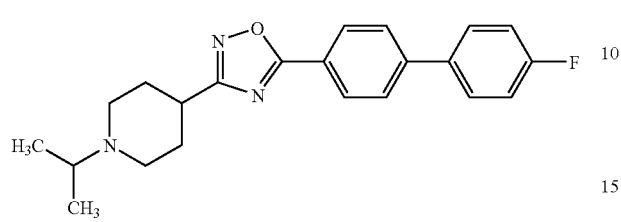

Example 71

1-Isopropyl-4-(5-(4'-methoxybiphen-4-yl)-[1,2,4]oxadiazol-3-yl)piperidine

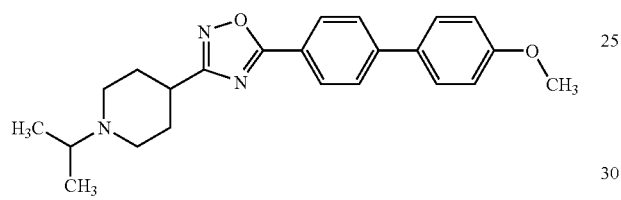

Example 72

1-Isopropyl-4-(5-(2'-chlorobiphen-4-yl)-[1,2,4]oxadiazol-3-yl)piperidine

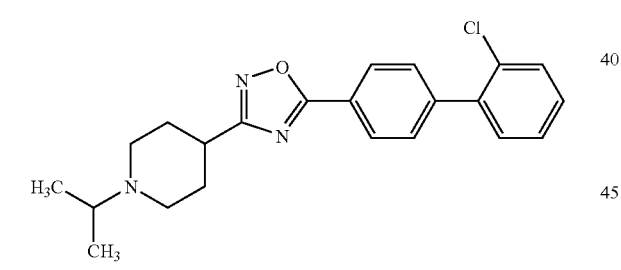

Example 73

1-Isopropyl-4-(5-(2'-methoxybiphen-4-yl)-[1,2,4]oxadiazol-3-yl)piperidine

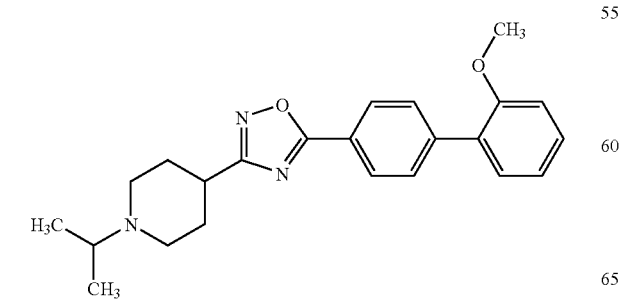

Example 74

1-Isopropyl-4-(5-(2'-fluorobiphen-4-yl)-[1,2,4]oxadiazol-3-yl)piperidine

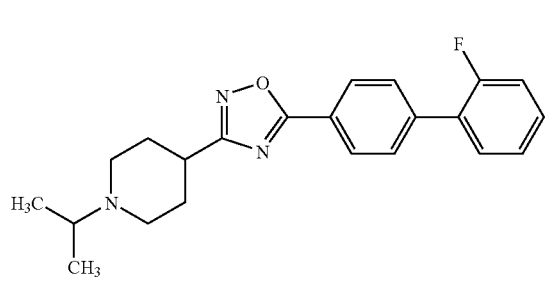

Example 75

1-Isopropyl-4-(5-(3'-fluorobiphen-4-yl)-[1,2,4]oxadiazol-3-yl)piperidine

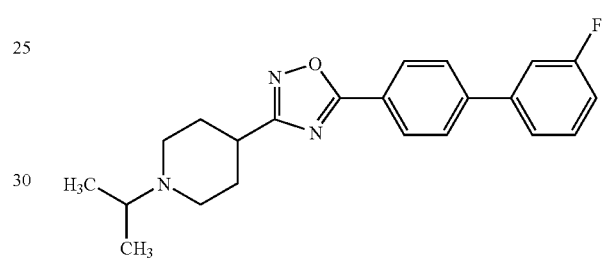

Example 76

1-Isopropyl-4-(5-(4'-trifluoromethylbiphen-4-yl)-[1,2,4]oxadiazol-3-yl)piperidine

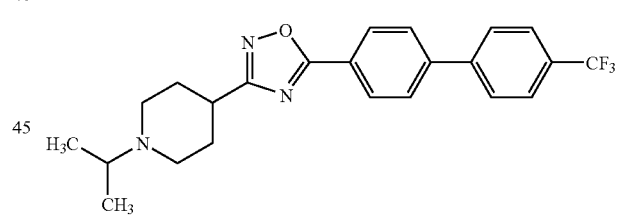

Example 77

1-Isopropyl-4-(5-(4'-trifluoromethoxybiphen-4-yl)-[1,2,4]oxadiazol-3-yl)piperidine

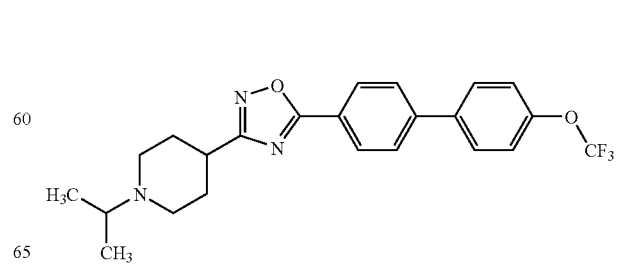

Example 78

1-Isopropyl-4-(5-(biphen-4-yl)-[1,3,4]oxadiazol-2-yl)piperidine

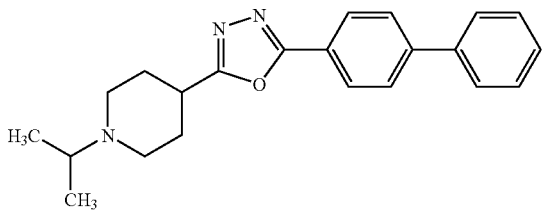

Example 79

1-Isopropyl-4-(5-(biphen-4-yl)-[1,2,4]triazol-3-yl)piperidine

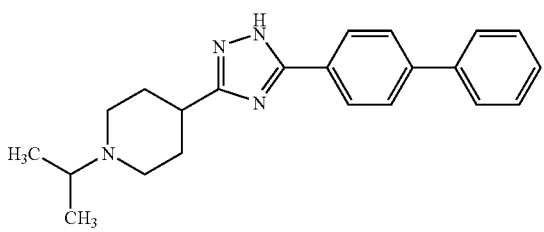

Example 80

1-Isopropyl-4-(5-(biphen-4-yl)-2-methyl-[1,2,4]triazol-3-yl)piperidine

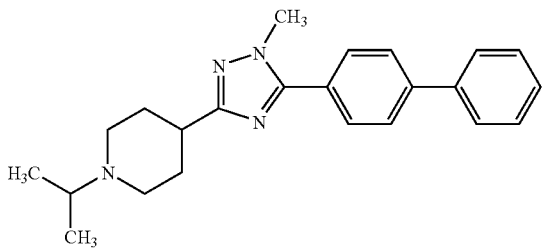

Example 81

1-Isopropyl-4-(5-(biphen-4-yl)-1-methyl-[1,2,4]triazol-3-yl)piperidine

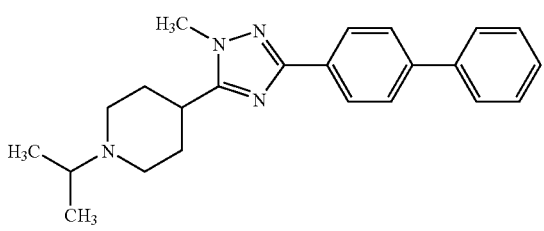

Pharmacological Methods

The ability of the compounds to interact with the histamine H3 receptor can be determined by the following in vitro binding assays.

Binding Assay I

The H3-receptor agonist ligand R-α-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter.

Male Wistar rats (150-200 g) are decapitated and cerebral cortex is quickly dissected out and frozen immediately on dry ice. Tissue is kept at −80° C. until membrane preparation. During the membrane preparation the tissue is kept on ice all the time. Rat cerebral cortex is homogenized in 10 volumes (w/w) ice-cold Hepes buffer (20 mM Hepes, 5 mM MgCl$_2$ pH 7.1 (KOH)+1 mg/mL bacitracin) using an Ultra-Turrax homogenizer for 30 seconds. The homogenate is centrifuged at 140 g in 10 min. The supernatant is transferred to a new test tube and centrifuged for 30 min at 30 000 g. Pellet is resuspended in 5-10 mL Hepes buffer, homogenized and centrifuged for 10 min at 30 000 g. This short centrifugation step is repeated twice. After the last centrifugation the pellet is resuspended in 2-4 mL Hepes buffer and the protein concentration is determined. The membranes are diluted to a protein concentration of 5 mg/mL using Hepes buffer, aliquoted and stored at −80° C. until use.

50 μl test-compound, 100 μl membrane (200 μg/mL), 300 μl Hepes buffer and 50 μl R-α-methyl[$^3$H]histamine (1 nM) are mixed in a test tube. The compounds to be tested are dissolved in DMSO and further diluted in H$_2$O to the desired concentrations. Radioligand and membranes are diluted in Hepes buffer +1 mg/mL bacitracin. The mixture is incubated for 60 min at 25° C. Incubation is terminated by adding 5 mL ice-cold 0.9% NaCl, followed by rapid filtration through Whatman GF/B filters pre-treated for 1 hour with 0.5% polyethyleneimine. The filters are washed with 2×5 mL ice-cold NaCl. To each filter a 3 mL scintillation cocktail is added and the radioactivity retained is measured with a Packard Tri-Carb beta counter.

IC$_{50}$ values are calculated by non-linear regression analysis of binding curves (6 points minimum) using the windows program GraphPad Prism, GraphPad software, USA.

Binding Assay II

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/mL G 418 at 37° C. and 5% CO$_2$. Before harvesting, the confluent cells are rinsed with PBS and incubated with Versene (proteinase, GIBCO-BRL) for approximately 5 min. The cells are flushed with PBS and DMEM and the cell suspension collected in a tube and centrifuged for 5-10 min at 420 g in a Heraeus Sepatech Megafuge 1.0. The pellet is resuspended in 10-20 vol. Hepes buffer (20 mM Hepes, 5 mM MgCl$_2$, pH 7.1 (KOH)) and homogenized for 10-20 seconds using an Ultra-Turrax homogenizer. The homogenate is centrifuged for 30 min at 30 000 g. The pellet is resuspended in 5-10 mL Hepes buffer, homogenized 5-10 seconds with the Ultra-Turrax and centrifuged for 10 min at 30 000 g. Following this centrifugation step, the membrane pellet is resuspended in 2-4 mL Hepes buffer, homogenized with a syringe or Teflon homogenizer, and the protein concentration determined. The membranes are diluted to a protein concentration of 1-5 mg/mL in Hepes buffer, aliquoted and kept at −80° C. until use.

Aliquots of the membrane suspension are incubated for 60 min at 25° C. with 30 pM [$^{125}$I]-iodoproxifan, a known compound with high affinity for the H3 receptor, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analysed by nonlinear regression analysis.

When tested, the present compounds of the formula (I) generally show a high binding affinity to the histamine H3 receptor.

Functional Assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/mL G418 at 37° C. and 5% $CO_2$.

The H3 receptor expressing cells are washed once with phosphate buffered saline (PBS) and harvested using versene (GIBCO-BRL). PBS is added and the cells are centrifuged for 5 min at 364 g. The cell pellet is resuspended in stimulation buffer to a concentration of $1\times10^6$ cells/mL. cAMP accumulation is measured using the Flash Plate® cAMP assay (NEN™ Life Science Products). The assay is generally performed as described by the manufacturer. Briefly, 50 µl cell suspension is added to each well of the Flashplate which also contained 25 µl 40 µM isoprenaline, to stimulate cAMP generation, and 25 µl of test compound (either agonists or inverse agonists alone, or agonist and antagonist in combination). The assay can be run in "agonist-mode" which means that the test compound is added, in increasing concentration, on its own, to the cells, and cAMP is measured. If cAMP goes up, it is an inverse agonist; if cAMP does not change, it is a neutral antagonist, and if cAMP goes down, it is an agonist. The assay can also be run in the "antagonist-mode" which means that a test compound is added, in increasing concentrations, together with increasing concentrations of a known H3 agonist (eg RAMHA). If the compound is an antagonist, increasing concentrations of it cause a right-ward shift in the H3 agonist's dose-response curves. The final volume in each well is 100 µl. Test compounds are dissolved in DMSO and diluted in $H_2O$. The mixture is shaken for 5 min, and allowed to stand for 25 min at room temperature. The reaction is stopped with 100 µl "Detection Mix" per well. The plates are then sealed with plastic, shaken for 30 min, allowed to stand overnight, and finally the radio-activity is counted in the Cobra II auto gamma top counter. $EC_{50}$ values are calculated by non-linear regression analysis of dose response curves (6 points minimum) using GraphPad Prism. Kb values are calculated by Schild plot analysis.

Functional Assay II

The ability of the compounds to bind and interact with the human, monkey or rat H3 receptor as agonists, inverse agonists and/or antagonists, is determined by a functional assay, named [$^{35}$S] GTPγS assay.

Met-Glu-Arg-Ala-Pro-Pro-Asp-Gly-Pro-Leu-Asn-Ala-
Ser-Gly-Ala-Leu-Ala-Gly-Glu-Ala-Ala-Ala-Ala-Gly-
Gly-Ala-Arg-Gly-Phe-Ser-Ala-Ala-Trp-Thr-Ala-Val-
Leu-Ala-Ala-Leu-Met-Ala-Leu-Leu-Ile-Val-Ala-Thr-
Val-Leu-Gly-Asn-Ala-Leu-Val-Met-Leu-Ala-Phe-Val-
Ala-Asp-Ser-Ser-Leu-Arg-Thr-Gln-Asn-Asn-Phe-Phe-
Leu-Leu-Asn-Leu-Ala-Ile-Ser-Asp-Phe-Leu-Val-Gly-
Ala-Phe-Cys-Ile-Pro-Leu-Tyr-Val-Pro-Tyr-Val-Leu-
Thr-Gly-Arg-Trp-Thr-Phe-Gly-Arg-Gly-Leu-Cys-Lys-
Leu-Trp-Leu-Val-Val-Asp-Tyr-Leu-Leu-Cys-Thr-Ser-
Ser-Ala-Phe-Asn-Ile-Val-Leu-Ile-Ser-Tyr-Asp-Arg-
Phe-Leu-Ser-Val-Thr-Arg-Ala-Val-Ser-Tyr-Arg-Ala-
Gln-Gln-Gly-Asp-Thr-Arg-Arg-Ala-Val-Arg-Lys-Met-
Leu-Leu-Val-Trp-Val-Leu-Ala-Phe-Leu-Leu-Tyr-Gly-
Pro-Ala-Ile-Leu-Ser-Trp-Glu-Tyr-Leu-Ser-Gly-Gly-
Ser-Ser-Ile-Pro-Glu-Gly-His-Cys-Tyr-Ala-Glu-Phe-
Phe-Tyr-Asn-Trp-Tyr-Phe-Leu-Ile-Thr-Ala-Ser-Thr-
Leu-Glu-Phe-Phe-Thr-Pro-Phe-Leu-Ser-Val-Thr-Phe-
Phe-Asn-Leu-Ser-Ile-Tyr-Leu-Asn-Ile-Gln-Arg-Arg-
Thr-Arg-Leu-Arg-Leu-Asp-Gly-Ala-Arg-Glu-Ala-Ala-
Gly-Pro-Glu-Pro-Pro-Pro-Glu-Ala-Gln-Pro-Ser-Pro-
Pro-Pro-Pro-Pro-Gly-Cys-Trp-Gly-Cys-Trp-G

-continued

Arg-Ala-Phe-Thr-Lys-Leu-Leu-Cys-Pro-Gln-Lys-Leu-
Lys-Ile-Gln-Pro-His-Ser-Ser-Leu-Glu-His-Cys-Trp-
Lys.

Met-Glu-Arg-Ala-Pro-Pro-Asp-Gly-Pro-Leu-Asn-Ala-
Ser-Gly-Ala-Leu-Ala-Gly-Glu-Ala-Ala-Ala-Gly-
Gly-Ala-Arg-Gly-Phe-Ser-Ala-Ala-Trp-Thr-Ala-Val-
Leu-Ala-Ala-Leu-Met-Ala-Leu-Leu-Ile-Val-Ala-Thr-
Val-Leu-Gly-Asn-Ala-Leu-Val-Met-Leu-Ala-Phe-Val-
Ala-Asp-Ser-Ser-Leu-Arg-Thr-Gln-Asn-Asn-Phe-Phe-
Leu-Leu-Asn-Leu-Ala-Ile-Ser-Asp-Phe-Leu-Val-Gly-
Ala-Phe-Cys-Ile-Pro-Leu-Tyr-Val-Pro-Tyr-Val-Leu-
Thr-Gly-Arg-Trp-Thr-Phe-Gly-Arg-Gly-Leu-Cys-Lys-
Leu-Trp-Leu-Val-Val-Asp-Tyr-Leu-Leu-Cys-Thr-Ser-
Ser-Ala-Phe-Asn-Ile-Val-Leu-Ile-Ser-Tyr-Asp-Arg-
Phe-Leu-Ser-Val-Thr-Arg-Ala-Val-Ser-Tyr-Arg-Ala-
Gln-Gln-Gly-Asn-Thr-Arg-Arg-Ala-Val-Arg-Lys-Met-
Leu-Leu-Val-Trp-Val-Leu-Ala-Phe-Leu-Leu-Tyr-Gly-
Pro-Ala-Ile-Leu-Ser-Trp-Glu-Tyr-Leu-Ser-Gly-Gly-
Ser-Ser-Ile-Pro-Glu-Gly-His-Cys-Tyr-Ala-Glu-Phe-
Phe-Tyr-Asn-Trp-Tyr-Phe-Leu-Ile-Thr-Ala-Ser-Thr-
Leu-Glu-Phe-Phe-Thr-Pro-Phe-Leu-Ser-Val-Thr-Phe-
Phe-Asn-Leu-Ser-Ile-Tyr-Leu-Asn-Ile-Gln-Arg-Arg-
Thr-Arg-Leu-Arg-Leu-Asp-Gly-Ala-Arg-Glu-Ala-Gly-
Gly-Pro-Glu-Pro-Pro-Glu-Ala-Gln-Pro-Ser-Pro-
Pro-Pro-Pro-Pro-Gly-Cys-Trp-Gly-Cys-Trp-Gln-Lys-
Gly-His-Gly-Glu-Ala-Met-Pro-Leu-His-Arg-Tyr-Gly-
Val-Gly-Glu-Ala-Ala-Ala-Gly-Ala-Glu-Ala-Gly-Glu-
Thr-Ala-Leu-Gly-Gly-Gly-Gly-Gly-Gly-Ser-Ala-
Ala-Ser-Pro-Thr-Ser-Ser-Ser-Gly-Ser-Ser-Ser-Arg-
Gly-Thr-Glu-Arg-Pro-Arg-Ser-Leu-Lys-Arg-Gly-Ser-
Lys-Pro-Ser-Ala-Ser-Ser-Ala-Ser-Leu-Glu-Lys-Arg-
Met-Lys-Met-Val-Ser-Gln-Ser-Phe-Thr-Gln-Arg-Phe-
Arg-Leu-Ser-Arg-Asp-Arg-Lys-Val-Ala-Lys-Ser-Leu-
Ala-Val-Ile-Val-Ser-Ile-Phe-Gly-Leu-Cys-Trp-Ala-
Pro-Tyr-Thr-Leu-Leu-Met-Ile-Ile-Arg-Ala-Ala-Cys-
His-Gly-His-Cys-Val-Pro-Asp-Tyr-Trp-Tyr-Glu-Thr-
Ser-Phe-Trp-Leu-Leu-Trp-Ala-Asn-Ser-Ala-Val-Asn-
Pro-Val-Leu-Tyr-Pro-Leu-Cys-His-His-Ser-Phe-Arg-
Arg-Ala-Phe-Thr-Lys-Leu-Leu-Cys-Pro-Gln-Lys-Leu-

-continued

Lys-Ile-Gln-Pro-His-Ser-Ser-Leu-Glu-Gln-Cys-Trp-
Lys.

Met-Glu-Arg-Ala-Pro-Pro-Asp-Gly-Leu-Met-Asn-Ala-
Ser-Gly-Thr-Leu-Ala-Gly-Glu-Ala-Ala-Ala-Gly-
Gly-Ala-Arg-Gly-Phe-Ser-Ala-Ala-Trp-Thr-Ala-Val-
Leu-Ala-Ala-Leu-Met-Ala-Leu-Leu-Ile-Val-Ala-Thr-
Val-Leu-Gly-Asn-Ala-Leu-Val-Met-Leu-Ala-Phe-Val-
Ala-Asp-Ser-Ser-Leu-Arg-Thr-Gln-Asn-Asn-Phe-Phe-
Leu-Leu-Asn-Leu-Ala-Ile-Ser-Asp-Phe-Leu-Val-Gly-
Ala-Phe-Cys-Ile-Pro-Leu-Tyr-Vag-Pro-Tyr-Val-Leu-
Thr-Gly-Arg-Trp-Thr-Phe-Gly-Arg-Gly-Leu-Cys-Lys-
Leu-Trp-Leu-Val-Val-Asp-Tyr-Leu-Leu-Cys-Ala-Ser-
Ser-Val-Phe-Asn-Ile-Val-Leu-Ile-Ser-Tyr-Asp-Arg-
Phe-Leu-Ser-Val-Thr-Arg-Ala-Val-Ser-Tyr-Arg-Ala-
Gln-Gln-Gly-Asp-Thr-Arg-Arg-Ala-Val-Arg-Lys-Met-
Ala-Leu-Val-Trp-Val-Leu-Ala-Phe-Leu-Leu-Tyr-Gly-
Pro-Ala-Ile-Leu-Ser-Trp-Glu-Tyr-Leu-Ser-Gly-Gly-
Ser-Ser-Ile-Pro-Glu-Gly-His-Cys-Tyr-Ala-Glu-Phe-
Phe-Tyr-Asn-Trp-Tyr-Phe-Leu-Ile-Thr-Ala-Ser-Thr-
Leu-Glu-Phe-Phe-Thr-Pro-Phe-Leu-Ser-Val-Thr-Phe-
Phe-Asn-Leu-Ser-Ile-Tyr-Leu-Asn-Ile-Gln-Arg-Arg-
Thr-Arg-Leu-Arg-Leu-Asp-Gly-Gly-Arg-Glu-Ala-Gly-
Pro-Glu-Pro-Pro-Pro-Asp-Ala-Gln-Pro-Ser-Pro-Pro-
Pro-Ala-Pro-Pro-Ser-Cys-Trp-Gly-Cys-Trp-Pro-Lys-
Gly-His-Gly-Glu-Ala-Met-Pro-Leu-His-Arg-Tyr-Gly-
Val-Gly-Glu-Ala-Gly-Pro-Gly-Val-Glu-Ala-Gly-Glu-
Ala-Ala-Leu-Gly-Gly-Gly-Ser-Gly-Gly-Gly-Ala-Ala-
Ala-Ser-Pro-Thr-Ser-Ser-Ser-Gly-Ser-Ser-Ser-Arg-
Gly-Thr-Glu-Arg-Pro-Arg-Ser-Leu-Lys-Arg-Gly-Ser-
Lys-Pro-Ser-Ala-Ser-Ser-Ala-Ser-Leu-Clu-Lys-Arg-
Met-Lys-Met-Val-Ser-Gln-Ser-Ile-Thr-Gln-Arg-Phe-
Arg-Leu-Ser-Arg-Asp-Lys-Lys-Val-Ala-Lys-Ser-Leu-
Ala-Ile-Ile-Val-Ser-Ile-Phe-Gly-Leu-Cys-Trp-Ala-
Pro-Tyr-Thr-Leu-Leu-Met-Ile-Ile-Arg-Ala-Ala-Cys-
His-Gly-Arg-Cys-Ile-Pro-Asp-Tyr-Trp-Tyr-Glu-Thr-
Ser-Phe-Trp-Leu-Leu-Trp-Ala-Asn-Ser-Ala-Val-Asn-
Pro-Val-Leu-Tyr-Pro-Leu-Cys-His-Tyr-Ser-Phe-Arg-
Arg-Ala-Phe-Thr-Lys-Leu-Leu-Cys-Pro-Gln-Lys-Leu-

-continued

Lys-Val-Gln-Pro-His-Gly-Ser-Leu-Glu-Gln-Cys-Trp-Lys.

The assay measures the activation of G proteins by catalyzing the exchange of guanosine 5′-diphosphate (GDP) by guanosine 5′-triphosphate (GTP) at the α-subunit. The GTP-bounded G proteins dissociate into two subunits, Gα$_{GTP}$ and Gβγ, which in turn regulate intracellular enzymes and ion channels. GTP is rapidly hydrolysed by the Gα-subunit (GTPases) and the G protein is deactivated and ready for a new GTP exchange cycle. To study the function of ligand induced G protein coupled receptor (GPCR) activation by an increase in guanine nucleotide exchange at the G proteins, the binding of [$^{35}$S]-guanosine-5′-O-(3-thio) triphosphate ([$^{35}$S] GTPγS), a non-hydrolysed analogue of GTP, is determined. This process can be monitored in vitro by incubating cell membranes containing the G protein coupled receptor H3 with GDP and [$^{35}$S] GTPγS. Cell membranes are obtained from CHO cells stably expressing the human H3 receptor or from HEK 293 cells stably expressing the rat or monkey H3 receptor. The cells are washed twice in PBS, harvested with PBS+1 mM EDTA, pH 7.4 and centrifuged at 280 g for 5 min. The cell pellet is homogenized in 10 mL ice-cold Hepes buffer (20 mM Hepes, 10 mM EDTA pH 7.4 (NaOH)) using an Ultra-Turrax homogenizer for 30 seconds and centrifuged for 15 min at 30,000 g. Following this centrifugation step, the membrane pellet is resuspended in 10 mL ice-cold Hepes buffer (20 mM Hepes, 0.1 mM EDTA pH 7.4 (NaOH)) and homogenized as describe above. This procedure is repeated twice except for the last homogenization step, the protein concentration is determined and membranes are diluted to a protein concentration of 2 mg/mL, aliquoted and kept at −80° C. until use.

In order to study the presence and the potency of an inverse agonist/antagonist the H3-receptor agonist ligand R-α-methyl histamine (RAMHA) is added. The ability of the test compound to counteract the effect of RAMHA is measured. When studying the effect of an agonist RAMHA is not added to the assay medium. The test compound is diluted in the assay buffer (20 mM HEPES, 120 mM NaCl, 10 mM MgCl$_2$ pH 7.4 (NaOH)) at various concentrations followed by addition of 10$^{-8}$ nM RAMHA (only in the case where an inverse agonist/antagonist is examined), 3 μM GDP, 2.5 μg membranes, 0.5 mg SPA beads and 0.1 nM [$^{35}$S] GTPγS and incubated for 2 hours by slightly shaking at room temperature. For the rat and monkey H3 receptor 10 μg membranes including 10 μg/mL saponin are used. The plates are centrifuged at 420 g for 10 min and the radioactivity is measured using a Top-counter. The results are analyzed by non linear regression and the IC$_{50}$ value is determined.

RAMHA and other H3 agonists stimulate the binding of [$^{35}$S] GTPγS to membranes expressing the H3 receptor. In the antagonist/inverse agonist test, the ability of increasing amounts of test compound to inhibit the increased [$^{35}$S] GTPγS binding by 10$^{-8}$ M RAMHA is measured as a decrease in radioactivity signal. The IC$_{50}$ value determined for an antagonist is the ability of this compound to inhibit the effect of 10$^{-8}$ M RAMHA by 50%. In the agonist test, the ability of increasing amounts of test compound is measured as an increase in radio-activity signal. The EC$_{50}$ value determined for an agonist, is the ability of this compound to increase the signal by 50% of the maximal signal that is obtained by 10$^{-5}$ M RAMHA.

Preferably, the antagonists and agonists according to the invention have an IC$_{50}$/EC$_{50}$ value as determined by one or more of the assays of less than 10 μM, more preferred of less than 1 μM, and even more preferred of less than 500 nM, such as of less than 100 nM.

The Open Cage Schedule-Fed Rat Model

The ability of the present compounds to reduce weight is determined using the in vivo open cage Schedule-fed rat model.

Sprague-Dawley (SD) male rats of an age of about 1½ to 2 months and a weight of about 200-250 g are purchased from Møllegård Breeding and Research Centre A/S (Denmark). On arrival they are allowed some days of acclimatisation before being placed in individual open plastic cages. They are habituated to the presence of food (Altromin pelleted rat chow) in their home cage only during 7 hours in the morning from 07.30 to 14.30 all days a week. Water is present ad libitum. As the consumption of food has stabilised after 7 to 9 days, the animals are ready for use.

Each animal is used only once to avoid carry-over effects between treatments. During the test sessions, the test compound is administered intraperitoneally or orally 30 min before the start of the sessions. One group of animals is administered the test compound at different doses and a control group of animals is given a vehicle. Food and water intake are monitored at 1, 2 and 3 hours post administration.

Any side effects may rapidly be discovered (barrel-rolling, bushy fur etc.) since the animals are kept in transparent plastic cages to enable continuous monitoring.

The invention claimed is:

1. A compound of the general formula (I):

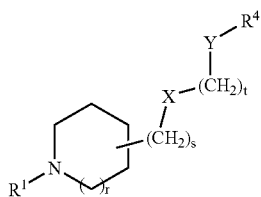

(I)

wherein

R¹ is $C_{3-8}$-cycloalkyl or $C_{5-8}$-cycloalkenyl,
  wherein the cyclic moieties may optionally be substituted with one or more substituents independently selected from $R^{12}$, wherein $R^{12}$ is $C_{1-6}$-alkyl, halogen, trifluoromethyl or 2,2,2-trifluoroethyl, r is 1, s is 0, 1, 2 or 3, t is 0, 1, 2 or 3, X is C=O, CHOH or $CR^2R^3$; wherein $R^2$ and $R^3$ independently are hydrogen or $C_{1-6}$-alkyl, or X is a bond, Y is is selected from the group consisting of oxadiazolyl, thiadiazolyl, or triazolyl, optionally substituted with one or more substituents independently selected from $R^{18}$, $R^{18}$ is halogen, nitro, cyano, hydroxy, $C_{1-6}$-alkyl, $C_{1-6}$-alkylthio or $C_{1-6}$-alkoxy;

$R^4$ is (a) $C_{1-6}$-alkyl, $C_{3-8}$-cycloalkyl or $C_{3-8}$-cycloalkenyl, which may optionally be substituted with one or more substituents independently selected from $R^{13}$, wherein $R^{13}$ is $C_{3-8}$-cycloalkyl, $C_{1-6}$-alkoxy, $C_{1-6}$-alkylthio, cyano, halo-$C_{1-6}$-alkyl, halo-$C_{1-6}$alkoxy, and halogen, or (b) aryl, aryl-$C_{1-6}$-alkyl, aryl-$C_{2-4}$-alkenyl, or heteroaryl
  which may optionally be substituted with one or more substituents independently selected from $R^{14}$ $R^{14}$ is halogen, nitro, cyano, acyl, hydroxy, $C_{1-6}$-alkyl, $C_{1-6}$-alkylthio, $C_{1-6}$-alkylsulfonyl, $C_{1-6}$-alkylsulfonyloxy, $C_{1-6}$-alkoxy, $C_{3-8}$-cycloalky, halo-$C_{1-6}$-alkyl, halo-$C_{1-6}$-alkoxy, —$NR^5R^6$, $R^5R^6N$—$C_{1-6}$-alkyl-, $R^5R^6N$—$C_{1-6}$-alkoxy-, or —O(C=) $NR^5R^6$, or wherein two substituents in adjacent positions together form a radical —O—$(CH_2)_{1-3}$-O—, wherein $R^5$ and $R^6$ independently are hydrogen, $C_{1-6}$-alkyl, $C_{3-8}$-cycloalkyl, $C_{1-6}$-alkanoyl or aryl, or $R^5$ and $R^6$ together with the nitrogen atom to which they are attached form a 3 to 7 membered, saturated or unsaturated ring, which may be fused to a benzene ring, a group of the formula —$(W)_k$-A wherein W is —$C_{1-6}$-alkyl-, —$(O)_l$—$C_{2-6}$-alkenyl-, —$(O)_l$—$C_{1-6}$-alkyl-O—, —$(CH_2)_n$—(C=O)—$CH_2)_m$—, —O— wherein l is 0 or 1 k is 0 or 1 n and m are independently 0, 1, 2 or 3,

A is aryl, aryl -$C_{1-6}$-alkyl, heteroaryl, heteroaryl-$C_{1-6}$-alkyl, $C_{1-6}$-alkyl or $C_{3-8}$-cycloalkyl wherein the ring moieties optionally may be substituted with one or more substituents independently selected from $R^{15}$ $R^{15}$ is halogen, nitro, cyano, hydroxy, $C_{1-6}$-alkylthio, $C_{1-6}$-alkylsulfonyl, $C_{1-6}$-alkylsulfonyloxy, $C_{1-6}$-alkyl, $C_{1-6}$-alkoxy, $C_{3-8}$-cycloalkyl, halo-$C_{1-6}$-alkyl, halo-$C_{1-6}$-alkoxy, —$NR^7R^8$, $R^7R^8N$—$C_{1-6}$-alkyl-, $R^7R^8N$—$C_{1-6}$-alkoxy-, or —O(C=O)NR$^7$R$^8$, or wherein two substituents in adjacent positions together form a radical O—(CH$_2$)$_{1-3}$—O—,
wherein R$^7$ and R$^8$ independently are hydrogen, C$_{1-6}$-alkyl, C$_{3-8}$-cycloalkyl, C$_{1-6}$-alkanoyl or aryl, or R$^7$ and R$^8$ together with the nitrogen atom to which they are attached form a 3 to 7 membered, saturated or unsaturated ring, which may be fused to a benzene ring,
NR$^9$R$^{10}$ wherein R$^9$ and R$^{10}$ independently are hydrogen, C$_{1-6}$-alkyl, C$_{3-8}$-cycloalkyl, C$_{1-6}$-alkanoyl or aryl, or R$^9$ and R$^{10}$ together with the nitrogen atom to which they are attached form a 3 to 7 membered, saturated or unsaturated ring, which may be fused to a benzene ring, and the ring may contain further heteroatoms and it may optionally be substituted with one or more substituents independently selected from R$^{16}$, wherein R$^{16}$ is C$_{1-6}$-alkyl, C$_{3-8}$-cycloalkyl, C$_{1-6}$-alkanoyl or aryl optionally substituted with one or more substituents independently selected from R$^{17}$, wherein R$^{17}$ is halogen, nitro, cyano, hydroxy, or C$_{1-6}$-alkyl;

as well as any diastereomer or enantiomer or tautomeric form, mixtures of these, or a pharmaceutically acceptable salt thereof.

2. A compound according to claim 1, wherein R$^1$ is C$_{3-8}$-cycloalkyl.

3. A compound according to claim 2 wherein R$^1$ is cyclopropyl, cyclobutyl, cyclopentyl, or cyclohexyl.

4. A compound according to claim 3 wherein R$^1$ is cyclopropyl or cyclopentyl.

5. A compound according to claim 4 wherein R$^1$ is cylopropyl.

6. A compound according to claim 1, wherein X is a bond.

7. A compound according to claim 1, wherein s and t together are 0, 1, 2 or 3.

8. A compound according to claim 1 wherein s is 0 or 1.

9. A compound according to claim 8 wherein s is 0.

10. A compound according to claim 1 wherein t is 0.

11. A compound according to claim 1, wherein Y is selected from

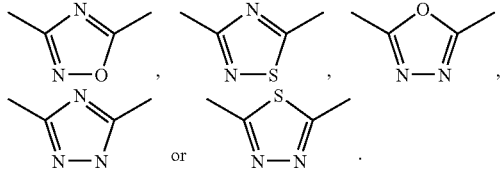

12. A compound according to claim 1, wherein R$^4$ is aryl, aryl-C$_{1-6}$-alkyl, either of which may optionally be substituted with one or more substituents independently selected from R$^{14}$, or C$_{3-8}$-cycloalkyl optionally substituted with one or more substituents independently selected from R$^{13}$.

13. A compound according to claim 12 wherein R$^4$ is aryl optionally substituted with one or more substituents independently selected from R$^{14}$.

14. A compound according to claim 12 wherein R$^4$ is phenyl, biphenylyl, or naphthyl optionally substituted with one or more substituents independently selected from R$^{14}$.

15. A compound according to claim 14, wherein R$^4$ is phenyl optionally substituted with one or more substituents independently selected from R$^{14}$.

16. A compound according to claim 1 wherein R$^{13}$ is C$_{1-6}$-alkyl.

17. A compound according to claim 1 wherein R$^{14}$ is halogen, cyano, hydroxy, C$_{1-6}$-alkyl, C$_{1-6}$-alkylsulfonyl, C$_{1-6}$-alkylsulfonyloxy, C$_{1-6}$-alkoxy, C$_{3-8}$-cycloalkyl, —CF$_3$, —OCF$_3$, —NR$^5$R$^6$, R$^5$R$^6$N—C$_{1-6}$-alkyl-, or a group of the formula —(W)$_k$-A.

18. A compound according to claim 17 wherein R$^{14}$ is F, Cl, cyano, methyl, ethyl, propyl, butyl, tert-butyl, methyl-sulfonyl, methyl-sulfonyloxy, methoxy, ethoxy, cyclopropyl, cyclobutyl, cyclopentyl, cyclohexyl, —CF$_3$, —OCF$_3$, —NR$^5$R$^6$, R$^5$R$^6$N-methyl-, or a group of the formula -(W)$_k$-A.

19. A compound according to claim 18 wherein R$^{14}$ is F, Cl, cyano, methyl, tert-butyl, methyl-sulfonyl, methoxy, cyclopentyl, cyclohexyl, —CF$_3$, —OCF$_3$, —NR$^5$R$^6$, R$^5$R$^6$N-methyl-, or
a group of the formula -(W)$_k$-A.

20. A compound according to claim 19 wherein R$^{14}$ is a group of the formula -(W)$_k$-A.

21. A compound according to claim 1, wherein k is 1.

22. A compound according to claim 1 wherein k is 0.

23. A compound according to claim 1 wherein W is —C$_{1-6}$-alkyl-, —(O)$_l$—C$_{1-6}$-alkyl-O—, —(CH$_2$)$_n$—(C=O)—(CH$_2$)$_m$—, or —O—.

24. A compound according to claim 23 wherein W is —C$_{1-6}$-alkyl- or —(CH$_2$)$_n$—(C=O)—(CH$_2$)$_m$—.

25. A compound according to claim 24 wherein W is methylene, ethylene, propylene or —(CH$_2$)$_n$—(C=O)—(CH$_2$)$_m$—.

26. A compound according to claim 1 wherein n is 0 or 1.

27. A compound according to claim 26 wherein n is 0.

28. A compound according to claim 1 wherein m is 0 or 1.

29. A compound according to claim 28 wherein m is 0.

30. A compound according to claim 1 wherein l is 0.

31. A compound according to claim 1 wherein A is C$_{1-6}$-alkyl, aryl or C$_{3-8}$-cycloalkyl, wherein the ring moieties optionally may be substituted with one or more substituents independently selected from R$^{15}$, or A is NR$^9$R$^{10}$.

32. A compound according to claim 31 wherein A is methyl, ethyl, phenyl, cyclopropyl, cyclobutyl, cyclopentyl, or cyclohexyl, wherein the ring moieties optionally may be substituted with one or more substituents independently selected from R$^{15}$, or A is NR$^9$R$^{10}$.

33. A compound according to claim 32 wherein A is phenyl optionally substituted with one or more substituents independently selected from R$^{15}$.

34. A compound according to claim 33 wherein A is phenyl.

35. A compound according to claim 32 wherein A is NR$^9$R$^{10}$.

36. A compound according to claim 1 wherein R$^{15}$ is halogen, nitro, cyano, hydroxy, C$_{1-6}$-alkylthio, C$_{1-6}$-alkylsulfonyl, C$_{1-6}$-alkylsulfonyloxy, C$_{1-6}$-alkyl, C$_{1-6}$-alkoxy, C$_{3-8}$-cycloalkyl, halo-C$_{1-6}$-alkyl, or halo-C$_{1-6}$-alkoxy.

37. A compound according to claim 36 wherein R$^{15}$ is halogen, cyano, hydroxy, CH$_3$—S—, CH$_3$CH$_2$—S—, methylsulfonyl, methylsulfonyloxy, methyl, ethyl, propyl, butyl, isopropyl, methoxy, ethoxy, cyclopropyl, cyclobutyl, cyclopentyl, or cyclohexyl, —CF$_3$, or —OCF$_3$.

38. A compound according to claim 37 wherein R$^{15}$ is halogen, methyl, ethyl, methoxy, ethoxy, —CF$_3$, or —OCF$_3$.

39. A compound according to claim 1 wherein R$^9$ and R$^{10}$ together with the nitrogen atom to which they are attached form a 3 to 7 membered, saturated or unsaturated ring, which may be fused to a benzene ring, and the ring may contain further heteroatoms and it may optionally be substituted with one or more substituents independently selected from R$^{16}$.

40. A compound according to claim 39 wherein $R^9$ and $R^{10}$ together with the nitrogen atom to which they are attached form a structure selected from

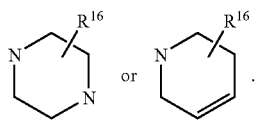

41. A compound according to claim 1 wherein $R^{16}$ is methyl, ethyl, 1-ethyl-propyl or phenyl optionally substituted with one or more substituents independently selected from $R^{17}$.

42. A compound according to claim 1 wherein $R^{17}$ is halogen.

43. A pharmaceutical composition comprising, as an active ingredient, at least one compound according to claim 1 together with one or more pharmaceutically acceptable carriers or excipients.

44. A pharmaceutical composition according to claim 43 in unit dosage form, comprising from about 0.05 mg to about 1000 mg, from about 0.1 mg to about 500 mg or from about 0.5 mg to about 200 mg of the compound.

45. A pharmaceutical composition according to claim 43 wherein the compound exhibits histamine H3 antagonistic activity or histamine H3 inverse agonistic activity.

* * * * *